United States Patent
Kulstad et al.

(10) Patent No.: US 10,716,703 B2
(45) Date of Patent: Jul. 21, 2020

(54) DEVICES AND METHODS FOR CONTROLLING PATIENT TEMPERATURE

(71) Applicant: Advanced Cooling Therapy, Inc., Chicago, IL (US)

(72) Inventors: Erik Kulstad, Palos Heights, IL (US); Hugh Patrick Caherty, Canton, MI (US)

(73) Assignee: Advanced Cooling Therapy, Inc., Chicago, IL (US)

(*) Notice: Subject to any disclaimer, the term of this patent is extended or adjusted under 35 U.S.C. 154(b) by 855 days.

(21) Appl. No.: 14/982,340

(22) Filed: Dec. 29, 2015

(65) Prior Publication Data

US 2016/0106578 A1    Apr. 21, 2016

Related U.S. Application Data

(63) Continuation of application No. 13/768,752, filed on Feb. 15, 2013, now Pat. No. 9,301,871, which is a continuation-in-part of application No. 13/609,624, filed on Sep. 11, 2012, now Pat. No. 9,326,890, which is a continuation-in-part of application No. 13/482,581, filed on May 29, 2012, now Pat. No.
(Continued)

(51) Int. Cl.
*A61F 7/12* (2006.01)
*A61F 7/00* (2006.01)
*A61B 90/00* (2016.01)
*A61B 17/00* (2006.01)

(52) U.S. Cl.
CPC ................ *A61F 7/12* (2013.01); *A61F 7/123* (2013.01); *A61B 2017/00084* (2013.01); *A61B 2090/064* (2016.02); *A61F 2007/0054* (2013.01); *A61F 2007/0095* (2013.01); *A61F 2007/126* (2013.01)

(58) Field of Classification Search
CPC .................................. A61F 7/12; A61F 7/123
See application file for complete search history.

(56) References Cited

U.S. PATENT DOCUMENTS

| 5,531,776 A | 7/1996 | Ward et al. |
| 5,624,392 A | 4/1997 | Saab |

(Continued)

FOREIGN PATENT DOCUMENTS

| JP | 2003507119 A | 2/2003 |
| JP | 2003524507 A | 8/2003 |

(Continued)

OTHER PUBLICATIONS

Povlishock JT, Wei EP. Posthypothermic Rewarming Considerations following Traumatic Brain Injury. Journal of Neurotrauma. 2009 3;26(3):333-340.

(Continued)

*Primary Examiner* — Kaitlyn E Smith
(74) *Attorney, Agent, or Firm* — Neal, Gerber & Eisenberg LLP; Kevin A. O'Connor

(57) ABSTRACT

Relatively non-invasive devices and methods for heating or cooling a patient's body are disclosed. Devices and methods for treating ischemic conditions by inducing therapeutic hypothermia are disclosed. Devices and methods for inducing therapeutic hypothermia through esophageal cooling are disclosed. Devices and methods for operative temperature management are disclosed.

20 Claims, 14 Drawing Sheets

Related U.S. Application Data 9,622,909, which is a continuation-in-part of application No. 13/021,805, filed on Feb. 7, 2011, now Pat. No. 8,444,684, and a continuation-in-part of application No. 13/021,820, filed on Feb. 7, 2011, now Pat. No. 8,523,929, and a continuation-in-part of application No. 13/021,828, filed on Feb. 7, 2011, now Pat. No. 8,696,725, said application No. 13/021,805 is a continuation of application No. 12/713,644, filed on Feb. 26, 2010, now Pat. No. 8,231,664, said application No. 13/021,820 is a continuation of application No. 12/713,644, filed on Feb. 26, 2010, now Pat. No. 8,231,664, said application No. 13/021,828 is a continuation of application No. 12/713,644, filed on Feb. 26, 2010, now Pat. No. 8,231,664.

(60) Provisional application No. 61/155,876, filed on Feb. 26, 2009.

(56) References Cited

U.S. PATENT DOCUMENTS

| | | | |
|---|---|---|---|
| 5,716,386 A | 2/1998 | Ward et al. | |
| 5,770,149 A | 6/1998 | Raible | |
| 5,800,493 A | 9/1998 | Stevens et al. | |
| 5,891,134 A | 4/1999 | Goble et al. | |
| 6,264,679 B1 | 7/2001 | Keller et al. | |
| 6,296,654 B1 | 10/2001 | Ward | |
| 6,338,727 B1 | 1/2002 | Noda | |
| 6,427,089 B1 | 7/2002 | Knowlton | |
| 6,488,673 B1 | 12/2002 | Laufer | |
| 6,547,811 B1 | 4/2003 | Becker et al. | |
| 6,572,638 B1 | 6/2003 | Dae et al. | |
| 6,592,612 B1 | 7/2003 | Samson | |
| 6,607,517 B1 | 8/2003 | Dae et al. | |
| 6,610,083 B2 | 8/2003 | Keller et al. | |
| 6,620,188 B1 | 9/2003 | Ginsburg et al. | |
| 6,645,233 B1 | 11/2003 | Ayers et al. | |
| 6,673,098 B1 | 1/2004 | Machold et al. | |
| 6,702,783 B1 | 3/2004 | Dae et al. | |
| 6,827,898 B1 | 12/2004 | Fausset et al. | |
| 6,830,581 B2 | 12/2004 | Magers | |
| 6,962,601 B2 | 11/2005 | Becker et al. | |
| 7,077,825 B1 | 7/2006 | Stull | |
| 7,172,586 B1* | 2/2007 | Dae | A61F 7/12 604/31 |
| 7,258,662 B2 | 8/2007 | Machold | |
| 7,318,834 B2 | 1/2008 | Njemanze | |
| 7,422,600 B2 | 9/2008 | Dobak, III | |
| 7,422,601 B2 | 9/2008 | Becker et al. | |
| 7,566,341 B2 | 7/2009 | Keller et al. | |
| 7,621,889 B2* | 11/2009 | Duong | A61F 7/12 604/101.02 |
| 7,621,890 B2* | 11/2009 | Duong | A61F 7/12 604/113 |
| 7,758,623 B2 | 7/2010 | Dzeng et al. | |
| 7,879,077 B2 | 2/2011 | MacHold et al. | |
| 7,896,009 B2 | 3/2011 | Stull | |
| 8,109,894 B2 | 2/2012 | Noda et al. | |
| 8,172,788 B2 | 5/2012 | Koninckx et al. | |
| 8,221,481 B2 | 7/2012 | Takeda et al. | |
| 8,231,664 B2 | 7/2012 | Kulstad et al. | |
| 8,303,637 B2 | 11/2012 | Mori | |
| 8,308,787 B2 | 11/2012 | Kreck | |
| 8,409,265 B2 | 4/2013 | Keller et al. | |
| 8,444,684 B2 | 5/2013 | Kulstad et al. | |
| 8,523,929 B2 | 9/2013 | Kulstad et al. | |
| 8,672,884 B2 | 3/2014 | Burnett et al. | |
| 8,696,725 B2 | 4/2014 | Kulstad et al. | |
| 9,237,964 B2 | 1/2016 | Keller et al. | |
| 9,301,871 B2 | 4/2016 | Kulstad et al. | |
| 9,320,644 B2 | 4/2016 | Kreck et al. | |
| 9,326,890 B2 | 5/2016 | Kulstad et al. | |
| 9,622,909 B2 | 4/2017 | Kulstad et al. | |
| 2001/0014799 A1 | 8/2001 | Schwartz | |
| 2001/0044643 A1 | 11/2001 | Litovitz | |
| 2001/0044644 A1 | 11/2001 | Keller et al. | |
| 2002/0007180 A1 | 1/2002 | Wittenberger et al. | |
| 2002/0026182 A1 | 2/2002 | Joye et al. | |
| 2002/0026227 A1 | 2/2002 | Philips | |
| 2002/0045925 A1 | 4/2002 | Keller et al. | |
| 2002/0183692 A1 | 12/2002 | Callister | |
| 2002/0183816 A1 | 12/2002 | Tzeng et al. | |
| 2003/0000526 A1 | 1/2003 | Gobel | |
| 2003/0004456 A1 | 1/2003 | Saab | |
| 2003/0040782 A1 | 2/2003 | Walker et al. | |
| 2003/0159700 A1 | 8/2003 | Laufer | |
| 2003/0195594 A1 | 10/2003 | Litovitz | |
| 2003/0195597 A1 | 10/2003 | Keller et al. | |
| 2004/0024437 A1 | 2/2004 | Machold et al. | |
| 2004/0082859 A1 | 4/2004 | Schaer | |
| 2004/0102825 A1 | 5/2004 | Daoud | |
| 2004/0116987 A1 | 6/2004 | Magers et al. | |
| 2004/0133256 A1 | 7/2004 | Callister | |
| 2004/0199229 A1 | 10/2004 | Lasheras | |
| 2004/0210281 A1 | 10/2004 | Dzeng et al. | |
| 2004/0220647 A1 | 11/2004 | Noda | |
| 2004/0223872 A1 | 11/2004 | Brian | |
| 2005/0004636 A1 | 1/2005 | Noda et al. | |
| 2005/0027281 A1 | 2/2005 | Lennox | |
| 2005/0032723 A1 | 2/2005 | Renzi | |
| 2005/0033391 A1 | 2/2005 | Worthen et al. | |
| 2005/0049475 A1 | 3/2005 | Gregersen | |
| 2005/0075705 A1 | 4/2005 | Machold et al. | |
| 2005/0177212 A1 | 8/2005 | Njemanze | |
| 2005/0203598 A1 | 9/2005 | Becker et al. | |
| 2005/0222652 A1* | 10/2005 | Mori | A61F 7/12 607/105 |
| 2006/0095032 A1 | 5/2006 | Jackson et al. | |
| 2006/0116564 A1 | 6/2006 | Mintchev et al. | |
| 2006/0122673 A1 | 6/2006 | Callister et al. | |
| 2006/0124141 A1 | 6/2006 | Dobak | |
| 2006/0276552 A1 | 12/2006 | Barbut et al. | |
| 2006/0282039 A1 | 12/2006 | Duong et al. | |
| 2006/0289016 A1 | 12/2006 | Kammer et al. | |
| 2007/0055328 A1 | 3/2007 | Mayse et al. | |
| 2007/0106247 A1 | 5/2007 | Burnett et al. | |
| 2007/0123813 A1 | 5/2007 | Barbut et al. | |
| 2007/0169779 A1 | 7/2007 | Freeman | |
| 2007/0244434 A1 | 10/2007 | Noda et al. | |
| 2007/0288075 A1 | 12/2007 | Dowlatshahi | |
| 2008/0077126 A1 | 3/2008 | Rashidi | |
| 2008/0091253 A1 | 4/2008 | Hammack et al. | |
| 2008/0119788 A1 | 5/2008 | Winter | |
| 2008/0161890 A1 | 7/2008 | Lafontaine | |
| 2008/0243112 A1 | 10/2008 | De Neve | |
| 2008/0249188 A1 | 10/2008 | Barbut et al. | |
| 2008/0275535 A1 | 11/2008 | Mori | |
| 2009/0069875 A1 | 3/2009 | Fishel | |
| 2009/0076573 A1 | 3/2009 | Burnett et al. | |
| 2009/0177258 A1 | 7/2009 | Takeda et al. | |
| 2009/0192447 A1 | 7/2009 | Andersen et al. | |
| 2009/0270955 A1 | 10/2009 | Magers et al. | |
| 2010/0030307 A1 | 2/2010 | Keller et al. | |
| 2010/0152822 A1 | 6/2010 | Callister et al. | |
| 2010/0168624 A1 | 7/2010 | Sliwa | |
| 2010/0204765 A1 | 8/2010 | Hall | |
| 2010/0211140 A1 | 8/2010 | Barbut | |
| 2010/0324635 A1 | 12/2010 | Kreck | |
| 2011/0120471 A1 | 5/2011 | Freeman | |
| 2011/0125234 A1 | 5/2011 | Kulstad et al. | |
| 2011/0130811 A1 | 6/2011 | Kulstad et al. | |
| 2011/0166633 A1 | 7/2011 | Stull | |
| 2011/0276115 A1 | 11/2011 | Merrill | |
| 2011/0301587 A1 | 12/2011 | Deem et al. | |
| 2012/0035603 A1 | 2/2012 | Lenihan | |
| 2012/0095537 A1 | 4/2012 | Hall | |
| 2012/0123509 A1 | 5/2012 | Merrill et al. | |
| 2012/0136343 A1 | 5/2012 | Burnett | |
| 2012/0197245 A1 | 8/2012 | Burnett et al. | |
| 2012/0265172 A1 | 10/2012 | Kulstad et al. | |
| 2012/0310312 A1 | 12/2012 | Yee | |
| 2013/0030411 A1 | 1/2013 | Kreck et al. | |

(56) References Cited

U.S. PATENT DOCUMENTS

| | | |
|---|---|---|
| 2013/0226077 A1 | 8/2013 | Burnett et al. |
| 2014/0031631 A1 | 1/2014 | Hall et al. |
| 2014/0135878 A1 | 5/2014 | Burnett et al. |
| 2014/0277304 A1 | 9/2014 | Stull |
| 2014/0343639 A1 | 11/2014 | Hopper et al. |
| 2015/0119962 A1 | 4/2015 | Kulstad et al. |
| 2016/0296365 A1 | 10/2016 | Kreck et al. |
| 2016/0354236 A1 | 12/2016 | Dae et al. |
| 2017/0281403 A1 | 10/2017 | Stull |
| 2018/0055687 A1 | 3/2018 | Keller et al. |
| 2018/0207028 A1 | 7/2018 | Hu et al. |
| 2018/0289539 A1 | 10/2018 | Stull |

FOREIGN PATENT DOCUMENTS

| | | |
|---|---|---|
| JP | 200775505 A | 3/2007 |
| WO | 1991005528 A1 | 5/1991 |
| WO | 1999005996 A1 | 2/1999 |
| WO | 01/13809 A1 | 3/2001 |
| WO | 01/64146 A1 | 9/2001 |
| WO | WO 2007/010073 A2 | 1/2007 |

OTHER PUBLICATIONS

Puccio AM, Fischer MR, Jankowitz BT, Yonas H, Darby JM, Okonkwo DO. Induced normothermia attenuates intracranial hypertension and reduces fever burden after severe traumatic brain injury. Neurocrit Care. 2009;11 (1):82-87.
Puttgen HA et al, Management of cardiac arrest patients to maximize neurologic outcome, Current Opinion in Critical Care 2009, 15:118-124.
Raina KD et al, Neurological and functional status following cardiac arrest: Method and tool utility, Resuscitation (2008) 79, 249-256.
Rajagopalan S, Mascha E, Na J, Sessler DI. The effects of mild perioperative hypothermia on blood loss and transfusion requirement. Anesthesiology. Jan. 2008;108(1):71-77.
Rasmussen YH et al, Forced-air surface warming versus oesophageal heat exchanges in the prevention of peroperative hypothermia, Acta Anaesthesiol Scand 1988; 42:348-352.
Rathinam S, Annam V, Steyn R, Raghuraman G. A randomised controlled trial comparing Mediwrap heat retention and forced air warming for maintaining normothermia in thoracic surgery. Interact Cardiovasc Thorac Surg. Jul. 2009;9 (1):15-19.
Reaven NL, Rosenbloom J. Commentary on the reimbursement paradox. Critical Care Medicine. Jul. 2009;37(7 Suppl): S285-289.
Rein L, Hospitals tally their avoidable mistakes, The Washington Post, Jul. 21, 2009.
Riter HG, Brooks LA, Pretorius AM, Ackermann LW, Kerber RE. Intra-arrest hypothermia: both cold liquid ventilation with perfluorocarbons and cold intravenous saline rapidly achieve hypothermia, but only cold liquid ventilation improves resumption of spontaneous circulation. Resuscitation. May 2009;80(5):561-566.
Rittenberger JC et al, Outcomes of a hospital-wide plan to improve care of comatose survivors of cardiac arrest, Resuscitation (2008) 79, 198-204.
Robert R, Entodoxin tolerance in humans in vivo, Crit Care Med 2009, vol. 37, No. 10, p. 2860.
Rodgers JB, Older TM, Stabler EV. Gastric hypothermia: a critical evaluation of its use in massive upper gastrointestinal bleeding. Annals of Surgery. Mar. 1966;163(3):367-372.
Rose C, Michalak A, Pannunzio M, Chatauret N, Rambaldi A, Butterworth RF Mild hypothermia delays the onset of coma and prevents brain edema and extracellular brain glutamate accumulation in rats with acute liver failure. Hepatology (Baltimore, Md. Apr. 2000;31(4):872-877.
Roth JV, Some unanswered questions about temperature management, The Open Mind, vol. 109, No. 5, Nov. 2009 pp. 1695-1699.
Roth JV, Hypothermia should also have been considered to be a predictor of adverse perioperative cardiac events, Anesthesiology 2009; 111:453-54.
Rothman SM. The therapeutic potential of focal cooling for neocortical epilepsy. Neurotherapeutics. Apr. 2009;6 (2):251-257.
Rupich K. The use of hypothermia as a treatment for traumatic brain injury. J Neurosci Nurs. Jun. 2009;41(3):159-167.
Rushing J. Responding to mild and moderate unintentional hypothermia. Nursing. Nov. 2008;38(11):22.
Russell ES. Unintentional hypothermia. Canadian Medical Association Journal. Oct. 7, 1961;85:846-847.
Safar P, Klain M, Tisherman S. Selective brain cooling after cardiac arrest. Crit Care Med. Jun. 1996;24(6):911-914.
Safar P. Mild hypothermia in resuscitation: a historical perspective. Annals of Emergency Medicine. Jun. 2003;41 (6):887-8888; author reply 888.
Safar PJ, Kochanek PM. Therapeutic hypothermia after cardiac arrest. The New England Journal of Medicine. Feb. 21, 2002;346(8):612-613.
Pittsburgh Post-Gazette obituary of Peter Safar, Aug. 5, 2003; available at http://www.post-gazette.com (accessed Feb. 24, 2009).
Sagalyn E, Band RA, Gaieski DF, Abella BS. Therapeutic hypothermia after cardiac arrest in clinical practice: review and compilation of recent experiences. Critical Care Medicine. Jul. 2009;37(7 Suppl):S223-226.
Sahu, Neurocognitive Function in Patients Undergoing Coronary Artery Bypass Graft Surgery with Cardiopulmonary Bypass: The Effect of Two Different Rewarming Strategies, Journal of Cardiothoracic and Vascular Anethesia, vol. 23, No. 1 Feb. 2009; pp. 14-21.
Sahuquillo J, Perez-Barcena J, Biestro A, Zavala E, Merino MA, Vilalta A, et al. Intravascular cooling for rapid induction of moderate hypothermia in severely head-injured patients: results of a multicenter study (IntraCool). Intensive Care Medicine [Internet]. Nov. 26, 2008;Available from: http://www.ncbi.nlm.nih.gov/entrez/query.fcgi?cmd=Retrieve&db=PubMed&dopt=Citation&list_uids=19034424.
Sanders AB. Therapeutic hypothermia after cardiac arrest. Curr Opin Crit Care. Jun. 2006;12(3):213-217.
Saxena M et al, Modest cooling therapies (35° C. to 37.5° C.) for traumatic brain injury, Cochrane Database of Systematic Reviews 2008, Issue 3. Art. No. CD006811.DOI:10.1002/14651858.CD006811.pub 2.
Schefold JC, Storm C, Hasper D. Prehospital therapeutic hypothermia in cardiac arrest: will there ever be evidence? Critical Care (London, England). 2008;12(2):413; author reply 413.
Schefold JC, Storm C, Krüger A, Ploner CJ, Hasper D. The Glasgow coma score is a predictor of good outcome in cardiac arrest patients treated with therapeutic hypothermia. Resuscitation [Internet]. 2009; 80(6):658-61. In Press, Corrected Proof. Available from: http://www.sciencedirect.com/science/article/B6T19-4W207JP-2/2/692dcdd818bd5be3f16c5cde0874122f.
Schein M, Rucinski J, Wise L. Perioperative normothermia and surgical-wound infection. The New England Journal of Medicine. Sep. 5, 1996;335(10):748-749; author reply 749-750.
Schilsky ML, Honiden S, Arnott L, Emre S. ICU management of acute liver failure. Clinics in Chest Medicine. Mar. 2009;30(1):71-87, viii.
Schratter A, et al, External cardiac defibrillation during wet-surface cooling in pigs, American Journal of Emergency Medicine (2007) 25, 420-424.
Schwab S, Schwarz S, Spranger M, Keller E, Bertram M, Hacke W. Moderate hypothermia in the treatment of patients with severe middle cerebral artery infarction. Stroke; A Journal of Cerebral Circulation. Dec. 1998;29(12):2461-2466.
Schwarz ES et al, Successful resuscitation of a patient in asystol after a TASER injury using a hypothermia protocol, American Journal of Emergency Medicine (2009) 27, 515.e1-515.e2.
Seder DB, Van der Kloot TE. Methods of cooling: practical aspects of therapeutic temperature management. Critical care medicine. Jul. 2009;37(7 Suppl):S211-22.
Seppelt I. Hypothermia does not improve outcome from traumatic brain injury. Crit Care Resusc. Sep. 2005;7 (3):233-237.

(56) References Cited

OTHER PUBLICATIONS

Sessler DI. Mild perioperative hypothermia. The New England Journal of Medicine. Jun. 12, 1997;336(24):1730-7.
Sessler DI. Temperature monitoring and perioperative thermoregulation. Anesthesiology. Aug. 2008;109(2):318-38.
Sessler DI. Thermoregulatory defense mechanisms. Critical Care Medicine. Jul. 2009;37(7 Suppl):S203-10.
Seule MA, Muroi C, Mink S, Yonekawa Y, Keller E. Therapeutic Hypothermia in Patients with Aneurysmal Subarachnoid Hemorrhage, Refractory Intracranial Hypertension, or Cerebral Vasospasm. Neurosurgery. Nov. 27, 2008; [Internet] Available from: http://www.ncbi.nlm.nih.gov/entrez/query.fcgi?cmd=Retrieve&db=PubMed&dopt=Citation&list_uids=19050656.
Shankaran S. Neonatal Encephalopathy: Treatment with Hypothermia. Journal of Neurotrauma. 2009 3;26(3):437-443.
Sharon RY, Management of patient body temperature is challenging, Anesthesiology, v 100, No. 3, p. 747, Mar. 2004.
Shibuya S, Miyamoto O, Janjua NA, Itano T, Mod S, Norimatsu H. Post-traumatic moderate systemic hypothermia reduces TUNEL positive cells following spinal cord injury in rat. Spinal Cord. Jan. 2004;42(1):29-34.
Silfvast T, Tiainen M, Poutiainen E, Roine RO. Therapeutic hypothermia after prolonged cardiac arrest due to non-coronary causes. Resuscitation. Apr. 2003;57(1):109-112.
Sim M, Dean P, Booth M, Kinsella J. Uptake of therapeutic hypothermia following out-of-hospital cardiac arrest in Scottish Intensive Care Units. Anaesthesia. Aug. 2008;63(8):886-8877; author reply 887.
Simosa HF, Petersen DJ, Agarwal SK, Burke PA, Hirsch EF. Increased risk of deep venous thrombosis with endovascular cooling in patients with traumatic head injury. The American Surgeon. May 2007;73(5):461-464.
Skowronski GA. Therapeutic hypothermia after cardiac arrest—not so fast. Crit Care Resusc. Dec. 2005;7(4):322-324.
Skulec R, Dostalova G, Kovarnik T, Linhart A, Seblova J. Therapeutic hypothermia in cardiac arrest survivors: A survey of practice in the Czech Republic. Resuscitation. Jun. 2008;77(3):419-420.
Notification Concerning Transmittal of International Preliminary Report on Patentability (Chapter I or the Patent Cooperation Treaty) dated Sep. 9, 2011 and International Preliminary Report on Patentability dated Aug. 30, 2011 including Written Opinion of the International Searching Authority in PCT application No. PCT/US2010/025523.
Office Action for U.S. Appl. No. 12/713,644, dated May 8, 2012.
Office Action for U.S. Appl. No. 13/021,805, dated Oct. 4, 2012.
Abella BS, Gaieski DF. U Penn Center for Resuscitation Science Q & A page; available at http://www.med.upenn.edu/resuscitation/QandA.shtml (Updated Jul. 5, 2011) (Accessed Nov. 8, 2012).
Office Action dated Oct. 23, 2013 from U.S. Appl. No. 13/021,828, pp. 1-10.
Office Action for U.S. Appl. No. 13/021,805, dated Feb. 21, 2013.
Office Action for U.S. Appl. No. 13/021,820, dated Feb. 25, 2013.
Office Action for U.S. Appl. No. 13/021,828, dated Dec. 21, 2012.
A Tribute to Dr. Hubert L. Rosomoff: A Pioneer in Treatment of Pain and Use of Hypothermia. Journal of Neurotrauma. 2009 3;26(3)299-300.
Abella BS, Gaieski DF. U Penn Center for Resuscitation Science Q & A page [Internet]; Available from: http://www.med.upenn.edu/resuscitation/QandA.shtml (Updated Oct. 15, 2010) (Accessed Apr. 2011).
Abella BS, Rhee JW, Huang KN, Vanden Hoek TL, Becker LB. Induced hypothermia is underused after resuscitation from cardiac arrest: a current practice survey. Resuscitation. Feb. 2005;64(2):181-6.
Acosta P et al, Therapeutic hypothermia—From the bench to the bedside: Are we there yet?, Resuscitation (2008) 79, 183-184.
Adelson PD. Hypothermia following pediatric traumatic brain injury. J. Neurotrauma. Mar. 2009;26(3):429-436.
Alzaga AG, Cerdan M, Varon J. Therapeutic hypothermia. Resuscitation. Sep. 2006;70(3):369-380.

American Heart Association Guidelines for Cardiopulmonary Resuscitation and Emergency Cardiovascular Care. Circulation. Dec. 13, 2005;112(24 Suppl):IV1-203.
American Heart Association, Heart Disease and Stroke Statistics—2008 Update. Dallas, TX: American Heart Association; 2008.
American Heart Association, Out-Of-Hospital Cardiac Arrest—Statistics (2004).
American Heart Association, Heart Disease and Stroke Statistics (2009).
Andrews PJ, Harris B, Murray GD. Randomized controlled trial of effects of the airflow through the upper respiratory tract of intubated brain-injured patients on brain temperature and selective brain cooling. British Journal of Anaesthesia. Mar. 2005;94(3):330-335.
Avidan MS, Jones N, Ing R, Khoosal M, Lundgren C, Morrell DF. Convection warmers—not just hot air. Anaesthesia. Nov. 1997;52(11):1073-1076.
Azzopardi DV, Strohm B, Edwards AD, Dyet L, Halliday HL, Juszczak E, et al. Moderate hypothermia to treat perinatal asphyxial encephalopathy. N. Engl. J. Med. Oct. 1, 2009;361(14):1349-1358.
Badjatia N, O'Donnell J, Baker JR, Huang D, Ayata C, Greer DM, et al. Achieving normothermia in patients with febrile subarachnoid hemorrhage: feasibility and safety of a novel intravascular cooling catheter. Neurocritical Care. 2004;1 (2):145-56.
Badjatia N, Hyperthermia and fever control in brain injury. Crit Care Med. Jul. 2009;37(7 Suppl):S250-257.
Badjatia N, Fever control in the neuro-ICU: why, who, and when? Current Opinion in Critical Care (2009) 15:79-82.
Band RA, Abella BS. Hypothermia and cardiac arrest: the promise of intra-arrest cooling. Critical Care (London, England). 2008;12(2):138.
Battin MR, Thoresen M, Robinson E, Polin RA, Edwards AD, Gunn AJ. Does head cooling with mild systemic hypothermia affect requirement for blood pressure support? Pediatrics. Mar. 2009;123(3):1031-6.
Baughman VL. Brain protection during neurosurgery. Anesthesiology Clinics of North America. Jun. 2002;20 (2):315-327, vi.
Bayegan K et al, Rapid non-invasive external cooling to induce mild therapeutic hypothermia in adult human-sized swine, Resuscitation (2008) 76, 291-298.
Beck E. et al.—Efficacy of intraoperative heat administration by ventilation with warm humidified gases and an pesophageal warming system, British Journal of Anaesthesia, 77:530-533 (1966).
Bekkers et al, Hypothermia for out-of-hospital cardiac arrest survivors: A single-center experience, doi:10.1016/j.ajem.2007.06.008 pp. 1078-1080.
Belliard G, Catez E, Charron C, Caille V, Aegerter P, Dubourg O, et al. Efficacy of therapeutic hypothermia after out-of-hospital cardiac arrest due to ventricular fibrillation. Resuscitation. Nov. 2007;75(2):252-259.
Benjamin HB et al, Regional hypothermia and its effect on the brain, American Journal of Surgery, vol. 100 Jul. 1960.
Benson DW, Williams GR, Jr., Spencer FC, Yates AJ. The use of hypothermia after cardiac arrest. Anesthesia and Analgesia. Nov.-Dec. 1959;38:423-428.
Benzer A, Sparr HJ. Perioperative normothermia and surgical-wound infection. N Engl J Med. Sep. 5, 1996;335 (10):747; author reply 749-750.
Bernard S. Hypothermia after cardiac arrest: expanding the therapeutic scope. Crit Care Med. Jul. 2009;37(7 Suppl): S227-233.
Bernard S. Therapeutic hypothermia after cardiac arrest: now a standard of care. Crit Care Med. Mar. 2006;34 (3):923-924.
Bernard SA, Buist M. Induced hypothermia in critical care medicine: a review. Critical Care Med. Jul. 2003;31 (7):2041-2051.
Bernard SA, Gray TW, Buist MD, Jones BM, Silvester W, Gutteridge G, et al. Treatment of comatose survivors of out-of-hospital cardiac arrest with induced hypothermia. The New England Journal of Medicine. Feb. 21, 2002;346 (8):557-63.
Bernard SA. Therapeutic hypothermia after cardiac arrest. Hypothermia is now standard care for some types of cardiac arrest. Med J Aust. Nov. 1, 2004;181(9):468-469.
Bernard SA et al, Clinical trial of induced hypothermia in comatose survivors of out-of-hospital cardiac arrest. Annals of Emergency Medicine Aug. 30, 1997:2, pp. 146-153.

(56) References Cited

OTHER PUBLICATIONS

Bianchin A, Pellizzato N, Martano L, et al. Therapeutic Hypothermia in Italian Intensive Care Units: a national survey. Minerva anestesiologica. Dec. 17, 2008. [Internet]. Available from: http://www.ncbi.nlm.nih.gov/entrez/query.fcgi?cmd=Retrieve&db=PubMed&dopt=Citation&list_uids=19088699.

Borgquist O, Friberg H. Therapeutic hypothermia for comatose survivors after near-hanging-a retrospective analysis. Resuscitation. Feb. 2009;80(2):210-212.

Braslow D. The Withholding of Therapeutic Hypothermia's Malpractice? [Internet]. Jun. 16, 2009; Available from: http://www.druginjurylawyerblog.com/2008/12/the_withholding_of therapeutic.html.

Bro-Jeppesen J, Kjaergaard J, Horsted TI, Wanscher MC, Nielsen SL, Rasmussen LS, et al. The impact of therapeutic hypothermia on neurological function and quality of life after cardiac arrest. Resuscitation. Feb. 2009;80(2):171-6.

Brooks SC, Morrison LJ. Implementation of therapeutic hypothermia guidelines for post-cardiac arrest syndrome at a glacial pace: Seeking guidance from the knowledge translation literature. Resuscitation. Jun. 2008;77(3):286-292.

Bryant LR, Mobin-Uddin K, Dillon ML, Griffen WO. Comparison of ice water with iced saline solution for gastric lavage in gastroduodenal hemorrhage. American Journal of Surgery. Nov. 1972;124(5):570-572.

Burns SM, Wojnakowski M, Piotrowski K, Caraffa G. Unintentional hypothermia: implications for perianesthesia nurses. J Perianesth Nurs. Jun. 2009;24(3):167-73; quiz 174-6.

Cajigal S, Football player's spine treatment shines spotlight on hypothermia, Neurology Today, Nov. 20, 2007, pp. 15-17.

Carr BG et al, Inter-hospital variability in post-cardiac arrest mortality. Resuscitation 90 (2009) 30-34.

Castrejón S, Cortés M, Salto ML, Benittez LC, Rubio R, Juárez M, et al. Improved prognosis after using mild hypothermia to treat cardiorespiratory arrest due to a cardiac cause: comparison with a control group. Rev Esp Cardiol. Jul. 2009;62(7):733-741.

Celik T, et al, Chill therapy in the patients with resuscitated cardiac arrest: A new weapon in the battle against anoxic brain injury, Int'l Journal of Cardiology, 11167 (2008).

Chen J, Ji X, Ding Y, et al. A novel approach to reduce hemorrhagic transformation after interventional management of acute stroke: Catheter-based selective hypothermia. Medical Hypotheses. Jan. 2009;72(1):62-63.

Chen Z et al, The effects of large blood vessels on temperature distributions during simulated hyperthermia, Journal of Biomechanical Engineering, Nov. 1992, vol. 114; 473-81.

Choi R et al, Intraoperative hypothermia during vascular neurosurgical procedures, Neurosurg Focus 26(5):E24, 2009.

Christian E, Zada G, Sung G, et al. A review of selective hypothermia in the management of traumatic brain injury. Neurosurgical Focus, Oct. 2008;25(4):E9.

Claessens-Van Ooijen et al, Heat production and body temperature during cooling and rewarming in overweight and lean men, Obesity, vol. 14, No. 11 Nov. 2006, 1914-1920.

Clifton GL, Dreyer P, Valadka A, Zygun D, Okonkwo D. Multicenter Trial of Early Hypothermia in Severe Brain Injury. Journal of Neurotrauma. Mar. 2009;26(3):393-397.

Clifton GL, Miller ER, Choi SC, Levin HS, McCauley S, Smith KR, et al. Hypothermia on admission in patients with severe brain injury. Journal of Neurotrauma. Mar. 2002;19(3):293-301.

Hachimi-Idrissi S, Come L, Ebinger G, Michotte Y, Huyghens L. Mild hypothermia induced by a helmet device: a clinical feasibility study. Resuscitation. Dec. 2001;51(3):275-281.

Hachimi-Idrissi S, Huyghens L. Therapeutic hypothermia after traumatic brain injury in children: to cool or not to cool? Resuscitation. Nov. 2008;79(2):185-186.

Hammel CL, et al, Prehospital management of severe traumatic brain injury, BMJ, May 23, 2009, vol. 338, pp. 1262-1266.

Hammersborg SM et al—Surface cooling versus core cooling: Comparative studies of microvascular fluid- and protein-shifts in a porcine model, Resuscitation (2008) 79, 292-300.

Hannenberg AA, Sessler DI. Improving perioperative temperature management. Anesthesia and Analgesia. Nov. 2008;107(5):1454-1457.

Hardy JD et ai, Heat loss from the nude body and peripheral blood flow at temperatures of 220C. to 350C., The Journal of Nutrition, 16(5):493-510 (Nov. 1938).

Harper CM, McNicholas T, Gowrie-Mohan S. Maintaining perioperative normothermia. BMJ (Clinical Research Ed. Apr. 5, 2003;326(7392):721-722.

Harris B et al, Internasal selective brain cooling in pigs, Resuscitation pp. 102-103, doi:10.1016/j.resuscitation.2008.02.013.

Harris BA, Andrews PJ, Murray GD. Enhanced upper respiratory tract airflow and head fanning reduce brain temperature in brain-injured, mechanically ventilated patients: a randomized, crossover, factorial trial. British Journal of Anaesthesia. Jan. 2007;98(1):93-99.

Harris OA, Colford JM, Jr., Good MC, et al. The role of hypothermia in the management of severe brain injury: a meta-analysis. Archives of Neurology. Jul. 2002;59(7):1077-1083.

Harris OA, Muh CR, Surles MC, Pan Y, Rozycki G, Macleod J, et al. Discrete cerebral hypothermia in the management of traumatic brain injury: a randomized controlled trial. J. Neurosurg. Jun. 2009;110(6):1256-1264.

Hartemink KJ et al., Novel applications of therapeutic hypothermia: Report of three cases, Critical Care, Oct. 2004, vol. 8, No. 5, pp. R343-R346.

Haugk M et al, Feasibility and efficacy of a new non-invasive surface cooling device in post resuscitation intensive care medicine, Resuscitation (2007) 75, 76-81.

Hayashi N. Management of Pitfalls for the Successful Clinical Use of Hypothermia Treatment. Journal of Neurotrauma. Mar. 2009;26(3):445-453.

Hearn CM, Chandradeva K. Maintaining perioperative normothermia: hyperthermia must be avoided. BMJ (Clinical Research Ed. Jun. 28, 2003;326(7404):1457.

Hemmen TM, Lyden PD. Hypothermia after Acute Ischemic Stroke. Journal of Neurotrauma. Mar. 2009;26(3):387-391.

Herr DL, Badjatia N. Therapeutic temperature management: why, who, when, where, and how. Critical Care Medicine. Jul. 2009;37(7 Suppl):S185.

Hinz J, Rosmus M, Popov A, Moerer O, Frerichs I, Quintel M. Effectiveness of an intravascular cooling method compared with a conventional cooling technique in neurologic patients. Journal of Neurosurgical Anesthesiology. Apr. 2007;19(2):130-135.

Hoda MR, Popken G. Maintaining perioperative normothermia during laparoscopic and open urologic surgery. Journal of Endourology / Endourological Society. May 2008;22(5):931-938.

Hoedemaekers CW, Ezzahti M, Gerritsen A, van der Hoeven JG. Comparison of cooling methods to induce and maintain normo- and hypothermia in intensive care unit patients: a prospective intervention study. Critical Care (London, England). 2007;11(4):R91.

Holzer M, Bernard SA, Hachimi-Idrissi S, et al. Hypothermia for neuroprotection after cardiac arrest: systematic review and individual patient data meta-analysis. Crit Care Med. Feb. 2005;33(2):414-418.

Holzer M et al, Mild therapeutic hypothermia to improve the neurologic outcome after cardiac arrest. N Engl J Med. Feb. 21, 2002;346(8):549-556.

Holzer M, Mullner M, Sterz F, Robak O, Kliegel A, Losert H, et al. Efficacy and safety of endovascular cooling after cardiac arrest: cohort study and Bayesian approach. Stroke; A Journal of Cerebral Circulation. Jul. 2006;37(7)1792-7.

Holzer, Arrich J., et al., Hypothermia for neuroprotection in adults after cardiopulmonary resuscitation. Chochrane Database of Systematic Reviews 2009, Issue 4. Art. No. CD004128. (version first published online: Oct. 7, 2009 in Issue 4, 2009.).

Horn A et al, Induced hypothermia for infants with hypoxic-ischemic encephalopathy using a servo-controlled fan: an exploratory pilot study, Journal of the American Academy of Pediatrics (2009) pp. 1090-1098.

(56) References Cited

OTHER PUBLICATIONS

Hsu CY, Huang CH, Chang WT, Chen HW, Cheng HJ, Tsai MS, et al. Cardioprotective effect of therapeutic hypothermia for post-resuscitation myocardial dysfunction. Shock (Augusta, Ga Dec. 4, 2008 [Internet]. Available from: http://www.ncbi.nlm.nih.gov/entrez/query.fcgi?cmd=Retrieve&db=PubMed&dopt=Citation&list_uids=19060788.

Huet O, Kinirons B, Dupic L, et al. Induced mild hypothermia reduces mortality during acute inflammation in rats. Acta anaesthesiologica Scandinavica. Oct. 2007;51(9):1211-1216.

Hutchison JS, Doherty DR, Orlowski JP, Kissoon N. Hypothermia therapy for cardiac arrest in pediatric patients. Pediatric Clinics of North America. Jul. 2008;55(3):529-44, ix.

Hutchison JS, Ward RE, Lacroix J, Hebert PC, Barnes MA, Bohn DJ, et al. Hypothermia therapy after traumatic brain injury in children. The New England Journal of Medicine. Jun. 5, 2008;358(23):2447-56.

Inaba K et al, Mortality impact of hypothermia after cavitary explorations in trauma, world, J Surg (2009) 33:864-869.

Inamasu J, Ichikizaki K. Mild hypothermia in neurologic emergency: an update. Annals of Emergency Medicine. Aug. 2002;40(2):220-230.

Janata A, Weihs W, Bayegan K, Schratter A, Holzer M, Behringer W, et al. Therapeutic hypothermia with a novel surface cooling device improves neurologic outcome after prolonged cardiac arrest in swine. Critical Care Medicine. Mar. 2008;36(3):895-902.

Janicki PK, Higgins MS, Janssen J, Johnson RF, Beattie C. Comparison of two different temperature maintenance strategies during open abdominal surgery: upper body forced-air warming versus whole body water garment. Anesthesiology. Oct. 2001;95(4):868-74.

Jiang J. Clinical study of mild hypothermia treatment for severe traumatic brain injury. J. Neurotrauma. Mar. 2009;26 (3):399-406.

Jimmink JJ, Binnekade JM, Paulus F, Mathus-Vliegen EMH, Schultz MJ, Vroom MB. The influence of body composition on therapeutic hypothermia: a prospective observational study of patients after cardiac arrest. Crit Care. 2008;12(4):R87.

Kabbara A, Goldlust SA, Smith CE, Hagen JF, Pinchak AC. Randomized prospective comparison of forced air warming using hospital blankets versus commercial blankets in surgical patients. Anesthesiology. Aug. 2002;97 (2):338-44.

Kamarainen A, Virkkunen I, Tenhunen J, Yli-Hankala A, Silfvast T. Induction of therapeutic hypothermia during prehospital CPR using ice-cold intravenous fluid. Resuscitation [Internet]. Sep. 20, 2008;Available from: http://www.ncbi.nlm.nih.gov/entrez/query.fcgi?cmd=Retrieve&db=PubMed&dopt=Citation&list_uids=18809236.

Kamarainen A, Virkkunen I, Tenhunen J, Yli-Hankala A, Silfvast T. Prehospital therapeutic hypothermia for comatose survivors of cardiac arrest: a randomized controlled trial. Acta Anaesthesiologica Scandinavica [Internet]. Jun. 3, 2009; Available from: http://www.ncbi.nlm.nih.gov/entrez/query.fcgi?cmd=Retrieve&db=PubMed&dopt=Citation&list_uids=19496762.

Kamarainen A, et al, Prehospital induction of therapeutic hypothermia during CPR: A pilot study, Resuscitation (2008) 76, 360-363.

Kapetanakis A, Azzopardi D, Wyatt J, Robertson NJ. Therapeutic hypothermia for neonatal encephalopathy: a UK survey of opinion, practice and neuro-investigation at the end of 2007. Acta Paediatr [Internet]. 2008;Available from: http://www.ncbi.nlm.nih.gov/entrez/query.fcgi?cmd=Retrieve&db=PubMed&dopt=Citation&list_uids=19076983.

Kates L, Schraga E. Cooling Techniques for Hyperthermia: Treatment & Medication [Internet]. Apr. 4, 2009;Available from: http://emedicine.medscape.com/article/149546-overview.

Kawanishi M, Kawai N, Nakamura T, et al. Effect of delayed mild brain hypothermia on edema formation after intracerebral hemorrhage in rats. J Stroke Cerebrovasc Dis. Jul.-Aug. 2008;17(4):187-195.

Keresztes PA, Brick K. Therapeutic hypothermia after cardiac arrest. Dimens Crit Care Nurs. Mar.-Apr. 2006;25(2):71-6.

Khalil HH, Mackeith RC. A simple method of raising and lowering body temperature. British Medical Journal. Sep. 25, 1954;2(4890):734-736.

Kiessling AH, Isgro F, Lehmann A, Piper S, Blome M, Saggau W. Evaluating a new method for maintaining body temperature during OPCAB and robotic procedures. Med Sci Monit. Jul. 2006;12(7):MT39-42.

Kilgannon JH, Roberts BW, Stauss M, Cimino MJ, Ferchau L, Chansky ME, et al. Use of a standardized order set for achieving target temperature in the implementation of therapeutic hypothermia after cardiac arrest: a feasibility study. Acad Emerg Med. Jun. 2008;15(6):499-505.

Kim F, Olsufka M, Carlborn D, Deem S, Longstreth WT, Hanrahan M, et al. Pilot study of rapid infusion of 2 L of 4 degrees C normal saline for induction of mild hypothermia in hospitalized, comatose survivors of out-of-hospital cardiac arrest. Circulation. Aug. 2, 2005;112(5):715-719.

Kim F, Olsufka M, Longstreth WT, Maynard C, Carlborn D, Deem S, et al. Pilot randomized clinical trial of prehospital induction of mild hypothermia in out-of-hospital cardiac arrest patients with a rapid infusion of 4 degrees C normal saline. Circulation. Jun. 19, 2007;115(24):3064-3070.

Kim F, Olsufka M, Nichol G, Copass MK, Cobb LA. The Use of Pre-Hospital Mild Hypothermia after Resuscitation from Out-of-Hospital Cardiac Arrest. Journal of Neurotrauma. 2009 3;26(3):359-363.

Kim Young-Min et al, Use of cold intravenous fluid to induce hypothermia in a comatose child after cardiac arrest due to a lightning strike, Resuscitation (2008) 79, 336-338.

Presciutti M, Bader MK, Hepburn M. Shivering management during therapeutic temperature modulation: nurses' perspective. Crit Care Nurse. 2012;32(1):33-42.

Taniguchi Y, Lenhardt R, Sessler DI, Kurz A. The Effect of Altering Skin-Surface Cooling Speeds on Vasoconstriction and Shivering Thresholds. Anesth Analg. 2011.

Jarrah S, Dziodzio J, Lord C, Fraser GL, Lucas L, Riker RR, et al. Surface Cooling after Cardiac Arrest: Effectiveness, Skin Safety, and Adverse Events in Routine Clinical Practice. Neurocrit Care. 2011.

Usta B, Gozdemir M, Demircioglu RI, Muslu B, Sert H, Yaldiz A. Dexmedetomidine for the prevention of shivering during spinal anesthesia. Clinics (Sao Paulo). 2011;66(7):1187-91.

May T, Seder DB, Fraser GL, Tu C, McCrum B, Lucas L, et al. Association of the Bedside Shivering Assessment Scale and derived EMG power during therapeutic hypothermia in survivors of cardiac arrest. Resuscitation. 2011.

Scaravilli V, Tinchero G, Citerio G. Fever management in SAH. Neurocrit Care. 2011;15(2):287-94.

Weant KA, Martin JE, Humphries RL, Cook AM. Pharmacologic options for reducing the shivering response to therapeutic hypothermia. Pharmacotherapy. 2010;30(8):830-41.

Logan A, Sangkachand P, Funk M. Optimal management of shivering during therapeutic hypothermia after cardiac arrest. Crit Care Nurse. 2011;31(6):e18-30.

Asl ME, Isazadefar K, Mohammadian A, Khoshbaten M. Ondansetron and meperidine prevent postoperative shivering after general anesthesia. Middle East J Anesthesiol. 2011;21(1):67-70.

Jurado LV, Gulbis BE. Continuous infusion versus intermittent bolus dosing of vecuronium in patients receiving therapeutic hypothermia after sudden cardiac arrest. Pharmacotherapy. 2011;31(12):1250-6.

Choi HA, Ko SB, Presciutti M, Fernandez L, Carpenter AM, Lesch C, et al. Prevention of shivering during therapeutic temperature modulation: the Columbia anti-shivering protocol. Neurocrit Care. 2011;14(3):389-94.

Merchant RM, Abella BS, Peberdy MA, Soar J, Ong ME, Schmidt GA, et al. Therapeutic hypothermia after cardiac arrest: unintentional overcooling is common using ice packs and conventional cooling blankets. Critical care medicine. 2006;34(12 Suppl):S490-4-S-4.

Polderman KH. Application of therapeutic hypothermia in the intensive care unit. Opportunities and pitfalls of a promising treat-

(56) References Cited

OTHER PUBLICATIONS ment modality—Part 2: Practical aspects and side effects. Intensive care medicine. 2004;30(5):757-69.
Sessler DI. Complications and treatment of mild hypothermia. Anesthesiology. 2001;95(2):531-43.
Hoque N, Chakkarapani E, Liu X, Thoresen M. A Comparison of Cooling Methods Used in Therapeutic Hypothermia for Perinatal Asphyxia. Pediatrics. 2010.
Knapik P, Rychlik W, Siedy J, Nadziakiewicz P, Ciesla D. Comparison of intravascular and conventional hypothermia after cardiac arrest. Kardiol Pol. 2011;69(11):1157-63.
Topjian A, Hutchins L, Diliberto MA, Abend N, Ichord R, Helfaer M, et al. Induction and maintenance of therapeutic hypothermia after pediatric cardiac arrest: Efficacy of a surface cooling protocol. Pediatr Crit Care Med. 2010.
Flint AC, Hemphill JC, Bonovich DC. Therapeutic hypothermia after cardiac arrest: performance characteristics and safety of surface cooling with or without endovascular cooling. Neurocrit Care. 2007;7(2):109-18.
Tsai YF, Liu FC, Lin CC, Lee WC, Yu HP. Tying a slipknot to an intubation stylet for facilitating insertion of a nasogastric tube in liver transplant recipients: a prospective, randomized study. Transplant Proc. 2012;44(2):438-41.
Hung CW, Lee WH. A novel method to assist nasogastric tube insertion. Emerg Med J. 2008;25(1):23-5.
Chun DH, Kim NY, Shin YS, Kim SH. A randomized, clinical trial of frozen versus standard nasogastric tube placement. World J Surg. 2009;33(9):1789-92.
Kirtania J, Ghose T, Garai D, Ray S. Esophageal guidewire-assisted nasogastric tube insertion in anesthetized and intubated patients: a prospective randomized controlled study. Anesth Analg. 2012;114(2):343-8.
Smith CE et al, Hypothermia in Trama Victims, ASA Newsletter Nov. 2005.
Smith TL, Bleck TP. Hypothermia and neurologic outcome in patients following cardiac arrest: should we be hot to cool off our patients? Critical Care (London, England). Oct. 2002;6(5):377-80.
Soreide E, Sunde K. Therapeutic hypothermia after out-of hospital cardiac arrest: how to secure worldwide implementation. Current Opinion in Anaesthesiology. Apr. 2008;21(2):209-215.
Soreide E. Prehospital cooling in cardiac arrest—the next frontier? Scand J Trauma Resusc Emerg Med. Oct. 12, 2009;17(1):54.
Busch, et al, Rapid implementation of therapeutic hypothermia in comatose out-of-hospital cardiac arrest survivors, Acta Anaesthesiol Scand 2006;50:1277-1283.
Srikameswaran A, Dr. peter Safar: A life devoted to cheating death, Post-gazette.com, http://www.post-gazette.com (Mar. 31, 2002).
Sterz F et al, Therapeutic hypothermia following cardiac arrest, SICS EBMG 2004.
Sterz F et al, Resuscitative hypothermia after cardiac arrest, 2003 SAEM Annual Meeting Handout.
Storm C, Gebker R, Krüger A, Nibbe L, Schefold JC, Martens F, et al. A rare case of neuroleptic malignant syndrome presenting with serious hyperthermia treated with a non-invasive cooling device: a case report. J Med Case Reports. 2009;3:6170.
Storm C, Schefold JC, Kerner T, Schmidbauer W, Gloza J, Krueger A, et al. Prehospital cooling with hypothermia caps (PreCoCa): a feasibility study. Clin Res Cardiol. Oct. 2008;97(10):768-772.
Storm C, Schefold JC, Nibbe L, Martens F, Krueger A, Oppert M, et al. Therapeutic hypothermia after cardiac arrest—the implementation of the ILCOR guidelines in clinical routine is possible! Crit Care. Nov. 2, 2006;10(6):425.
Storm C, Steffen I, Schefold JC, Krueger A, Oppert M, Jorres A, et al. Mild therapeutic hypothermia shortens intensive care unit stay of survivors after out-of-hospital cardiac arrest compared to historical controls. Critical Care (London, England). 2008;12(3):R78.
Stravitz RT, Larsen FS. Therapeutic hypothermia for acute liver failure. Crit Care Med. Jul. 2009;37(7 Suppl):S258-264.
Suffoletto B, Peberdy MA, van der Hoek T, Callaway C. Body temperature changes are associated with outcomes following in-hospital cardiac arrest and return of spontaneous circulation. Resuscitation [Internet]. Oct. 3, 2009 [cited Oct. 10, 2009];Available from: http://www.ncbi.nlm.nih.gov/pubmed/19804929.
Sugerman NT, Abella BS. Hospital-Based Use of Therapeutic Hypothermia after Cardiac Arrest in Adults. Journal of Neurotrauma. 2009 3;26(3):371-376.
Patent Cooperation Treaty, Notification of Transmittal of the International Search Report and The Written Opinion of the International Searching Authority, in PCT/US2010/025523, dated Oct. 20, 2010.
Taguchi A, Ratnaraj J, Kabon B, Sharma N, Lenhardt R, Sessler DI, et al. Effects of a circulating-water garment and forced-air warming on body heat content and core temperature. Anesthesiology. May 2004;100(5):1058-64.
Tang XN, Liu L, Yenari MA. Combination Therapy with Hypothermia for Treatment of Cerebral Ischemia. Journal of Neurotrauma. Mar. 2009;26(3):325-331.
Thakor AS, Levy N. A new effective non-invasive method of cooling patients with malignant hyperthermia. Anaesthesia. Nov. 2008;63(11):1266-1267.
Tiainen et al, Arrhthmias and Heart Rate Variability During and After Therapeutic Hypothermia for Cardiac Arrest, Crit Care Med 2009, vol. 37, No. 2.
Tisherman SA, Rodriguez A, Safar P. Therapeutic hypothermia in traumatology. The Surgical Clinics of North America. Dec. 1999;79(6):1269-1289.
Tisherman SA. Hypothermia and injury. Curr Opin Crit Care. Dec. 2004;10(6):512-519.
Todd MM, Hindman BJ, Clarke WR, Torner JC, Weeks JB, Bayman EO, et al. Perioperative fever and outcome in surgical patients with aneurysmal subarachnoid hemorrhage. Neurosurgery. May 2009;64(5):897-908; discussion 908.
Toma A, Bensimon CM, Dainty KN, Rubenfeld GD, Morrison LJ, Brooks SC. Perceived barriers to therapeutic hypothermia for patients resuscitated from cardiac arrest: A qualitative study of emergency department and critical care workers*. Crit Care Med [Internet]. Dec. 15, 2009 [cited Dec. 19, 2009];Available from: http://www.ncbi.nlm.nih.gov/pubmed/20016377.
Torossian A. Thermal management during anaesthesia and thermoregulation standards for the prevention of inadvertent perioperative hypothermia. Best Practice & Research. Dec. 2008;22(4):659-668.
Trentman TL et al, Randomized non-inferiority trial of the vital HEATtm temperature management system vs the Bair Hagger® warmer during total knee arthroplasty, Can J Anesth/J Can Anesth (2009) DOI 10.1007/s12630-009-9199.2.
Tsuchiya et al, Atrial Fibrillation Ablation With Esophageal Cooling With A Cooled Water—Irrigated Intraesophageal Balloon, Journal of Cardiovascular Electrophysiology, vol. 18, Nov. 2, Feb. 2007.
Tsuchiya T. The Challenges of Preventing Lethal Esophageal Damage During Atrial Fibrillation Ablation Continue, J Cardiovasc Electrophysiol, vol. 19, pp. 1194-1195, Nov. 2008.
Uray T, Malzer R. Out-of-hospital surface cooling to induce mild hypothermia in human cardiac arrest: A feasibility trial. Resuscitation. Jun. 2008;77(3):331-338.
Valvano, J. Bioheat Transfer published in Webster JG (Ed). Encyclopedia of Medical Devices and Instrumentation, John Wiley Publisher, 2006.
Vanden Hoek TL, Kasza KE, Beiser DG, Abella BS, Franklin JE, Oras JJ, et al. Induced hypothermia by central venous infusion: saline ice slurry versus chilled saline. Critical Care Medicine. Sep. 2004;32(9 Suppl):S425-431.
Varon J, Acosta P, Wintz R, Mendoza N. Unusual side effect from hydrogel pads during therapeutic hypothermia. Resuscitation. Sep. 2008;78(3):248-249.
Varon J, Acosta P. Therapeutic hypothermia use among health care providers in 2 developing countries. The American Journal of Emergency Medicine. Feb. 2008;26(2):244.
Varon J, Acosta P. Therapeutic hypothermia: past, present, and future. Chest. May 2008;133(5):1267-1274.
Varon J, Marik PE. Complete neurological recovery following delayed initiation of hypothermia in a victim of warm water near-drowning. Resuscitation. Mar. 2006;68(3):421-423.

(56) References Cited

OTHER PUBLICATIONS

Varon J. Therapeutic hypothermia and the need for defibrillation: wet or dry? The American Journal of Emergency Medicine. May 2007;25(4):479-480.
Varon J. Therapeutic hypothermia in cardiac arrest: 206 years later! Resuscitation [Internet]. Oct. 5, 2009 [cited Oct. 10, 2009];Available from: http://www.ncbi.nlm.nih.gov/pubmed/19811867.
Vassiliades TA, Nielsen JL, Lonquist JL. Evaluation of a new temperature management system during off-pump coronary artery bypass. Interactive Cardiovascular And Thoracic Surgery. Dec. 2003;2(4):454-457.
Villar J, Slutsky AS. Effects of induced hypothermia in patients with septic adult respiratory distress syndrome. Resuscitation. Oct. 1993;26(2):183-192.
Virkkunen I, Yli-Hankala A, Silfvast T. Induction of therapeutic hypothermia after cardiac arrest in prehospital patients using ice-cold Ringer's solution: a pilot study. Resuscitation. Sep. 2004;62(3):299-302.
Wadhwa A et al, New circulating-water devices warm more quickly than forced-air in volunteers, Technology, Computing, and Simulation, vol. 105, No. 6, Dec. 2007.
Walker G, Williams R, Condon RE, et al. Gastric Cooling in the Treatment of Bleeding from Oesophageal Varices. Lancet. Aug. 15, 1964;2(7355):328-331.
Wangensteen OH, Salmon PA, Griffen WO, Paterson JR, Fattah F. Studies of local gastric cooling as related to peptic ulcer. Annals of Surgery. Sep. 1959;150:346-360.
Weirich TL. Hypothermia/warming protocols: why are they not widely used in the OR? AORN Journal. Feb. 2008;87 (2):333-44.
Weis J, Covaciu L, Rubertsson S, Allers M, Lunderquist A, Ahlström H. Noninvasive monitoring of brain temperature during mild hypothermia. Magn Reson Imaging. Sep. 2009;27(7):923-932.
Wenner M, Freezing the heart to save life, http:/www.popsi.com/node/31512 (Jan. 29, 2009).
Wenner M, Cold relief, http:/www.popsi.com (Feb. 2009).
Whiffield AM, Coote S, Ernest D. Induced hypothermia after out-of-hospital cardiac arrest: one hospital's experience. Crit Care Resusc. Jun. 2009;11(2):97-100.
Wilkinson DJ. Cool heads: ethical issues associated with therapeutic hypothermia for newborns. Acta Paediatr [Internet]. Nov. 28, 2008;Available from: http://www.ncbi.nlm.nih.gov/entrez/query.fcgi?cmd=Retrieve&db=PubMed&dopt=Citation&list_uids=19046345.
Williams GR, Spencer FC. The clinical use of hypothermia following cardiac arrest. Annals of Surgery. Sep. 1958;148 (3):462-468.
Winfree CH, Baker KZ, Connollly ES. Perioperative normothermia and surgical-wound infection. The New England Journal of Medicine. Sep. 5, 1996;335(10):749; author reply 749-50.
Winslow R, Heart beat: how ice can save your life—'therapeutic hypothermia' can protect the brain in the aftermath of cardiac arrest, Wall Street Journal (Eastern edition) New York, N.Y.: Oct. 6, 2009, p. D.1.
Wolff B, Machill K, Schumacher D, et al. Early achievement of mild therapeutic hypothermia and the neurologic outcome after cardiac arrest. International Journal of Cardiology. Apr. 3, 2009;133(2):223-228.
Wolfrum S, Radke PW, Pischon T, Willich SN, Schunkert H, Kurowski V. Mild therapeutic hypothermia after cardiac arrest—A nationwide survey on the implementation of the ILCOR guidelines in German intensive care units. Resuscitation Nov. 9, 2006; [Internet]. Available from: http://www.ncbi.nlm.nih.gov/entrez/query.fcgi?cmd=Retrieve&db=PubMed&dopt=Citation&list_uids=17097795.
Wu ET, Huang SC, Chi NH, Lin MT, Ko WJ, Wang SS, et al. Idioventricular rhythm induced by therapeutic hypothermia. Resuscitation. Mar. 2008;76(3):471-473.
Wu X, Kochanek PM, Cochran K, Nozari A, Henchir J, Stezoski SW, et al. Mild hypothermia improves survival after prolonged, traumatic hemorrhagic shock in pigs. The Journal of Trauma. Aug. 2005;59(2):291-9; discussion 299-301.
Wu X, Stezoski J, Safar P, Nozari A, Tisherman SA. After spontaneous hypothermia during hemorrhagic shock, continuing mild hypothermia (34 degrees C) improves early but not late survival in rats. The Journal of Trauma. Aug. 2003;55(2):308-316.
Xiao H, Remick DG. Correction of perioperative hypothermia decreases experimental sepsis mortality by modulating the inflammatory response. Critical Care Medicine. Jan. 2005;33(1):161-167.
Yahagi N, Kumon K, Watanabe Y, Tanigami H, Haruna M, Hayashi H, et al. Value of mild hypothermia in patients who have severe circulatory insufficiency even after intra-aortic balloon pump. Journal of Clinical Anesthesia. Mar. 1998;10 (2):120-125.
Yanagawa Y, Indications and limitations of induced hypothermic therapy for out-of-hospital cardiopulmonary arrest, American Journal of Emergency Medicine (2006) 24, 214-216.
Young GB. Neurologic Prognosis after Cardiac Arrest. N Engl J Med. Aug. 6, 2009;361(6):605-611.
Zeiner A, Holzer M, Sterz F, et al. Mild resuscitative hypothermia to improve neurological outcome after cardiac arrest. A clinical feasibility trial. Hypothermia After Cardiac Arrest (HACA) Study Group. Stroke; A Journal of Cerebral Circulation. Jan. 2000;31(1):86-94.
Zhang H, Zhou M, Zhang J, Mei Y, Sun S, Tong E. Therapeutic effect of post-ischemic hypothermia duration on cerebral ischemic injury. Neurological Research. May 2008;30(4):332-336.
Zoler ML, Hypothermia makes gains in cardiac arrest, American College of Emergency Physicians, Feb. 2009.
Zweifler RM, Induction and maintenance of mild hypothermia by surface cooling in non-intubated subjects, Journal of Stroke and Cerebrovascular Diseases, vol. 12, No. 5 Sep.-Oct. 2003: pp. 237-243.
Klurisu, et al., Therapeutic Hypothermia After Out-of-Hospital Cardiac Arrest Due to Brugada Syndrome, Resuscitation (2008) 79, 332-335.
Safar, Peter J.—Obituary, Resuscitation (2003) 59, 3-5.
Morley—Worksheet for evidence—Based Review of Hypothermia . . . , Induced hypothermia Apr. 2006, pp. 1-14 (on-line background material supporting the recommendations of the AHA).
2010 American Heart Association Guidelines for Cardiopulmonary Resuscitation and Emergency Cardiovascular Care Part 1—Executive Summary.
Holt et al., Internal Cooling for General Hypothermia, Internal cooling—Hypothermia, vol. 87, 471-474 (1963).
Zhao J, Luo AL, Xu L, Huang YG. Forced-air warming and fluid warming minimize core hypothermia during abdominal surgery. Chinese medical sciences journal = Chung-kuo i hsueh k'o hsueh tsa chih / Chinese Academy of Medical Sciences. 2005;20(4)261-4.
Otteni JC, Kohler JJ, Gillet M. [New technic of moderate gastric hypothermia: direct lavage of the stomach with the cooling fluid]. Annales de chirurgie., 23(25):1355-1359 (Dec. 1969).
Perl T, Bräuer A, Quintel M. Prevention of perioperative hypothermia with forced-air warming systems and upper-body blankets. Surgical Technology International. 2006;15:19-22.
Polderman, Induced hypothermia and fever control for prevention and treatment of neurological injuries, Thelancet.com, vol. 371, 1955-1969 (2008).
Baranova AI, Wei EP, Ueda Y, Sholley MM, Kontos HA, Povlishock JT. Cerebral vascular responsiveness after experimental traumatic brain injury: the beneficial effects of delayed hypothermia combined with superoxide dismutase administration. Journal of neurosurgery. Sep. 2008;109(3):502-509.
Barnard CN. Hypothermia; a method of intragastric cooling. The British Journal of Surgery. Nov. 1956;44(185):296-298.
Burns SM, Bostek CC. Avoiding unintentional hypothermia: anesthesia implications. Nurse anesthesia. Sep. 1990;1 (3):128-133.
Carroll M, Beek O. Protection against hippocampal CA1 cell loss by post-ischemic hypothermia is dependent on delay of initiation and duration. Metabolic brain disease. Mar. 1992;7(1):45-50.
Cushman WF, DeMaio JT. Experience With Local Gastric Cooling. AMA Arch Surg. Oct. 1, 1964 1964;89 (4):719-724.
Dunn JE, Williams LF. Esophageal Cooling as a Technic of Selective Brain Hypothermia. Techn Docum Rep Sam-Tdr-63-19. Technical documentary report. United States. Air Force. Systems Command. Apr. 1963;94:1-7.

(56) References Cited

OTHER PUBLICATIONS

Frank SM, Fleisher LA, Breslow MJ, et al. Perioperative maintenance of normothermia reduces the incidence of morbid cardiac events. A randomized clinical trial. Jama. Apr. 9, 1997;277(14)1127-34.
Gendron F. "Burns" occurring during lengthy surgical procedures. Journal of clinical Engineering. Jan.-Mar. 1980;5 (1):19-26.
Griffen WO, Salmon PA, Castaneda A, Nicoloff D, Wangensteen OH. Local gastric hypothermia in the treatment of massive upper gastrointestinal hemorrhage. With a discussion of techniques. Minnesota Medicine. May 1960;43:299-305.
Holt MH, Benvenuto R, Lewis EJ. General hypothermia with intragastric cooling. Surgery, gynecology & obstetrics. Aug. 1958;107(2)251-254.
Holt MH, Benvenuto R, Lewis FJ. General hypothermia with intragastric cooling: a further study. Surgical forum. 1958;9:287-91.
Jones DA. Management of cardiac arrest patients in the ICU: is keeping a cool head the standard of care? Crit Care Resusc. Jun. 2009;11(2):91-93.
Kapp DS, Prionas SD, Fessenden P, Liu FF, Lee ER, Lohrbach AW. Bladder cooling in patients treated with regional hyperthermia of the pelvis using an annular phased array. International journal of radiation oncology, biology, physics. Jun. 1988;14(6):1307-10.
Kimberger O, Kurz A. Thermoregulatory management for mild therapeutic hypothermia. Best Practice & Research. Dec. 2008;22(4):729-744.
Kuboyama K, Safar P, Radovsky A, Tisherman SA, Stezoski SW, Alexander H. Delay in cooling negates the beneficial effect of mild resuscitative cerebral hypothermia after cardiac arrest in dogs: a prospective, randomized study. Critical Care Medicine. Sep. 1993;21(9)1348-58.
Mackensen GB, McDonagh DL, Warner DS. Perioperative Hypothermia: Use and Therapeutic Implications. Journal of Neurotrauma. 2009 3;26(3)342-358.
Yu CG, Jimenez O, Marcillo AE, Weider B, Bangerter K, Dietrich WD, et al. Beneficial effects of modest systemic hypothermia on locomotor function and histopathological damage following contusion-induced spinal cord injury in rats. Journal of neurosurgery. Jul. 2000;93(1 Suppl):85-93.
Montanini S, Martinelli G, Torri G, Berti M, Pattono R, Borzomati E, et al. [Recommendations on perioperative hormothermia. Working Group on Perioperative Hypothermia, Italian Society for Anesthesia, Analgesia, Resuscitation, and Intensive Care]. Minerva anestesiologica. Mar. 2001;67(3):157-8.
Moretti B, Larocca AMV, Napoli C, Martinelli D, Paolillo L, Cassano M, et al. Active warming systems to maintain perioperative normothermia in hip replacement surgery: a therapeutic aid or a vector of infection? J. Hosp. Infect. Sep. 2009;73(1):58-63.
Morley-Forster PK. Unintentional hypothermia in the operating room. Canadian Anaesthetists' Society Journal. Jul. 1986;33(4):515-528.
Nesher N, Insler SR, Sheinberg N, Bolotin G, Kramer A, Sharony R, et al. A new thermoregulation system for maintaining perioperative normothermia and attenuating myocardial injury in off-pump coronary artery bypass surgery. The heart surgery forum. 2002;5(4):373-80.
Nichols R, Zawada E. A case study in therapeutic hypothermia treatment post-cardiac arrest in a 56-year-old male. S D Med. Oct. 2008;61(10):371-373.
Nicoloff DM, Griffen WO, Salmon PA, Peter ET, Wangensteen OH. Local gastric hypothermia in the management of massive gastrointestinal hemorrhage. Surgery, gynecology & obstetrics. Apr. 1962;114:495-503.
Perey BJ, Helle SJ, Maclean LD. Acute Alcoholic Poisoning: a Complication of Gastric Hypothermia. Canadian journal of surgery. Apr. 1965;8:194-196.
Safar P. Resuscitation from clinical death: pathophysiologic limits and therapeutic potentials. Crit Care Med. Oct. 1988;16(10):923-941.
Salmon PA, Griffen WO, Wangensteen OH. Effect of intragastric temperature changes upon gastric blood flow. Proceedings of the Society for Experimental Biology and Medicine. Society for Experimental Biology and Medicine (New York, N.Y. Jul. 1959;101(3):442-4444.
Sandler JL, Ballinger WF, Medoff JL. Gastric hypothermia induced by gastric lavage without a balloon. Surgery, gynecology & obstetrics. 1960;111:784-5.
Skulec R, Truhlár A, Ostádal P, Telekes P, Knor J, Tichácek M, et al. [Current cooling methods for induction of mild hypothermia in cardiac arrest survivors]. Vnitr Lek. Nov. 2009;55(11):1060-1069.
Steib A, Beller JP, von Bandel M, Beck F, Chabrol JL, Otteni JC. Oesophageal thermal tube for intraoperative hypothermia in liver transplantation. Acta Anaesthesiol Scand. Feb. 1993;37(2):199-202.
Stetson JB. Unintentional hypothermia in the operating room: a footnote. Canadian Journal of Anaesthesia—Journal Canadien D'anesthesie. Mar. 1988;35(2):206-208.
Tokutomi T, Morimoto K, Miyagi T, Yamaguchi S, Ishikawa K, Shigemori M. Optimal temperature for the management of severe traumatic brain injury: effect of hypothermia on intracranial pressure, systemic and intracranial hemodynamics, and metabolism. Neurosurgery. Jul. 2007;61(1 Suppl):256-265; discussion 265-256.
Wangensteen SL. Intragastric cooling for upper gastrointestinal hemorrhage. The Surgical Clinics of North America. Oct. 1962;42:1171-1180.
Waterman NG, Walker JL. The effect of gastric cooling on hemostasis. Surgery, Gynecology & Obstetrics. Jul. 1973;137(1):80-82.
Wolff B, Machill K, Schumacher D, et al. Early achievement of mild therapeutic hypothermia and the neurologic outcome after cardiac arrest. International journal of cardiology. Mar. 17, 2008.
Xu H, Luo J, Huang F. [Clinical study on effect of keeping perioperative normal body temperature on skin flap survival]. Zhongguo Xiu Fu Chong Jian Wai Ke Za Zhi. Jul. 2007;21(7):718-721.
Young VL, Watson ME. Prevention of perioperative hypothermia in plastic surgery. Aesthetic surgery journal / the American Society for Aesthetic Plastic surgery. Sep.-Oct. 2006;26(5):551-571.
Nagao K, Kikushima K, Watanabe K, Tachibana E, Tominaga Y, Tada K, et al. Early Induction of Hypothermia During Cardiac Arrest Improves Neurological Outcomes in Patients With Out-of-Hospital Cardiac Arrest Who Undergo Emergency Cardiopulmonary Bypass and Percutaneous Coronary Intervention. Circ. J [Internet]. Nov. 27, 2009 [cited Nov. 28, 2009];Available from: http://www.ncbi.nlm.nih.gov/pubmed/19942784.
Danelli G, Berti M, Perotti V, Albertin A, Baccari P, Deni F, et al. Temperature control and recovery of bowel function after laparoscopic or laparotomic colorectal surgery in patients receiving combined epidural/general anesthesia and postoperative epidural analgesia. Anesthesia and analgesia. Aug. 2002;95(2):467-471, table of contents.
Dohi R, Andres RH, Steinberg GK, Guzman R. Intraoperative hypothermia during vascular neurosurgical procedures. Neurosurg Focus. May 2009;26(5):E24.
Eisenburger P. Sterz F, Holzer M, Zeiner A, Scheinecker W, Havel C, et al. Therapeutic hypothermia after cardiac arrest. Curr Opin Crit Care. Jun. 2001;7(3):184-188.
Fisher GC. Hypothermia after cardiac arrest: feasible but is it therapeutic? Anaesthesia. Aug. 2008;63(8):885-886; author reply 886.
Foex BA, Butler J. Best evidence topic report. Therapeutic hypothermia after out of hospital cardiac arrest. Emerg Med J. Sep. 2004;21(5):590-591.
Kempen PM. Perioperative normothermia and surgical-wound infection. The New England Journal of Medicine. 1996;335(10):747-8; author reply 749-50.
Miller RE, Moscarella AA, Fitzpatrick HF. Local Gastric Hypothermia. AMA Arch Surg. Feb. 1, 1963 1963;86(2):272-275.
Moss G. Iced saline lavage for stomach hemorrhage. Rn. Jun. 1972;35(6):ICU1-2.
Nolan JP, Neumar RW, Adrie C, et al. Post-cardiac arrest syndrome: Epidemiology, pathophysiology, treatment, and prognostication A Scientific Statement from the International Liaison Committee on Resuscitation; the American Heart Association Emergency Cardio-

(56) References Cited

OTHER PUBLICATIONS vascular Care Committee; the Council on Cardiovascular Surgery and Anesthesia; the Council on Cardiopulmonary, Perioperative, and Critical Care; the Council on Clinical Cardiology; the Council on Stroke. Resuscitation. Dec. 2008;79(3):350-379.

Wangensteen OH, Root HD, Jenson CB, Imamoglu K, Salmon PA. Depression of gastric secretion and digestion by gastric hypothermia: its clinical use in massive hematemesis. Surgery. Aug. 1958;44(2):265-274.

Scott SM. Thermal blanket injury in the operating room. Arch Surg. Feb. 1967;94(2):181.

Wu X, Drabek T, Kochanek PM, Henchir J, Stezoski SW, Stezoski J, et al. Induction of profound hypothermia for emergency preservation and resuscitation allows intact survival after cardiac arrest resulting from prolonged lethal hemorrhage and trauma in dogs. Circulation. Apr. 25, 2006;113(16):1974-1982.

Rossotto P, Motta G, Ferr Aris R. [Local gastric and gastroesophageal hypothermia. Description of a new model machine and of special tubes for intravisceral cooling]. Minerva chirurgica. Mar. 30, 1963;18:267-272.

Wolfrum S, Pierau C, Radke PW, et al. Mild therapeutic hypothermia in patients after out-of-hospital cardiac arrest due to acute ST-segment elevation myocardial infarction undergoing immediate percutaneous coronary intervention. Crit Care Med. Jun. 2008;36(6):1780-1786.

Society of Critical Care Medicine—Endorsed Guidelines [Internet]. Jun. 16, 2009; Available from: http://www.learnicu.org/Quick_Links/Pages/default.aspx#clinguide.

Paradis N, Halperin H. Cardiac Arrest: The Science and Practice of Resuscitation Medicine. Cambridge University Press; 2007. (Book).

Clifton GL et al., Lack of effect of induction of hypothermia after acute brain injury, N Engl J of Med, vol. 344, No. 8 Feb. 22, 2001 pp. 556-563.

Colbourne F, Corbett D, Zhao Z, et al. Prolonged but delayed postischemic hypothermia: a long-term outcome study in the rat middle cerebral artery occlusion model. J Cereb Blood Flow Metab. Dec. 2000;20(12):1702-1708.

Colbourne F, Corbett D. Delayed postischemic hypothermia: a six month survival study using behavioral and histological assessments of neuroprotection. J Neurosci. Nov. 1995;15(11):7250-7260.

Collins TJ et al, Therapeutic hypothermia following cardiac arrest: A review of the evidence, British Assoc. of Critical Care Nurses, Nursing in Critical Care (2008) vol. 12, No. 3, pp. 144-51.

Cooke RP, Catchpole M. Maintaining perioperative normothermia: forced air warming devices require risk assessments before use. BMJ (Clinical Research Ed. Jun. 28, 2003;326(7404):1457.

Cordoba J, Crespin J, Gottstein J, et al. Mild hypothermia modifies ammonia-induced brain edema in rats after portacaval anastomosis. Gastroenterology. Mar. 1999;116(3):686-693.

Corry JJ, Dhar R, Murphy T, Diringer MN. Hypothermia for refractory status epilepticus. Neurocritical Care. 2008;9 (2):189-97.

Craig JD, Tompkin AM. Gastric Hypothermia. Lancet. Feb. 27, 1965;1(7383):493.

Crino MH, Nagel EL. Thermal burns caused by warming blankets in the operating room. Anesthesiology. Jan.-Feb. 1968;29(1):149-150.

Cummins RO et al, Recommended guidelines for uniform reporting of data from out-of-hospital cardiac arrest: The Utstein style, AHA Medical/Scientific Statement, vol. 84, No. 2, Aug. 1991, pp. 960-975.

Darby JM et al, Therapeutic Hypothermia after cardiac arrest, The New England Journal of Medicine, vol. 347, No. 1 (Jul. 4, 2002) pp. 63-70.

Davies AR. Hypothermia improves outcome from traumatic brain injury. Crit Care Resusc. Sep. 2005;7(3):238-243.

De Jong et al, The pituitary-ardrenal axis is activated more in non-survivors than in survivors of cardiac arrest, irrespective of therapeutic hypothermia, Resuscitation (2008) 78(8):281-88.

de Smet, AM et al, Decontamination of the digestive tract and oropharynx in ICU patients, The New England Journal of Medicine (2009) 360:20-31.

De Vreede-Swagemakers JJ, Gorgels AP, Dubois-Arbouw WI, van Ree JW, Daemen MJ, Houben LG, et al. Out-of-hospital cardiac arrest in the 1990's: a population-based study in the Maastricht area on incidence, characteristics and survival. Journal of the American College of Cardiology. Nov. 15, 1997;30(6):1500-1505.

De Witte J et al, Perioperative shivering, Anesthesiology, vol. 96, No. 2, Feb. 2002.

Dichtwald S, Matot I, Einav S. Improving the outcome of in-hospital cardiac arrest: the importance of being EARNEST. Seminars in Cardiothoracic and Vascular Anesthesia. Mar. 2009;13(1):19-30.

Dietrich WD, 3rd. Therapeutic hypothermia for spinal cord injury. Crit Care Med. Jul. 2009;37(7 Suppl):S238-242.#1.

Dietrich WD, Atkins CM, Bramlett HM. Protection in Animal Models of Brain and Spinal Cord Injury with Mild to Moderate Hypothermia. Journal of Neurotrauma. 2009 3;26(3):301-312. #2.

Dietrich DW, Kuluz Jw. New research in the field of stroke: therapeutic hypothermia after cardiac arrest. Stroke; a Journal of Cerebral Circulation. Apr. 2003;34(4):1051#3.

Dietrich WD et al, Introduction. Journal of Neurotrauma. (Mar. 2009) DOI 10.1089/neu.2009.9958.

Dohi K, Jimbo H, Abe T, Aruga T. Positive selective brain cooling method: a novel, simple, and selective nasopharyngeal brain cooling method. Acta Neurochirurgica. 2006;96:409-412.

Doll H et al, Pharyngeal selective brain cooling improves neurofunctional and neurocognitive outcome after fluid percussion brain injury in rats, Journal of Neurotrauma 26:1-8 (Feb. 2009).

Don C, Longstreth W, Maynard C, Olsufka M, Nichol G, Ray T, et al. Active surface cooling protocol to induce mild therapeutic hypothermia after out-of-hospital cardiac arrest: A retrospective before-and-after comparison in a single hospital*. Crit. Care Med. [Internet]. Sep. 16, 2009 [cited Sep. 26, 2009];Available from: http://www.ncbi.nlm.nih.gov/pubmed/19770738.

Marion DW, Leonov Y, Ginsberg M, et al. Resuscitative hypothermia. Crit Care Med. Feb. 1996;24(2 Suppl):S81-89.

Doufas AG. Consequences of inadvertent perioperative hypothermia. Best Practice & Research. Dec. 2003;17(4):535-549.

Dripps RD. The physiology of induced hypothermia: proceedings of a symposium, Oct. 28-29, 1955. National Academy of Sciences. Washington, DC; 1956.

Engelhart K, The cooling cure, Maclean's (Aug. 2009) Toronto, vol. 122 lss. 33 p. 38.

Arizant Healthcare Inc. Fact sheet: the dangers of "hosing"; available at www.stophosing.com (Accessed Jun. 2009).

Fanelli A, Danelli G, Ghisi D, Ortu A, Moschini E, Fanelli G. The efficacy of a resistive heating under-patient blanket versus a forced-air warming system: a randomized controlled trial. Anesth. Analg. Jan. 2009;108(1):199-201.

Felies M, Poppendieck S, Nave H. Perioperative normothermia depends on intraoperative warming procedure, extent of the surgical intervention and age of the experimental animal. Life sciences. Nov. 4, 2005;77(25):3133-3140.

Ferreira I, Schutte M, Oosterloo E, Dekker W, Mooi BW, Dambrink JHE, et al. Therapeutic mild hypothermia improves outcome after out-of-hospital cardiac arrest. Neth Heart J. Oct. 2009;17(10):378-384.

Fingas M, Penner M, Silasi G, Colbourne F. Treatment of intracerebral hemorrhage in rats with 12 h, 3 days and 6 days of selective brain hypothermia. Exp. Neurol. Sep. 2009;219(1):156-162.

Fink E, Clark R, Kochanek P, Bell M, Watson R. A tertiary care center's experience with therapeutic hypothermia after pediatric cardiac arrest. Pediatr Crit Care Med [Internet]. Nov. 23, 2009 [cited Nov. 28, 2009];Available from: http://www.ncbi.nlm.nih.gov/pubmed/19935440.

Fink K, Schwab T, Bode C, Busch HJ. [Endovascular or surface cooling?: therapeutic hypothermia after cardiac arrest]. Der Anaesthesist. Dec. 2008;57(12):1155-1160.

Fleisher, et al., "ACC/AHA 2007 Guidelines on Perioperative Cardiovascular Evaluation and Care for Noncardiac Surgery: Execu-

(56) References Cited

OTHER PUBLICATIONS tive Summary," Journal of the American College of Cardiology, Oct. 2007, vol. 50, No. 17, pp. 1707-1732.
Forbes SS, Eskicioglu C, Nathens AB, Fenech DS, Laflamme C, McLean RF, et al. Evidence-based guidelines for prevention of perioperative hypothermia. J. Am. Coll. Surg. Oct. 2009;209(4):492-503.e1.
Frank SM, Beattie C, Christopherson R, Norris EJ, Perler BA, Williams GM, et al. Unintentional hypothermia is associated with postoperative myocardial ischemia. The Perioperative Ischemia Randomized Anesthesia Trial Study Group. Anesthesiology. Mar. 1993;78(3):468-476.
Freeman WD, Barrett KM, Freeman ML, Johnson M, Divertie G, Rossetti AO, et al. Predictors of awakening from postanoxic status epilepticus after therapeutic hypothermia. Neurology. Nov. 3, 2009;73(18):1512; author reply 1512-1513.
Friberg H, Nielsen N. Hypothermia after Cardiac Arrest: Lessons Learned from National Registries. Journal of Neurotrauma. Mar. 2009;26(3):365-369.
Fujimoto K, Fujita M, Tsuruta R, Tanaka R, Shinagawa H, Izumi T, et al. Early induction of moderate hypothermia suppresses systemic inflammatory cytokines and intracellular adhesion molecule-1 in rats with caerulein-induced pancreatitis and endotoxemia. Pancreas. Aug. 2008;37(2):176-81.
Fukudome EY, Alam HB. Hypothermia in multisystem trauma. Critical Care Medicine. Jul. 2009;37(7 Suppl):S265-272.
Fuller ET, Milling TJ, Jr., Price B, et al. Therapeutic hypothermia in cocaine-induced cardiac arrest. Annals of Emergency Medicine. Feb. 2008;51(2):135-137.
Gaieski DF et al, Early goal-directed hemodynamic optimization combined with terapeutic hypothermia in comatose survivors of out-of-hospital cardiac arrest, Resuscitation 3838 (2009).
Gali B, Findlay JY, Plevak DJ. Skin injury with the use of a water warming device. Anesthesiology. Jun. 2003;98(6):1509-1510.
Geocadin RG, Understanding and enhancing functional outcomes after cardiac arrest: The need for a multidisciplinary approach to refocus on the brain, Resuscitation (2009) 80, 153-154.
Georgiadis D, Schwarz S, Kollmar R, et al. Endovascular cooling for moderate hypothermia in patients with acute stroke: first results of a novel approach. Stroke; A Journal of Cerebral Circulation. Nov. 2001;32(11):2550-2553.
Giesbrecht GG et al, Comparison of forced-air patient warming systems for perioperative use, Anesthesiology, vol. 80, No. 3, pp. 671-679 (Mar. 1994).
Greer DM, Funk SE, Reaven NL, Ouzounelli M, Uman GC. Impact of fever on outcome in patients with stroke and neurologic injury: a comprehensive meta-analysis. Stroke; A Journal of Cerebral Circulation. 2008;39(11):3029-3035.
Bräuer A, Weyland W. Oesophageal heat exchanger in the prevention of perioperative hypothermia. Acta Anaesthesiol Scand. Nov. 1998;42(10):1232-1233.
Kimberger O, et al, Resistive polymer versus forced-air warming: comparable heat transfer and core rewarming rates in volunteers, International Anesthesia Research Society, vol. 107, No. 5, Nov. 2008, pp. 1621-1626.
Kimberger et al., Accuracy and Precision of a Novel Non-Invasive Core ThermometerBritish Journal of Anaesthesia 2009.
Kirkland KB, Briggs JP, Trivette SL, Wilkinson WE, Sexton DJ. The impact of surgical-site infections in the 1990s: attributable mortality, excess length of hospitalization, and extra costs. Infect Control Hosp Epidemiol. Nov. 1999;20 (11):725-730.
Kirkland LL, Parham WM, Pastores SM. Approaching hospital administration about adopting cooling technologies. Crit Care Med. Jul. 2009;37(7 Suppl):S290-294.
Kirkpatrick AW, Chun R, Brown R, et al. Hypothermia and the trauma patient. Can. J. of Surg. Oct. 1999;42 (5):333-343. (English abstract only).

Kliegel A, Janata A, Wandaller C, et al. Cold infusions alone are effective for induction of therapeutic hypothermia but do not keep patients cool after cardiac arrest. Resuscitation. Apr. 2007;73(1):46-53.
Knafelj R, Radsel P, Ploj T, Noc M. Primary percutaneous coronary intervention and mild induced hypothermia in comatose survivors of ventricular fibrillation with ST-elevation acute myocardial infarction. Resuscitation. Aug. 2007;74 (2):227-34.
Kochanek PM, Drabek T, Tisherman SA. Therapeutic Hypothermia: The Safar Vision. Journal of Neurotrauma, 2009 3;26(3):417-420.
Kochanek PM, Fink EL, Bell MJ, Bayir H, Clark RS. Therapeutic Hypothermia: Applications in Pediatric Cardiac Arrest. Journal of Neurotrauma. 2009 3;26(3):421-427.
Kochanek PM, Safar PJ. Therapeutic hypothermia for severe traumatic brain injury. Jama. Jun. 11, 2003;289 (22):3007-9.
Kochanek PM et al, Bakken Lecture: The brain, the heart, and therapeutic hypothermia, Cleveland Clinical Journal of Medicine, vol. 76 (Suppl 2) Apr. 2009.
Kollmar R, Schwab S. Hypothermia in Focal Ischemia: Implications of Experiments and Experience. Journal of Neurotrauma. 2009 3;26(3):377-386.
Kory PD et al, Induction of mild therapeutic hypothermia (MTH): description of a rapid and inexpensive technique in the post-arrest patient, Chest (2007) 446S.
Krawczyk P, Fraczek B, Drab E. Use of therapeutic hypothermia in Polish intensive care units. Resuscitation. Nov. 2008;79(2):339.
Krieger DW. Steeplechase in emergency medical care: cooling for cardiac arrest. Stroke; A Journal of Cerebral Circulation. Jul. 2006;37(7):1638-1639.
Kristensen G et al, Simple system for central rewarming of hypothermic patients, The Lancet, Dec. 20/27, 1986 pp. 1467-1468.
Kristensen G et al, Prevention of peroperative hypothermia in abdominal surgery, Acta Anaesthesiol Scand 1986:30:314-316.
Kristensen et al., An Oesophageal Thermal Tube for Rewarming in Hypothermia, Acta Anaesthesiol Scand 1985:29:846-848.
Kubli S, Hypothermia after cardiac arrest: feasible but is it therapeutic? Anaesthesia, 2008; 63; 889-895.
Kulkarni P et al, Body heat transfer during hip surgery using active core warming Can J Anaesth 1995/42:7/pp. 571-576.
Kumar S, Wong PF, Melling AC, Leaper DJ. Effects of perioperative hypothermia and warming in surgical practice. International Wound Journal. Sep. 2005;2(3):193-204.
Kupchik NL. Development and implementation of a therapeutic hypothermia protocol. Critical Care Medicine. Jul. 2009;37(7 Suppl):S279-84.
Kuehn BM, Safer therapies for newborns probed, JAMA 2009; 301(1):25.
Kurusz M, Temperature management during cardiopulmonary bypass, doi:10.1053/j.jvca.2009.06.016.
Kurz A, Sessler DI, Lenhardt R. Perioperative normothermia to reduce the incidence of surgical-wound infection and shorten hospitalization. Study of Wound Infection and Temperature Group. The New England Journal of Medicine. May 9, 1996;334(19):1209-1215.
Kwon BK, Mann C, Sohn HM, Hilibrand AS, Phillips FM, Wang JC, et al. Hypothermia for spinal cord injury. Spine J. Nov.-Dec. 2008;8(6):859-74.
Laupland KB. Fever in the critically ill medical patient. Critical Care Medicine. Jul. 2009;37(7 Suppl):S273-8.
Laver SR, Padkin A, Atalla A, Nolan JP. Therapeutic hypothermia after cardiac arrest: a survey of practice in intensive care units in the United Kingdom. Anaesthesia. Sep. 2006;61(9):873-877.
Ledingham I. McA, Central Rewarming System For Treatment of Hypothermia, The Lancet, May 31, 1980.
Laish-Farkash A et al, Therapeutic hypothermia for comatose survivors after cardiac arrest, Israeli Med. Assoc'n. Journal, Apr. 2007, vol. 9, pp. 252-256.
Leather RA, Sullivan SN. Iced gastric lavage: a tradition without foundation. Cmaj. Jun. 15, 1987;136(12):1245-1247.
Lequerica JL et al, Reliability assessment of a cooled intraesophageal balloon to prevent thermal injury during RF cardiac oblation: an Agar Phantom study, Journal of Cardiovascular Electrophysiology, vol. 19, No. 11, Nov. 2008, 1188-1193.

(56) References Cited

OTHER PUBLICATIONS

Levi AD, Green BA, Wang MY, Dietrich WD, Brindle T, Vanni S, et al. Clinical Application of Modest Hypothermia after Spinal Cord Injury. Journal of Neurotrauma. Mar. 3, 2009;26(3):407-415.

Levitt MA, Kane V, Henderson J, Dryjski M. A comparative rewarming trial of gastric versus peritoneal lavage in a hypothermic model. The American Journal of Emergency Medicine. Jul. 1990;8(4):285-288.

Linares G, Mayer SA. Hypothermia for the treatment of ischemic and hemorrhagic stroke. Critical Care Medicine. Jul. 2009;37(7 Suppl):S243-9.

Loscher W, Cole AJ, McLean MJ. Commentary: physical approaches for the treatment of epilepsy: electrical and magnetic stimulation and cooling. Neurotherapeutics. Apr. 2009;6(2):258-262.

Lyon et al, Therapeutic hypothermia in the emergency department following out-of-hospital cardiac arrest, Emerg. Med. J. (2010) 27:418-423.

MacLellan CL, Clark DL, Silasi G, Colbourne F. Use of Prolonged Hypothermia to Treat Ischemic and Hemorrhagic Stroke. Journal of Neurotrauma. 2009 3;26(3):313-323.

Mahmood MA, Zweifler RM. Progress in shivering control. Journal of the Neurological Sciences. Oct. 15, 2007;261 (1-2):47-54.

Mahoney CB, Odom J. Maintaining intraoperative normothermia: a meta-analysis of outcomes with costs. AANA Journal. Apr. 1999;67(2):155-63.

Majersik JJ, Silbergleit R, Meurer WJ, Brown DL, Lisabeth LD, Morgenstern LB. Public health impact of full implementation of therapeutic hypothermia after cardiac arrest. Resuscitation. May 2008;77(2):189-194.

Marion D, Bullock MR. Current and Future Role of Therapeutic Hypothermia. Journal of Neurotrauma. Mar. 3, 2009;26 (3):455-467.

Marion DW, Penrod LE, Kelsey SF, et al. Treatment of traumatic brain injury with moderate hypothermia. N Engl J Med. Feb. 20, 1997;336(8):540-546.

Martinek M et al, Esophageal damage during radiofrequency ablation of atrial fibrillation: Impact of energy settings, lesion sets, and esophageal visualization, Journal of Cardiovascular Electrophysiology (2008) pp. 1-8.

Mason OS, Influence of a forced air warming system on morbidly obese patients undergoing Roux-en-Y gastric bypass, Obesity Surgery, 8:453-460 (1998).

Mathias JM. ORs on board with warming protocols. OR Manager. Dec. 2006;22(12):17.

Matsuzaki Y, Matsukawa T, Ohki K, Yamamoto Y, Nakamura M, Oshibuchi T. Warming by resistive heating maintains perioperative normothermia as well as forced air heating. British Journal of Anaesthesia. May 2003;90(5):689-91.

Mavrogordato AE, Wagstaff MJD, Fletcher AJP, Wilson DI, Jayamaha JEL. A novel method to treat hyperthermia in a burns case: use of a catheter-based heat exchange system. Burns. Feb. 2009;35(1):141-145.

Mayer SA, Kowalski RG, Presciutti M, Ostapkovich ND, McGann E, Fitzsimmons B, et al. Clinical trial of a novel surface cooling system for fever control in neurocritical care patients. Crit. Care Med. Dec. 2004;32(12):2508-2515.

McIlrath DC, Hallenbeck GA, Allen HA, Mann CV, Baldes EJ, Brown AL, et al. Gastric Freezing: an Experimental Study. Gastroenterology. Sep. 1963;45:374-383.

Arruda et al., *Journal of Cardiovascular Electrophysiology*, 20(11): 1272-1278 (2009).

Berjano et al., *Physics in Medicine and Biology*, 50: N269-N279 (2005).

Meloni BP, Campbell K, Zhu H, Knuckey NW. In Search of Clinical Neuroprotection After Brain Ischemia. The Case for Mild Hypothermia (35{degrees}C) and Magnesium. Stroke; A Journal of Cerebral Circulation [Internet]. Apr. 16, 2009; Available from: http://www.ncbi.nlm.nih.gov/entrez/query.fcgi?cmd=Retrieve&db=PubMed&dopt=Citation&list_uids=19372444.

Menegazzi JJ, Rittenberger JC, Suffoletto BP, Logue ES, Salcido DD, Reynolds JC, et al. Effects of pre-arrest and intra-arrest hypothermia on ventricular fibrillation and resuscitation. Resuscitation. Jan. 2009;80(1):126-32.

Merchant RM, Abella BS, Peberdy MA, Soar J, Ong ME, Schmidt GA, et al. Therapeutic hypothermia after cardiac arrest: unintentional overcooling is common using ice packs and conventional cooling blankets. Crit Care Med. Dec. 2006;34(12 Suppl):S490-494.

Merchant RM, Becker LB, Abella BS, Asch DA, Groeneveld PW. Cost-effectiveness of therapeutic hypothermia after cardiac arrest. Circ Cardiovasc Qual Outcomes. Sep. 1, 2009;2(5):421.428.

Merchant RM, Soar J, Skrifvars MB, Silfvast T, Edelson DP, Ahmad F, et al. Therapeutic hypothermia utilization among physicians after resuscitation from cardiac arrest. Critical Care Medicine. Jul. 2006;34(7):1935-40.

Merchant RM et al, Cardiac catherterization is underutilized after in-hospital cardiac arrest, Resusutation (2008).

Mermel, Clinical Practice Guidelines for the Diagnosis and Management of Intravascular Catheter-Related Infection: 2009 Update by the Infectious Diseases Society of America, CID 2009:49 (Jul. 1) 1-45.

Minambres E et al, Mild hypothermia induction after cardiac arrest using water-circulating cooling device, doi:10.1016/j.ajem.2006.12.014.

Modell JH, Gravenstein N, Morey TE. Body temperature change during anesthesia for electroconvulsive therapy: implications for quality incentives in anesthesiology. Anesthesia and Analgesia. Nov. 2008;107(5):1618-1620.

Modell JH, Idris AH, Pineda JA, et al. Survival after prolonged submersion in freshwater in Florida. Chest. May 2004;125(5):1948-1951.

Morris RH, Kumar A. The effect of warming blankets on maintenance of body temperature of the anesthetized, paralyzed adult patient. Anesthesiology. Apr. 1972:36(4):408-11.

Moss G. Technic of iced saline gastric lavage in upper gastrointestinal hemorrhage. Amer J Surg, Oct. 1971;122(4):565-6.

Mu Q et al, Thermal conductivity of silicone rubber filled with ZnO, Polymer Composites 2007, pp. 125-130.

Mynick A, Therapeutic Hypothermia in Maine: When is it Malpractice Not to Offer the Big Chill? [Internet]. Jun. 16, 2009; Available from: http://bangor-augusta.injuryboard.com/medical-malpractice/therapeutic-hypothermia-in-maine-when-is-it-malpractice-not-to-offer-the-big-chill.aspx?googleid=229996.

Neimark et al, Brain cooling maintenance with cooling cap . . . , Journal of Theoretical Biology 253 (2008) 333-344.

Nesher N, Wolf T, Uretzky G, Oppenheim-Eden A, Yussim E, Kushnir I, et al. A novel thermoregulatory system maintains perioperative normothermia in children undergoing elective surgery. Paediatric Anaesthesia. 2001;11(5):555-60.

Nesseler N, Leurent G, Seguin P, Grundmann S, Busch H, Young GB. Neurologic Prognosis after Cardiac Arrest. N Engl J Med. Nov. 12, 2009;361(20):1999-2000.

Ng SF, Oo CS, Loh KH, Lim PY, Chan YR, Ong BC. A comparative study of three warming interventions to determine the most effective in maintaining perioperative normothermia. Anesthesia and Analgesia. Jan. 2003;96(1):171-6, table of contents.

Nguyen NT, Fleming NW, Singh A, Lee SJ, Goldman CD, Wolfe BM. Evaluation of core temperature during aparoscopic and open gastric bypass. Obes Surg. Oct. 2001;11(5):570-575.

Nichol G, Huszti E, Rokosh J, Dumbrell A, McGowan J, Becker L. Impact of informed consent requirements on cardiac arrest research in the United States: exception from consent or from research? Resuscitation. Jul. 2004;62(1):3-23.

Nichol G, Thomas E, Callaway CW, Hedges J, Powell JL, Aufderheide TP, et al. Regional variation in out-of-hospital cardiac arrest incidence and outcome. Jama. Sep. 24, 2008;300(12):1423-31.

Nielsen N, et al., Outcome, timing and adverse events in therapeutic hypothermia after out-of-hospital cardiac arrest, Acta Anaesthesiol Scand 2009; 53: 926-937.

Nilsson F, Nielsen N, Höglund P. The effects of achieving hypothermia early in a heterogeneous population of patients with cardiac arrest.

(56) References Cited

OTHER PUBLICATIONS

Int. J. Cardiol [Internet]. Nov. 9, 2009 [cited Nov. 15, 2009];Available from: http://www.ncbi.nlm.nih.gov/pubmed/19906453.
Nolan JP, Morley PT, Hoek TL, Hickey RW. Therapeutic hypothermia after cardiac arrest. An advisory statement by the Advancement Life support Task Force of the International Liaison committee on Resuscitation. Resuscitation. Jun. 2003;57(3):231-235.
Nolan JP et al, European resuscitation council guidelines for resuscitation 2005, Section 4. Adult advanced life support, Resuscitation (2005) 6751, 539-586.
Nozari A, Safar P, Stezoski SW, Wu X, Henchir J, Radovsky A, et al. Mild hypothermia during prolonged cardiopulmonary cerebral resuscitation increases conscious survival in dogs. Critical Care Medicine. Oct. 2004;32 (10):2110-2116.
Oddo M, Ribordy V, Feihl F, Rossetti AO, Schaller MD, Chiolero R, et al. Early predictors of outcome in comatose survivors of ventricular fibrillation and non-ventricular fibrillation cardiac arrest treated with hypothermia: a prospective study. Crit Care Med. Aug. 2008;36(8):2296-2301.
Oddo M, Schaller MD, Feihl F, et al. From evidence to clinical practice: effective implementation of therapeutic hypothermia to improve patient outcome after cardiac arrest. Crit Care Med. Jul. 2006;34(7):1865-1873.
Oku T, Fujii M, Tanaka N, Imoto H, Uchiyama J, Oka F, et al. The influence of focal brain cooling on neurophysiopathology: validation for clinical application. J. Neurosurg. Jun. 2009;110(6):1209-1217.
Olson D et al, Critical care nurses' workload estimates for managing patients during induced hypothermia, British Assoc. of Critical Care Nurses, (2008) vol. 13, No. 6, pp. 305-309.
Osler T, Rogers F, Fletcher D. Perioperative Normothermia and surgical-wound infection. N Engl J Med. Sep. 5, 1996;335(10):748; author reply 749-750.
Pagnocca ML, Tai EJ, Dwan JL. Temperature control in conventional abdominal surgery: comparison between conductive and the association of conductive and convective warming. Revista Brasileira De Anestesiologia. Jan.-Feb. 2009;59(1):61-6, 56-61.
Pajares JM, Gisbert JP. Helicobacter pylori: its discovery and relevance for medicine. Rev Esp Enferm Dig. Oct. 2006;98(10):770-785.
Paal et al, Excessive stomach inflation causing gut ischaemia, Resuscitation 80 (2009) 142.
Parham W, Edelstein K, Unger B, Mooney M. Therapeutic hypothermia for acute myocardial infarction: past, present, and future. Critical Care Medicine. Jul. 2009;37(7 Suppl):S234-237.
Paulikas CA. Prevention of unplanned perioperative hypothermia. AORN Journal. Sep. 2008;88(3):358-65; quiz 365-358.
Pennes HH, Analysis of Tissue and Arterial Blood Temperatures in the Resting Human Forearm, Journal of Applied Physiology, vol. 1, Aug. 1948, No. 2.
Perlman, Ethics of therapeutic hypothermia, Acta Paediatrica (2009) 98, pp. 211-213.
Pichon N, Amiel JB, Francois B, Dugard A, Etchecopar C, Vignon P. Efficacy of and tolerance to mild induced hypothermia after out-of-hospital cardiac arrest using an endovascular cooling system. Critical Care (London, England). 2007;11(3):R71.
Pirrallo RG et al, Effect of an inspiratory impedance threshold device on hemodynamics during conventional manual cardiopulmonary resuscitation, Resuscitation 66 (2003) 13-20.
Plattner O, Ikeda T, Sessler DI, Christensen R, Turakhia M. Postanesthetic vasoconstriction slows peripheral-to-core transfer of cutaneous heat, thereby isolating the core thermal compartment. Anesthesia and Analgesia. Oct. 1997;85 (4):899-906.
Plattner O, Kurz A, Sessler DI, Ikeda T, Christensen R, Marder D, et al. Efficacy of intraoperative cooling methods. Anesthesiology. Nov. 1997;87(5):1089-1095.
Polderman KH, Callaghan J. Equipment review: cooling catheters to induce therapeutic hypothermia? Critical Care (London, England). 2006;10(6):234.
Polderman KH, Peerdeman SM, Girbes AR. Hypophosphatemia and hypomagnesemia induced by coohng in patients with severe head injury. Journal of Neurosurgery. May 2001:94(5):697-705.
Polderman KH. Application of therapeutic hypothermia in the ICU: opportunities and pitfalls of a promising treatment modality. Part 1: Indications and evidence. Intensive Care Medicine. Apr. 2004;30(4):556-75.
Polderman KH. Application of therapeutic hypothermia in the intensive care unit. Opportunities and pitfalls of a promising treatment modality—Part 2: Practical aspects and side effects. Intensive Care Medicine. May 2004;30 (5):757-769.
Polderman KH. Mechanisms of action, physiological effects, and complications of hypothermia. Critical Care Medicine. Jul. 2009;37(7 Suppl):S186-202.
Polderman KH et al, Therapeutic hypothermia and controlled normothermia in the intensive care unit: Practical considerations, side effects, and cooling methods, Crit Care Med (2009) vol. 37, No. 3, pp. 1101-1120.
Polderman KH et al, Hypothermic therapy after traumatic brain injury in children, N Engl J Med 359; 11 Sep. 11, 2008 1178-1180.
Poppa E, Yona D, Katz Y, Barak M. Warmflo(R) warming system overheats fluids in simulated clinical conditions. J Clin Anesth [Internet]. Aug. 21, 2009 [cited Aug. 25, 2009];Available from: http://www.ncbi.nlm.nih.gov/pubmed/19700285.

\* cited by examiner

FIG. 3A　　　　FIG. 3C

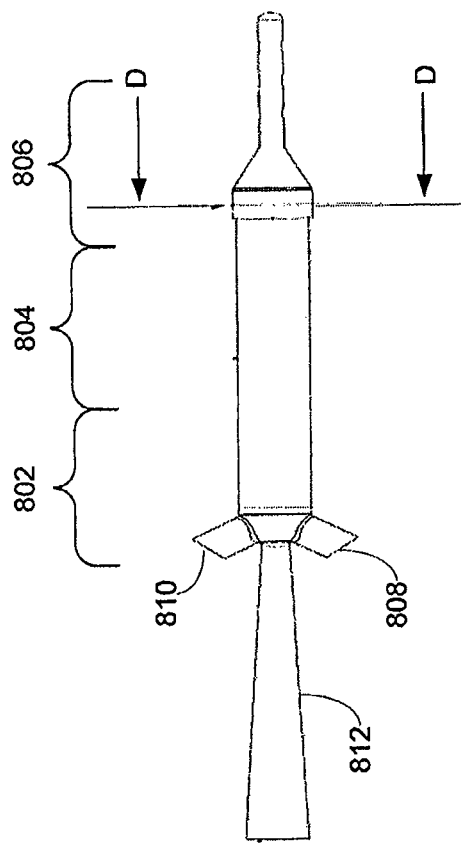
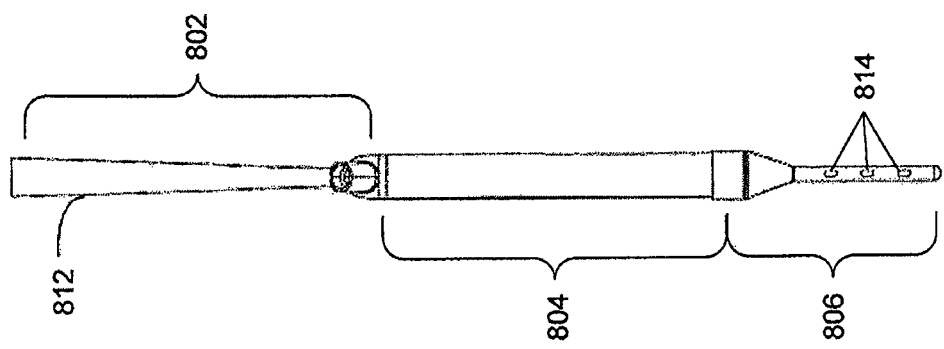
FIG. 8A
FIG. 8B

DEVICES AND METHODS FOR CONTROLLING PATIENT TEMPERATURE

RELATED APPLICATIONS

This application is a continuation of U.S. patent application Ser. No. 13/768,752, now U.S. Pat. No. 9,301,871 filed on Feb. 15, 2013, which is a continuation-in-part of U.S. patent application Ser. No. 13/609,624, now U.S. Pat. No. 9,326,890 filed on Sep. 11, 2012, which is a continuation-in-part of U.S. patent application Ser. No. 13/482,581, now U.S. Pat. No. 9,622,909 filed on May 29, 2012, which is a continuation-in-part of U.S. patent application Ser. No. 13/021,805, now U.S. Pat. No. 8,444,684, Ser. No. 13/021,820, now U.S. Pat. No. 8,523,929, and Ser. No. 13/021,828, now U.S. Pat. No. 8,696,725, all filed on Feb. 7, 2011, which were filed as continuations of U.S. patent application Ser. No. 12/713,644, now U.S. Pat. No. 8,231,664 filed on Feb. 26, 2010, which claims the priority of U.S. Patent Application No. 61/155,876 filed on Feb. 26, 2009. The disclosures of each of the aforementioned applications are hereby incorporated by reference in their entireties.

FEDERALLY SPONSORED RESEARCH OR DEVELOPMENT

This invention was made with Government support under National Science Foundation (NSF) Award Number 1142664. The Government has certain rights in this invention.

BACKGROUND OF THE INVENTION

In industrial countries, 36 to 128 per 100,000 inhabitants per year experience a sudden out-of-hospital cardiac arrest ("OHCA") with survival remaining a rare event. Cardiovascular disease affects an estimated 80,700,000 North American adults, with approximately 2400 individuals dying from cardiovascular disease daily (an average of one death every 37 seconds). Approximately 310,000 coronary heart disease deaths due to OHCA occur annually.

According to data reported by the National Registry of Cardiopulmonary Resuscitation in 2007, over 75% of patients having cardiopulmonary arrest events did not survive the event. For those who did survive the event, an additional 35.2% died afterward.

In the 1950s, moderate hypothermia (body temperature of approximately 28° C. to approximately 32° C.) and deep hypothermia (body temperature of approximately <28° C.) were utilized for various surgical procedures as well as experimentally to reverse neurological insults associated with cardiac arrest. However, because of the numerous complications of moderate-to-deep hypothermia and the difficulty in inducing these temperature reductions, enthusiasm for the use of therapeutic hypothermia waned. Consequently, the use of hypothermia to help reverse the neurologic insult after normothermic cardiac arrest lay dormant for several decades. However, beginning in the late 1980s, positive outcomes following cardiac arrest were reported in dogs with mild hypothermia.

Contemporary use of mild therapeutic hypothermia following cardiac arrest in human patients is supported by recent randomized control trials and a meta-analysis of individual patient data. Major organizations, including the International Liaison Committee on Resuscitation ("ILCOR") and the American Heart Association ("AHA"), recommend the induction of mild therapeutic hypothermia for comatose cardiac arrest survivors. However, the AHA therapeutic hypothermia guidelines lack a concrete description of exactly how to cool patients.

Despite widespread support for mild therapeutic hypothermia in the context of cardiac arrest, including consensus recommendations from major resuscitative organizations, the use of mild therapeutic hypothermia in clinical practice remains low. Many clinicians report that therapeutic hypothermia is too technically difficult to achieve in practice.

In addition, health care professionals occasionally need to induce hypothermia during certain surgical procedures or prevent inadvertent hypothermia and the multiple adverse effects that result from uncontrolled and unintended deviations from normal body temperature.

Control of a patient's body temperature while undergoing surgical procedures in the operating room is beneficial because, for instance, even mild inadvertent hypothermia during operative procedures increases the incidence of wound infection, prolongs hospitalization, increases the incidence of morbid cardiac events and ventricular tachycardia, and impairs coagulation.

Even mild hypothermia (<1° C.) significantly increases blood loss by approximately 16% and increases the relative risk for transfusion by approximately 22%, while maintaining perioperative normothermia reduces blood loss and transfusion requirement by clinically important amounts.

Because considerable strong evidence shows that thermal management improves outcomes in a variety of surgical patients, the current American Heart Association-American College of Cardiology 2007 Guidelines on Perioperative Cardiovascular Evaluation and Care for Noncardiac Surgery include a Level 1 recommendation for maintenance of perioperative normothermia.

Moreover, recognizing the numerous complications of perioperative hypothermia, the American Society of Anesthesiologists (ASA) has recently recommended that postoperative temperature become a basis for assessing physician compliance with current guidelines on the prevention of hypothermia.

Although inadvertent operative hypothermia is considered one of the most preventable surgical complications, existing methods to control body temperature are limited in efficacy, such that the incidence of inadvertent operative hypothermia for surgical patients can exceed 50%.

Currently available methods to control body temperature include both non-invasive and invasive techniques. For example, the most commonly used techniques developed to induce therapeutic hypothermia include surface cooling and invasive cooling.

Surface cooling is relatively simple to use, and can be accomplished by the use of external vests, cooling helmets, circulating cold-water blankets, cold forced-air blankets, or with less sophisticated methods, such as ice packs and cold-water immersion, but takes between 2 and 8 hours to reduce core body temperature. Surface cooling is limited by the rate at which cooling can occur, due to the tendency of blood flow to be shunted away from skin and towards the core. External devices, such as vests or blankets, significantly limit access to important patient areas that are often needed in critical care, such as for catheter placement, and require removal or modification to perform CPR. Surface cooling techniques such as ice packs limit the precision with which a patient's temperature can be controlled. Cooling with ice packs and conventional cooling blankets often results in unintentional overcooling.

For successful induction and maintenance of induced hypothermia and maintenance of normothermia, shivering, as well as other thermoregulatory responses, must be addressed. Benefits from cooling may be offset by negative consequences from shivering. Both pharmacological and nonpharmacological methods have been used to control shivering in therapeutic hypothermia, with meperidine offering one pharmacologic choice that may provide the greatest reduction in the shivering threshold, and other effective pharmacological agents being dexmedetomidine, midazolam, fentanyl, ondansetron, and magnesium sulfate. As a last resort, neuromuscular blocking agents are considered appropriate therapy for management of refractory shivering. Skin counterwarming techniques, such as use of an air-circulating blanket, are non-pharmacological methods for reducing shivering when used in conjunction with medication. Nevertheless, treatment for shivering while avoiding the negative consequences of many anti-shivering therapies is often difficult.

As another example, several methods are utilized to warm a patient, and include raising the operating room temperature and using external warming devices, such as forced-air warming blankets.

Several issues exist with these current methods: (1) excessively warm room temperature creates an uncomfortable environment for the surgical team, (2) forced-air warmers are bulky and may impact the surgical field; they tend to be inefficient and must be used for extended periods of time in the operating room, and (3) none of these systems adequately control or manage temperature, leading to both overheating or, more often, inadequate warming.

Rasmussen et al. (Forced-air surface warming versus oesophageal heat exchanger in the prevention of perioperative hypothermia. Acta Anaesthesiol Scand. 1998 March; 42(3):348-52) mention that forced-air warming of the upper part of the body is effective in maintaining normothermia in patients undergoing abdominal surgery of at least 2 h expected duration, while central heating with an esophageal heat exchanger does not suffice to prevent hypothermia. Bräuer et al. (Oesophageal heat exchanger in the prevention of perioperative hypothermia. Acta Anaesthesiol Scand. 1998 March; 42(10):1232-33) states that an esophageal heat exchanger can only add a small amount of heat to the overall heat balance of the body.

Invasive temperature management treatments include: the infusion of cold intravenous fluids; the infusion of warmed intravenous fluids; cold carotid infusions; single carotid artery perfusion with extracorporeal cooled blood; cardiopulmonary bypass; ice water nasal lavage; cold peritoneal lavage; nasogastric and rectal lavage; and the placement of invasive intravenous catheters connected to refrigerant or heat exchange (warming) devices. Invasive temperature management treatments often require significant personnel involvement and attention to perform successfully. Moreover, certain invasive temperature management modalities have been associated with overcooling, overheating, or, more often, inadequate warming.

The use of intravenous fluid as a temperature management modality has the undesirable effect of contributing to circulating fluid volume overload, and has been found to be insufficient for maintaining target temperature. In addition, large volumes of fluids must be infused to obtain a significant effect.

Other techniques for achieving hypothermia include blood cooling through inhaled gases and the use of balloon catheters.

However, Andrews et al. (Randomized controlled trial of effects of the airflow through the upper respiratory tract of intubated brain-injured patients on brain temperature and selective brain cooling. Br. J. Anaesthesia. 2005; 94(3):330-335) mention that a flow of humidified air at room temperature through the upper respiratory tracts of intubated brain-injured patients did not produce clinically relevant or statistically significant reductions in brain temperature.

Dohi et al. (Positive selective brain cooling method: a novel, simple, and selective nasopharyngeal brain cooling method. Acta Neurochirgurgica. 2006; 96:409-412) mention that a Foley balloon catheter inserted to direct chilled air into the nasal cavity, when used in combination with head cooling by electric fans, was found to selectively reduce brain temperature.

Holt et al. (General hypothermia with intragastric cooling. Surg. Gynecol Obstet. 1958; 107(2):251-54; General hypothermia with intragastric cooling: a further study. Surg Forum. 1958; 9:287-91) mention using an intragastric balloon in combination with thermic blankets to produce hypothermia in patients undergoing surgical procedures.

Likewise, Barnard (Hypothermia: a method of intragastric cooling. Br. J. Surg. 1956; 44(185):296-98) mentions using an intragastric balloon for inducing hypothermia by intragastric cooling.

US Patent Application Publication 2004/0199229 to Lasheras mentions heating or cooling via a balloon inserted into a patient's colon.

US Patent Application Publication 2004/0210281 to Dzeng et al. (now U.S. Pat. No. 7,758,623) mentions a transesophageal balloon catheter for specifically cooling the heart and disparages technologies that cool the entire body.

US Patent Application Publication 2007/0055328 to Mayse et al. mentions a balloon catheter for protecting the digestive tract of a person undergoing cardiac ablation to correct cardiac arrhythmia.

U.S. Pat. No. 6,607,517 to Dae et al. is generally directed to using endovascular cooling to treat congestive heart failure.

Several complications are known to result from increasing pressure within the gastrointestinal tract, as may occur with a balloon inflated within the stomach, colon, or other gastrointestinal organ. For example, stomach inflation may trigger intestinal rupture, regurgitation and aspiration that may result in pneumonia, esophageal tears, colon necrosis, and gut ischemia.

In addition, several temperature-controlling modalities, particularly those that employ inflatable balloons, limit access of the health care provider to particular anatomical structures that may be crucial for patient care, such as the stomach. These modalities may require removal or modification to achieve proper treatment.

To date, no available modality for controlling patient temperature has been found that sufficiently overcomes the technical, logistical, and financial barriers that exist. The ideal patient temperature control device has yet to be developed.

In summary, the state of the art related to the control of patient temperature comprises at least one significant long felt need: methods and devices for efficient, safe, and rapid control of patient temperature while maintaining access to anatomical areas necessary for additional treatment. The present technology identifies several indications, diseases, disorders, and conditions that can be treated or prevented by controlling patient temperature and, further, provides relatively non-invasive methods and devices for rapidly and efficiently controlling patient temperature while reducing the risks posed by prior devices and methods. Moreover, certain embodiments of the present technology provide relatively non-invasive methods and devices for rapidly and efficiently controlling patient temperature, while at the same time maintaining access to important anatomical structures. Certain embodiments of the present technology also provide methods and devices for inducing and maintaining mild hypothermia or maintaining normothermia in a subject without producing thermoregulatory shivering. Certain embodiments of the present technology also provide methods and devices for maintaining a subject's core body temperature within a narrow range with little variation around the goal temperature throughout the steady-state of the treatment protocol. Certain embodiments of the present technology also provide methods and devices for efficiently re-warming a subject following induced hypothermia.

BRIEF SUMMARY OF THE INVENTION

At least one aspect of the present technology provides one or more methods for inducing systemic hypothermia. The methods comprise inserting a heat transfer device, including a fluid path defined by an inflow lumen and an outflow lumen, into a patient's esophagus; initiating flow of a cooling medium along the fluid path; and circulating the medium along the fluid path for a time sufficient to induce systemic hypothermia in the patient. The heat transfer device may comprise a heat transfer region having a splined inner surface surrounding the cooling medium flow path. The heat transfer device may include a discrete heat transfer region that is confined to the patient's esophagus. The patient may be maintained in a state of hypothermia for at least about two hours, for example. The methods may further comprise monitoring at least one physiological parameter of the patient, such as body temperature, pressure, oxygen saturation, pH, heart rate, Doppler signals, electromagnetic fluctuations, or chemical composition. For example, the methods may comprise monitoring intra-abdominal compartment pressure or monitoring esophageal pressure through a pressure transducer incorporated with the device. The methods may further comprise using a lab-on-chip to perform biochemical assays, dielectrophoresis, real-time PCR, and immunoassays for the detection of bacteria, viruses, and cancers. The methods may further comprise maintaining the patient's body temperature below about 34° C.

At least one aspect of the present technology provides one or more methods for controlling core body temperature in a subject. The methods comprise inserting a heat transfer device, including a fluid path defined by an inflow lumen and an outflow lumen, into a subject's esophagus; initiating flow of a heat transfer medium along the fluid path; and circulating the medium along the fluid path for a time sufficient to control core body temperature in a subject. The heat transfer device may comprise a heat transfer region having a splined inner surface surrounding the heat transfer medium flow path. The heat transfer device may include a discrete heat transfer region that is confined to the patient's esophagus. The core body temperature of the subject may be controlled for at least about two hours, for example. The methods may further comprise monitoring at least one physiological parameter of the subject, such as body temperature, pressure, oxygen saturation, pH, heart rate, Doppler signals, electromagnetic fluctuations, or chemical composition. For example, the methods may comprise monitoring intra-abdominal compartment pressure or monitoring esophageal pressure through a pressure transducer incorporated with the device. The methods may further comprise using a lab-on-chip to perform biochemical assays, dielectrophoresis, real-time PCR, and immunoassays for the detection of bacteria, viruses, and cancers. The methods may further comprise maintaining the patient's body temperature, for example, below about 34° C., between about 34° C. and about 37° C., or at about 37° C.

At least one aspect of the present technology provides one or more esophageal heat transfer devices. The devices comprise: a plurality of lumens configured to provide a fluid path for flow of a heat transfer medium; a proximal end including an input port and an output port; a distal end configured for insertion into a patient's esophagus. The devices may further comprise a hollow tube having a distal end configured to extend into the patient's stomach or a more distal component of the gastrointestinal tract, such as the jejunum. The hollow tube can be used to administer medications or alimentation to the gastrointestinal tract. The devices may further comprise an anti-bacterial coating.

At least one aspect of the present technology provides one or more methods for treating or preventing ischemia-reperfusion injury or injury caused by an ischemic condition. The methods comprise inserting a heat transfer device, including a fluid path defined by an inflow lumen and an outflow lumen, into a patient's esophagus; initiating flow of a cooling medium along the fluid path; and circulating the cooling medium along the fluid path for a time sufficient to induce systemic hypothermia in the patient. The heat transfer device may comprise a splined inner surface surrounding the cooling medium flow path.

At least one aspect of the present technology provides one or more methods for treating or preventing neurological or cardiac injury. The methods comprise inserting a heat transfer device, including a fluid path defined by an inflow lumen and an outflow lumen, into a patient's esophagus; initiating flow of a cooling medium along the fluid path; and circulating the cooling medium along the fluid path for a time sufficient to induce systemic hypothermia in the patient. The neurological injury may be associated with, for example, stroke (including ischemic stroke), traumatic brain injury, spinal cord injury, subarachnoid hemorrhage, out-of-hospital cardiopulmonary arrest, hepatic encephalopathy, perinatal asphyxia, hypoxic-anoxic encephalopathy, infantile viral encephalopathy, near-drowning, anoxic brain injury, traumatic head injury, traumatic cardiac arrest, newborn hypoxic-ischemic encephalopathy, hepatic encephalopathy, bacterial meningitis, cardiac failure, post-operative tachycardia, or acute respiratory distress syndrome ("ARDS"). The heat transfer device may comprise a splined inner surface surrounding the cooling medium flow path.

At least one aspect of the present technology provides one or more methods for treating myocardial infarction, stroke, traumatic brain injury, or ARDS. The methods comprise inducing mild therapeutic hypothermia in a patient. Mild therapeutic hypothermia may be induced via esophageal cooling. The patient may be maintained in a state of hypothermia for at least about two hours, for example. The methods may further comprise monitoring at least one physiological parameter of the patient, such as body temperature, pressure, oxygen saturation, pH, heart rate, Doppler signals, electromagnetic fluctuations, or chemical composition. For example, the methods may comprise monitoring intra-abdominal compartment pressure or monitoring esophageal pressure through a pressure transducer incorporated with the device. The methods may further comprise using a lab-on-chip to perform biochemical assays, dielectrophoresis, real-time PCR, and immunoassays for the detection of bacteria, viruses, and cancers. The methods may further comprise maintaining the patient's body temperature below about 34° C.

At least one aspect of the present technology provides one or more methods for treating myocardial infarction, stroke, traumatic brain injury, or ARDS. The methods comprise inserting a heat transfer device, including a fluid path defined by an inflow lumen and an outflow lumen, into a patient's esophagus; initiating flow of a cooling medium along the fluid path; and circulating the cooling medium along the fluid path for a time sufficient to induce systemic hypothermia in the patient. The heat transfer device may comprise a splined inner surface surrounding the cooling medium flow path.

At least one aspect of the present technology provides one or more methods for treating cardiac arrest. The methods comprise inducing systemic hypothermia via esophageal cooling. The methods may further comprise inserting a heat transfer device, including a fluid path defined by an inflow lumen and an outflow lumen, into a patient's esophagus; initiating flow of a cooling medium along the fluid path; and circulating the cooling medium along the fluid path for a time sufficient to induce systemic hypothermia in the patient. The heat transfer device may comprise a splined inner surface surrounding the cooling medium flow path.

At least one aspect of the present technology provides one or more methods for operative temperature management. The methods comprise controlling a patient's core body temperature via esophageal cooling. The methods may further comprise inserting a heat transfer device, including a fluid path defined by an inflow lumen and an outflow lumen, into a patient's esophagus; initiating flow of a heat transfer medium along the fluid path; and circulating the heat transfer medium along the fluid path for a time sufficient to control the patient's core body temperature. The methods may further comprise administering medications or alimentation to the gastrointestinal tract while simultaneously controlling a patient's core body temperature via esophageal cooling.

At least one aspect of the present technology provides one or more devices for cooling or warming multiple portions of a patient's body simultaneously. The devices comprise a heat transfer device including a proximal end, a distal end, at least one flexible tube extending the proximal and distal end, and additional flexible tubes extending from the proximal end. The proximal end includes a heat transfer medium input port, a heat transfer medium output port, and from about 2 to about 4 ancillary tubes extending off the proximal end providing for multiple heat transfer medium flow pathways. The distal end of the device is configured for insertion into a larger orifice of a patient, while the distal ends of the ancillary tubes are configured for insertion into additional smaller orifices or configured external as an external component for surface contact. For example, the ancillary tubes can be configured as a head and/or neck wrap to provide surface cooling.

At least one aspect of the present technology provides a heat transfer device, which may comprise (a) a plurality of lumens configured to provide a fluid path for flow of a heat transfer medium; (b) a heat transfer region configured for contacting esophageal epithelium, nasopharyngeal epithelium, auricular canal epithelium, and or the tympanic membranes of a patient; (c) a proximal end including an input port, an output port, and ancillary tubing containing heat transfer medium flow channels; and (d) a distal end configured for insertion into an esophagus of a patient. The heat transfer device can also comprise a hollow tube having a distal end configured to extend into the patient's stomach or a more distal component of the gastrointestinal tract, such as the jejunum. The hollow tube can be used to administer medications or alimentation to the gastrointestinal tract. The heat transfer device can be capable of contacting substantially all of the patient's esophageal epithelium, nasopharyngeal epithelium, auricular canal epithelium, or the tympanic membranes.

At least one aspect of the present technology provides one or more devices for cooling or warming at least one portion of a patient's body. The devices comprise a heat transfer device including a proximal end, a distal end, and at least one flexible tube extending between the proximal and distal end. The proximal end includes a heat transfer medium input port and a heat transfer medium output port. The distal end is configured for insertion into an orifice of a patient. The flexible tube defines an inflow lumen and an outflow lumen and the lumens may be configured to provide a fluid path for flow of a heat transfer medium. The heat transfer medium is delivered to a heat transfer region of the heat transfer device via the inflow lumen and removed from the heat transfer region via the outflow lumen. The inflow and outflow lumens may comprise a part or all of the heat transfer region. A single flexible tube may define both the inflow lumen and the outflow lumen. For example, the flexible tube may take on a U-shaped configuration or a substantially helical configuration such that one portion of the tube defines the inflow lumen and another portion of the flexible tube defines the outflow lumen. Alternatively, the same portion of the flexible tube may define the inflow and outflow lumens. For example, heat transfer medium may be delivered to the heat transfer region and extracted from the heat transfer region via the same portion of the flexible tube. In one embodiment, an external pump may alternatively deliver and withdraw heat transfer medium via a single flexible tube. In yet another embodiment of the present technology, more than one flexible tube may define the inflow and outflow lumens. For example, two or more tubes may be arranged concentrically such that the lumen of the outer tube serves as the inflow lumen and the lumen of the inner tube serves as the outflow lumen. Alternatively, two or more tubes may be arranged in parallel, with at least one tube defining an inflow lumen and at least one tube defining an outflow lumen. The lumens of the parallel tubes may be connected such that the heat transfer medium can pass from the inflow lumen to the outflow lumen. The flexible tube may comprise a splined inner surface surrounding the heat transfer medium flow path. The devices further comprise a supply line connected to the input port and a return line connected to the output port.

The device may be used to treat or prevent, for example, injury caused by an ischemic condition; ischemia-reperfusion injury; neurological injury; cardiac injury. The device may be used to treat patients who have experienced or are experiencing myocardial infarction; stroke; traumatic brain injury; or ARDS. The methods of treating or preventing such conditions or diseases comprise inserting the distal end of the heat transfer device nasally or orally; advancing the distal end into the patient's esophagus; initiating flow of a cooling medium along the fluid path; and circulating the cooling medium along the fluid path for a time sufficient to induce systemic hypothermia in the patient. The patient may be maintained in a state of hypothermia for at least two hours. The methods may further comprise monitoring at least one physiological parameter of the patient, such as body temperature, pressure, oxygen saturation, pH, heart rate, Doppler signals, electromagnetic fluctuations, or chemical composition. For example, the methods may comprise monitoring intra-abdominal compartment pressure or monitoring esophageal pressure through a pressure transducer incorporated with the device. The methods may further comprise using a lab-on-chip to perform biochemical assays, dielectrophoresis, real-time PCR, and immunoassays for the detection of bacteria, viruses, and cancers. The methods may further comprise maintaining the patient's body temperature below about 34° C.

The device may be used to control a patient's core body temperature during, for example, surgical procedures. The methods of controlling the patient's core body temperature comprise inserting the distal end of the heat transfer device nasally or orally; advancing the distal end into the patient's esophagus; initiating flow of a heat transfer medium along the fluid path; and circulating the heat transfer medium along the fluid path for a time sufficient to control core body temperature in the patient. The core body temperature of the subject may be controlled for at least about two hours, for example. The methods may further comprise monitoring at least one physiological parameter of the subject, such as body temperature, pressure, oxygen saturation, pH, heart rate, Doppler signals, electromagnetic fluctuations, or chemical composition. For example, the methods may comprise monitoring intra-abdominal compartment pressure or monitoring esophageal pressure through a pressure transducer incorporated with the device. The methods may further comprise using a lab-on-chip to perform biochemical assays, dielectrophoresis, real-time PCR, and immunoassays for the detection of bacteria, viruses, and cancers. The methods may further comprise maintaining the patient's body temperature, for example, below about 34° C., between about 34° C. and about 37° C., or at about 37° C.

At least one aspect of the present technology provides one or more methods for inducing systemic hypothermia while simultaneously imparting local normothermia, for example to the region of the esophagus in closest proximity to the atrium of the heart.

At least one aspect of the present technology provides an esophageal heat transfer device comprising (a) a plurality of lumens configured to provide a fluid path for flow of a heat transfer medium; (b) a heat transfer region configured for contacting esophageal epithelium of a patient; (c) a proximal end including an input port and an output port; and (d) a distal end configured for insertion into an esophagus of a patient. The heat transfer device can also comprise a hollow tube having a distal end configured to extend into the patient's stomach or a more distal component of the gastrointestinal tract, such as the jejunum. The hollow tube can be used to administer medications or alimentation to the gastrointestinal tract. The heat transfer device can be capable of contacting substantially all of the patient's esophageal epithelium. The heat transfer device can comprise a semi-rigid material. The heat transfer device can be capable of cooling at a rate of about 1.2° C./hr to about 2.4° C./hr. Alternatively, the heat transfer device can be capable of cooling at a rate of about 1.2° C./hr to about 1.8° C./hr. The heat transfer device can be capable of cooling a mass at a rate of up to about 700 kJ/hr, and, in particular, at a rate of about 410 kJ/hr. Alternatively, the heat transfer device can be capable of cooling a mass at a rate of about 350 kJ/hr to about 530 kJ/hr, and, in particular, at a rate of about 430 kJ/hr. The heat transfer device can include a heat transfer region with a surface area of at least about 100 cm$^2$ and, in particular, a surface area of about 140 cm$^2$.

At least one aspect of the present technology provides a system for cooling or warming at least one portion of a patient's body, comprising a heat transfer device including a proximal end, a distal end, and at least one semi-rigid tube extending between the proximal and distal ends; a supply line; and a return line. The proximal end of the heat transfer device includes a heat transfer medium input port and a heat transfer medium output port. The distal end of the heat transfer device is configured for insertion into an orifice of a patient, such as the esophageal lumen. The semi-rigid tube defines an inflow lumen and an outflow lumen and the lumens are configured to provide a fluid path for flow of a heat transfer medium. The supply line is connected to the input port and the return line is connected to the output port. The heat transfer device can also comprise a hollow tube having a distal end configured to extend into the patient's stomach or a more distal component of the gastrointestinal tract, such as the jejunum. The hollow tube can be used to administer medications or alimentation to the gastrointestinal tract. The heat transfer device can be capable of contacting substantially all of the patient's esophageal epithelium. The heat transfer device can comprise a semi-rigid material. The heat transfer device can be capable of cooling at a rate of about 1.2° C./hr to about 2.4° C./hr. Alternatively, the heat transfer device can be capable of cooling at a rate of about 1.2° C./hr to about 1.8° C./hr. The heat transfer device can be capable of cooling a mass at a rate of up to about 700 kJ/hr, and, in particular, at a rate of about 410 kJ/hr. Alternatively, the heat transfer device can be capable of cooling a mass at a rate of about 350 kJ/hr to about 530 kJ/hr, and, in particular, at a rate of about 430 kJ/hr. The heat transfer device can include a heat transfer region with a surface area of at least about 100 cm$^2$ and, in particular, a surface area of about 140 cm$^2$.

At least one aspect of the present technology provides a system for controlling core body temperature of a subject, comprising a heat transfer tube insertable within the esophagus of the subject; an external heat exchanger containing a heat transfer fluid; a pump for flowing the heat transfer fluid through a circuit within the heat transfer tube; a heat transfer element in contact with the external heat exchanger; a sensor for detecting a parameter and generating a signal representative of the parameter, wherein the signal is transmitted to a microprocessor to control (i) the flow of heat transfer fluid within the circuit or (ii) the temperature of the heat transfer fluid. The tube is configured to contact the epithelial lining of the subject's esophagus. The sensor can be a temperature sensor positioned distal to the heat transfer tube and configured to generate a signal representing the core body temperature of the subject. The microprocessor can receive a target temperature input and responds to the signal from the temperature sensor with a proportional integrated differential response to control the rate at which the subject approaches the target temperature. The sensor can be a bubble detector and configured to generate a signal representing the presence of air in the circuit. The heat transfer device can also comprise a hollow tube having a distal end configured to extend into the patient's stomach or a more distal component of the gastrointestinal tract, such as the jejunum. The hollow tube can be used to administer medications or alimentation to the gastrointestinal tract. The heat transfer device can be capable of contacting substantially all of the patient's esophageal epithelium. The heat transfer device can comprise a semi-rigid material. The heat transfer device can be capable of cooling at a rate of about 1.2° C./hr to about 2.4° C./hr. Alternatively, the heat transfer device can be capable of cooling at a rate of about 1.2° C./hr to about 1.8° C./hr. The heat transfer device can be capable of cooling a mass at a rate of up to about 700 kJ/hr, and, in particular, at a rate of about 410 kJ/hr. Alternatively, the heat transfer device can be capable of cooling a mass at a rate of about 350 kJ/hr to about 530 kJ/hr, and, in particular, at a rate of about 430 kJ/hr. The heat transfer device can include a heat transfer region with a surface area of at least about 100 cm$^2$ and, in particular, a surface area of about 140 cm$^2$.

At least one aspect of the present technology provides a system for controlling core body temperature of a subject. The system comprises a heat transfer device having an inflatable heat transfer region, which is insertable within the esophagus the subject and, upon inflation, at least partially restricts gastric ventilation. The system also comprises an external heat exchanger containing a heat transfer fluid; a pump for flowing the heat transfer fluid through a circuit within the heat transfer device; and a heat transfer element in contact with the external heat exchanger. The system also comprises a sensor for detecting a parameter and generating a signal representative of the parameter, wherein the signal is transmitted to a microprocessor to control (i) the flow of heat transfer fluid within the circuit or (ii) the inflation pressure of the inflatable heat transfer region. The inflatable heat transfer region is configured to contact the epithelial lining of the subject's esophagus upon inflation. The inflatable heat transfer region can be capable of contacting substantially all of the patient's esophageal epithelium upon inflation. The sensor can be a pressure sensor positioned, for example, distal to the inflatable heat transfer region and configured to generate a signal representing the intra-abdominal, gastric or esophageal pressure of the subject. The microprocessor can receive a maximum pressure determined by a health care professional and respond to the signal from the pressure sensor with a proportional integrated differential response to control (i) the flow of heat transfer fluid within the circuit or (ii) the inflation pressure of the inflatable heat transfer region. The response generated by the microprocessor is designed to alleviate the pressure built up in the gastro-intestinal tract. For example, reducing the flow of heat transfer fluid within the circuit will cause the inflatable heat transfer region to partially or fully deflate, thereby allowing for gastric ventilation. Alternatively, the microprocessor may directly control the inflation pressure of the inflatable heat transfer region. Following gastric ventilation, the microprocessor, for example, generates and sends a signal to increase pump output or otherwise re-inflate the inflatable heat transfer region, thereby at least partially restricting gastric ventilation.

At least one aspect of the present technology provides systems and methods for preventing the negative effects of elevations in gastric pressure associated with an esophageal heat transfer device having an inflatable heat transfer region that, upon inflation, at least partially restricts gastric ventilation. For example, a microprocessor may periodically deflate the inflatable heat transfer region by altering the flow of a heat transfer fluid to the inflatable heat transfer region of the device. Periodic deflation of the inflatable heat transfer region would allow for gastric ventilation. As another example, a pressure sensor for detecting intra-abdominal, gastric or esophageal pressure is incorporated with an esophageal heat transfer device having an inflatable heat transfer region that, upon inflation, at least partially restricts gastric ventilation. Information representing intra-abdominal, gastric or esophageal pressure can be communicated to a microprocessor capable of inflating or deflating the inflatable heat transfer region. The microprocessor may control inflation or deflation of the inflatable heat transfer region by, for example, altering the flow of a heat transfer fluid to the inflatable heat transfer region of the device. The pressure sensor may be located distal to the inflatable heat transfer region.

At least one aspect of the present technology provides an esophageal heat transfer device comprising: one or more lumens providing a fluid path for flow of a heat transfer medium; a distal end configured for insertion into a pharyngeal opening; a heat transfer region, wherein the heat transfer region is capable of directly contacting esophageal epithelium upon insertion into a patient; a heat transfer medium input port positioned proximal to the heat transfer region; a heat transfer medium output port positioned proximal to the heat transfer region; and a gastric tube.

In certain embodiments, the one or more lumens provide a fluid path for flow of heat transfer medium. The one or more lumens may comprise an inflow lumen and an outflow lumen. The gastric tube may be arranged in parallel to the inflow lumen or the outflow lumen. Alternatively, the gastric tube may be positioned within the inflow lumen or the outflow lumen.

In other embodiments, a single lumen provides the fluid path for flow of the heat transfer medium. The gastric tube may be arranged in parallel to the single lumen. Alternatively, the gastric tube may be positioned within the single lumen.

The heat transfer region, or a portion thereof, may be substantially helical. The substantially helical configuration creates an interior space defined by the helix, which may comprise a gastric access lumen. In certain embodiments, the gastric tube can be positioned within the gastric access lumen.

At least one aspect of the present technology provides an esophageal heat transfer device comprising: an inflow lumen connected to a heat transfer medium input port; a heat transfer region, wherein the heat transfer region is capable of directly contacting esophageal epithelium upon insertion into a patient; an outflow lumen connected to a heat transfer medium output port; a distal end configured for insertion into a nostril or mouth of a patient; and wherein the device is capable of receiving a separate gastric tube or gastric probe.

In certain embodiments, the device also comprises a gastric access tube capable of receiving the separate gastric tube or gastric probe. The gastric access tube may be arranged in parallel to the inflow lumen or the outflow lumen. Alternatively, the gastric access tube may be positioned within the inflow lumen or the outflow lumen.

In yet other embodiments, the heat transfer region, or a portion thereof, of the heat transfer device may be substantially helical. The substantially helical configuration creates an interior space defined by the helix, which may comprise a gastric access lumen. The gastric tube can be positioned within the gastric access lumen.

At least one aspect of the present technology provides an esophageal heat transfer device comprising: a distal end configured for insertion into a nostril or mouth of a patient; a heat transfer region, wherein the heat transfer region is capable of directly contacting esophageal epithelium upon insertion into the patient; and a gastric tube. The device is capable of receiving a heat transfer medium, such as a gas, liquid, solid, slurry, or gel.

The heat transfer region, or a portion thereof, may be substantially helical. The substantially helical configuration creates an interior space defined by the helix, which may comprise a gastric access lumen. In certain embodiments, the gastric tube can be positioned within the gastric access lumen.

In certain embodiments, the present technology includes a system for controlling core body temperature. The system comprises a heat transfer device having an input port capable of receiving a heat transfer medium from an external source and a lumen that is connected to the input port and provides a fluid path for flow of the heat transfer medium to an inflatable heat transfer region. Upon inflation, the inflatable heat transfer region may be capable of contacting the patient's esophageal epithelium. The system also comprises a microprocessor coupled to the external source. The microprocessor is capable of regulating the flow of the heat transfer medium to the heat transfer region. The microprocessor may also be capable of receiving a target pressure determined by a health care professional. The microprocessor may be capable of periodically increasing or decreasing the flow of the heat transfer medium to the heat transfer region. The system may also comprise a pressure sensor for detecting gastric pressure and generating a signal representative of gastric pressure. The pressure sensor may be capable of sending the signal to the microprocessor. The microprocessor may be capable of increasing or decreasing the flow of the heat transfer medium to the heat transfer region in response to the signal received from the pressure sensor. The microprocessor may be capable of responding to the signal from the pressure sensor with a proportional integrated differential response to control the flow of the heat transfer medium to the heat transfer region.

In certain embodiments, the present technology includes a method for controlling core body temperature. The method may comprise increasing, decreasing, or maintaining core body temperature. In certain embodiments the method comprises the steps of: nasally or orally inserting an esophageal heat transfer device into the patient. The heat transfer device includes an input port capable of receiving a heat transfer medium from an external source. The heat transfer device also includes an inflatable heat transfer region configured for contacting a patient's esophageal epithelium upon inflation. The heat transfer device also includes at least one lumen connected to the input port, which provides a fluid path for flow of the heat transfer medium from the input port to the inflatable heat transfer region. The method also comprises advancing the inflatable heat transfer region of the heat transfer device into the patient's esophagus. The method also comprises initiating flow of a heat transfer medium along the fluid path to inflate the inflatable heat transfer region; subsequently deflating the inflatable heat transfer region to permit gastric ventilation; and then re-inflating the inflatable heat transfer region. The method may also comprise the step of monitoring gastric pressure. Information representing gastric pressure may be communicated to a microprocessor capable of inflating or deflating the inflatable heat transfer region. The microprocessor may be capable of receiving a target pressure determined by a health care professional. The microprocessor may be capable of responding to the signal from the pressure sensor with a proportional integrated differential response to control the flow of the heat transfer medium to the heat transfer region. The method may also comprise the steps of maintaining the core body temperature of the patient at about 36° C. for at least two hours, for at least twenty four hours, or for at least seventy two hours. The method may also comprise the steps of maintaining the core body temperature of the patient below about 34° C. for at least two hours, for at least twenty four hours, or for at least seventy two hours. The method may also comprise the steps of maintaining the core body temperature of the patient at about 33° C. for at least two hours, for at least twenty four hours, or for at least seventy two hours.

In certain embodiments, the present technology includes a method for controlling core body temperature. The method may comprise increasing, decreasing, or maintaining core body temperature. In certain embodiments the method comprises the steps of: nasally or orally inserting an esophageal heat transfer device into the patient. The heat transfer device includes an inflatable heat transfer region configured for contacting a patient's esophageal epithelium upon inflation. The heat transfer device also includes at least one lumen, which provides a fluid path for flow of the heat transfer medium to the inflatable heat transfer region. The method also comprises advancing the inflatable heat transfer region of the heat transfer device into the patient's esophagus. The method also comprises initiating flow of a heat transfer medium along the fluid path to inflate the inflatable heat transfer region. Following inflation of the inflatable heat transfer region, gastric access is maintained. The method may also comprise nasally or orally inserting a gastric tube into the patient while the inflatable heat transfer region is in its inflated state. The inflatable heat transfer region may take on a substantially helical shape or a substantially hourglass shape upon inflation.

BRIEF DESCRIPTION OF SEVERAL VIEWS OF THE DRAWINGS

FIG. 3A shows a schematic view of a heat transfer device according to an exemplary embodiment of the present technology. FIG. 3C shows a cross-sectional view of a heat transfer device according to an exemplary embodiment of the present technology.

FIGS. 8A and 8B show schematic views of a heat transfer device according to an exemplary embodiment of the present technology.

DETAILED DESCRIPTION OF THE INVENTION

Figure 1:
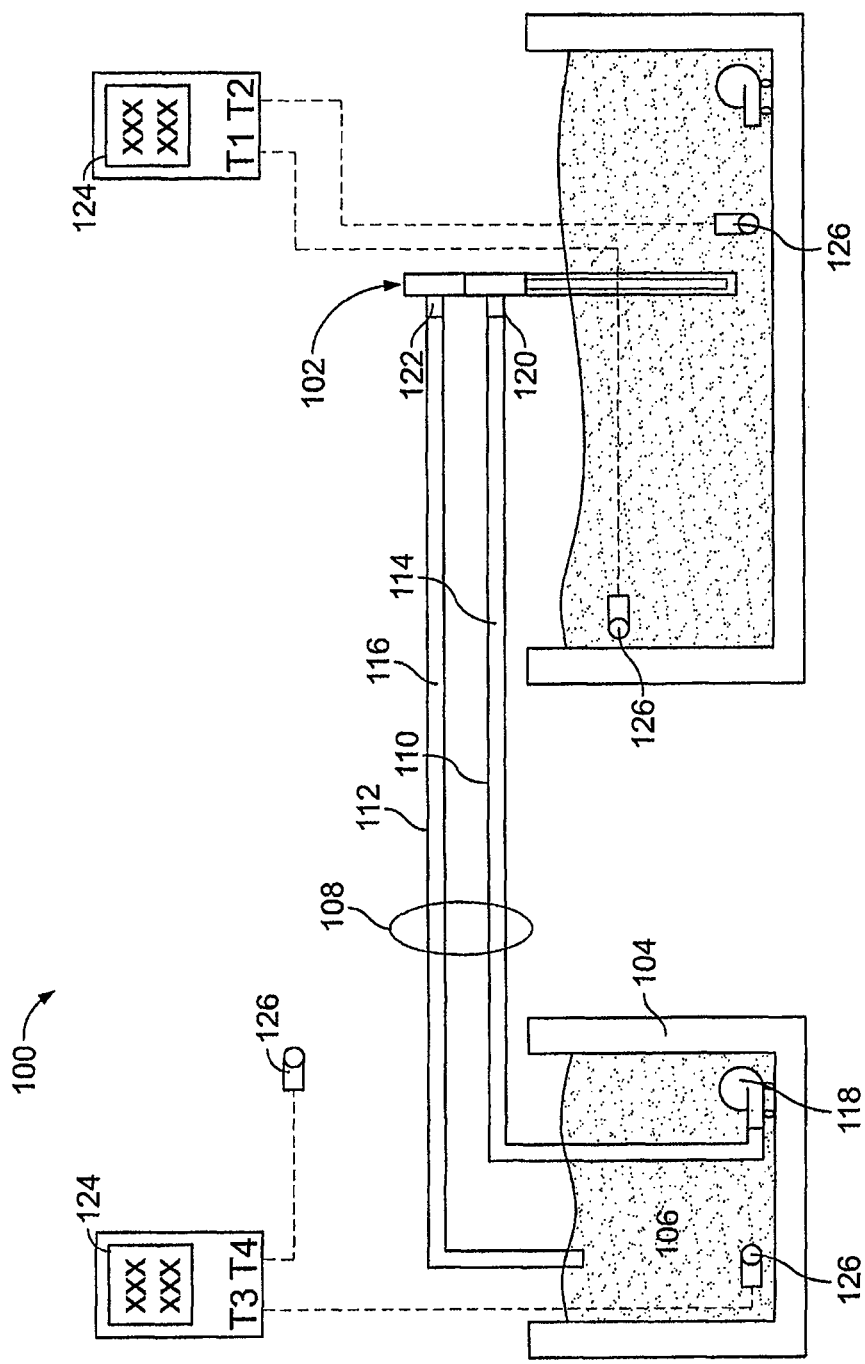
FIG. 1 is a schematic view of a heat transfer system according to an exemplary embodiment of the present technology.

The present technology provides relatively non-invasive devices and methods for heating or cooling a patient's entire body. The present technology also provides devices and methods for treating ischemic conditions by inducing therapeutic hypothermia. Another aspect of the present technology provides devices and methods for inducing therapeutic hypothermia through esophageal cooling. The present application demonstrates that heat transfer devices and methods of the present technology achieve unexpectedly-greater rates of temperature change as compared to other devices and methods and, in particular, those mentioned in US Patent Application Publication 2004/0210281 to Dzeng et al. (now U.S. Pat. No. 7,758,623).

The present technology provides devices and methods for treating patients suffering from various diseases and disorders by inducing mild therapeutic hypothermia (target temperature: about 32° C. to about 34° C.) and maintaining normothermia (target temperature: about 37° C.). In particular, mild therapeutic hypothermia may be induced to treat patients suffering from ischemia or conditions related to ischemia. Without being bound by any particular theory, it is believed that several molecular and physiological responses associated with the ischemia-reperfusion cascade, including, for example, glutamate release, stabilization of the blood-brain barrier, oxygen radical production, intracellular signal conduction, protein synthesis, ischemic depolarization, reduced cerebral metabolism, membrane stabilization, inflammation, activation of protein kinases, cytoskeletal breakdown, and early gene expression, are sensitive to intra- and post-ischemic temperature reductions. In particular, mild therapeutic hypothermia may minimize the formation of several metabolic mediators such as free radicals and suppress the inflammatory response associated with ischemia-reperfusion. Moreover, with respect to neurological outcomes, mild therapeutic hypothermia may blunt the cerebral pro-inflammatory response, decrease the production of excitatory mediators of brain injury, such as excitatory amino acids and monoamines, decrease the cerebral metabolic rate, and decrease intracranial pressure. On the other hand, inadvertent hypothermia during operative procedures can reduce platelet function, impair enzymes of the coagulation cascade, enhance anesthetic drug effects, contribute to coagulopathy, increase cardiac demand, and increase the incidence of surgical wound infections.

Certain embodiments of the present technology provide devices and methods for inducing mild therapeutic hypothermia to treat individuals who have experienced myocardial infarction, stroke, traumatic brain injury, ARDS, hemorrhagic shock, subarachnoid hemorrhage ("SAH"), including non-traumatic aneurysmal SAH, neonatal encephalopathy, perinatal asphyxia (hypoxic ischemic encephalopathy), spinal cord injury, meningitis, near hanging and near drowning. Without being bound by any particular theory, it is believed that mild therapeutic hypothermia may prevent, reduce, or ameliorate neurological, or other, damage associated with the above-mentioned conditions. Additional embodiments of the present technology provide devices and methods for inducing mild therapeutic hypothermia to treat individuals who have experienced metabolic acidosis, pancreatitis, malignant hyperthermia, liver failure and hepatic encephalopathy. Additional embodiments of the present technology provide devices and methods for controlling patient temperature during any general surgical procedure. As used herein, the term "controlling patient temperature" refers to a patient's core body temperature and includes lowering core body temperature, maintaining core body temperature, raising core body temperature, inducing hypothermia, maintaining normothermia, and inducing hyperthermia.

Certain embodiments of the present technology provide devices and methods for improving cardiac output, particularly during cardiopulmonary resuscitation (CPR). Without wishing to be bound by any particular theory, it is believed that certain esophageal heat transfer devices of the present technology add support to the medial aspect of the heart, which helps reinforce the compression of the heart during the down stroke of CPR. Placement of such a device during CPR increases cardiac output and blood flow to the brain during a crucial time, which would likely confer a survival benefit.

Certain embodiments of the present technology provide for controlling patient temperature through esophageal warming or cooling. As an example, a heat transfer agent may be circulated through a heat transfer device positioned in the patient's esophagus. In certain embodiments, the heat transfer portion of the device is confined to the patient's esophagus. In certain embodiments, the heat transfer device is in contact with substantially all of the epithelial surface of the patient's esophagus. The heat transfer device may include a balloon or partially inflatable lumen. For example, the heat transfer region of the heat transfer device may include an inflatable or partially inflatable lumen. Prior to insertion of the device into a patient, the inflatable or partially inflatable lumen may be in the deflated state. Upon insertion of the device into a patient, the inflatable or partially inflatable lumen may be inflated. As described herein, the inflatable or partially inflatable lumen may comprise an inflow and an outflow lumen, thereby providing a fluid path for the flow of a heat transfer medium.

In certain embodiments, the heat transfer device may include a balloon or partially inflatable lumen and permit gastric access. In certain embodiments, the heat transfer device further comprises a tube allowing for gastric access and, for example, gastric suctioning. In one embodiment, the inflatable or partially inflatable lumen, which comprises the heat transfer region, is arranged concentrically with the gastric access tube. For example, the inflatable or partially inflatable lumen may partially or fully surround the gastric access tube. In another embodiment, the inflatable or partially inflatable lumen, which comprises the heat transfer region, is arranged in parallel with the gastric access tube. For example, the inflatable or partially inflatable lumen may run alongside the gastric access tube. In yet another embodiment, the inflatable or partially inflatable lumen, which comprises the heat transfer region, is helically wrapped around the gastric access tube. Thus, the heat transfer region, or a portion thereof, may be substantially helical. The substantially helical configuration creates an interior space defined by the helix, within which the gastric access tube may be located. In certain other embodiments, the heat transfer device comprises a balloon or partially inflatable lumen that is capable of inflating so as to permit gastric access even when in the inflated state. For example, an inflatable or partially inflatable lumen may be manufactured such that, upon inflation, the esophagus is not completely occluded. The inflatable or partially inflatable lumen may take on an hourglass or barbell shape upon inflation. Alternatively, the inflatable or partially inflatable lumen may take on a helical shape upon inflation, such that gastric access is permitted along the axis of the helix.

As another example, inflation of the inflatable or partially inflatable lumen may be guided by a strut, boss, ring, or net to restrict the orientation of the lumen upon inflation, thereby permitting gastric access even when the lumen is in the inflated state. The strut, boss, ring, net, or other structure for restricting the orientation of the lumen upon inflation may be affixed to, for example, the outer surface of a tube defining an inflow lumen. In operation, a heat transfer medium would flow through the inflow lumen into the inflatable or partially inflatable lumen, thereby causing the inflatable or partially inflatable lumen to inflate. The structure for restricting the orientation of the lumen upon inflation prevents the inflatable or partially inflatable lumen from completely occluding the esophagus. In certain embodiments, the inflow lumen and the inflatable or partially inflatable lumen are coextensive.

Alternatively, in certain embodiments of the present invention, the heat transfer portion of the heat transfer device does not include a balloon or partially inflatable lumen.

In operation, heat can be transferred to the esophagus from the heat transfer agent, resulting in an increase in the temperature of the esophagus, as well as adjacent organs or structures, including the aorta, right atrium, vena cavae, and azygos veins, and ultimately, systemic normothermia, or heat can be transferred from the esophagus to the heat transfer agent, resulting in a decrease in the temperature of the esophagus, as well as adjacent organs or structures, including the aorta, right atrium, vena cavae, and azygos veins, and ultimately, systemic hypothermia.

Certain other embodiments of the present technology provide for controlling patient temperature through esophago-gastric heat transfer. As an example, a heat exchange medium may be circulated through a heat transfer device of sufficient length such the heat transfer portion of the device extends from the patient's esophagus to the patient's stomach. In certain embodiments, the heat transfer device is in contact with substantially all of the epithelial surface of the patient's esophagus. The heat transfer device may include a balloon or partially inflatable lumen. Alternatively, in certain embodiments of the present invention, the heat transfer portion of the device does not include a balloon or partially inflatable lumen. Employing such an esophago-gastric temperature control device to modulate patient temperature provides increased surface area for heat transfer and thereby results in more efficient and more rapid temperature management.

At least one aspect of the present technology provides one or more methods for therapeutic temperature modulation in a subject. Therapeutic temperature modulation encompasses, for example, both mild hypothermia and the maintenance of normothermia. In certain embodiments, the methods for therapeutic temperature modulation comprise controlling core body temperature in a subject. The methods comprise inserting a heat transfer device, which includes a heat transfer region comprising a fluid path defined by an inflow lumen and an outflow lumen, into a subject; initiating flow of a heat transfer medium along the fluid path; and circulating the medium along the fluid path for a time sufficient to control core body temperature in a subject. In certain embodiments, the heat transfer region of the heat transfer device can be inserted into a subject's esophagus. In certain embodiments, the present application provides methods for therapeutic temperature modulation that do not require concomitant administration of muscular paralysis medications or other medications commonly utilized to treat shivering (such as meperidine, dexmedetomidine, midazolam, fentanyl, ondansetron, or magnesium sulfate).

At least one aspect of the present technology provides one or more esophageal heat transfer devices. The devices comprise: a heat transfer region configured for placement in a subject's esophagus. The heat transfer region comprises a plurality of lumens configured to provide a fluid path for flow of a heat transfer medium. In certain embodiments, the heat transfer region of the heat transfer devices can be capable of contacting substantially all of the patient's esophageal epithelium. The devices may further comprise a gastrointestinal access tube providing access to a more distal component of the gastrointestinal tract, such as the stomach or jejunum. The gastrointestinal access tube can be used to, for example, remove the contents of the subject's stomach. In certain embodiments, esophageal heat transfer devices of the present technology are capable of being used to provide therapeutic temperature modulation in a subject without producing thermoregulatory shivering. Without wishing to be bound by any particular theory, the benefits of such devices may be related to the ability to focus heat transfer at the core of a patient away from more sensitive skin receptors thought to be active in generation of the shivering reflex; the increased contact surface between the heat transfer region of the heat transfer device and the patient's anatomy; the superior heat transfer characteristics of the materials used to construct the heat transfer devices of the present technology; and/or the reduction of gastric pressure through gastric ventilation.

In certain embodiments, esophageal heat transfer devices of the present technology are capable of maintaining a subject's core body temperature within a narrow range with little variation around the goal temperature throughout the steady-state of the treatment protocol. In some embodiments, the range is about ±1° C. of goal temperature. In other embodiments, the range is about ±0.5° C. of goal temperature. In still other embodiments, the range is about ±0.1° C. of goal temperature. Without wishing to be bound by any particular theory, such tight control of a subject's core body temperature during the steady-state of the treatment protocol may be related to a focus of heat transfer at the core of a patient where a rich and abundant vascular flow provides an optimal environment to control a patient's temperature rapidly and efficiently; the increased contact surface between the heat transfer region of the heat transfer device and the patient's anatomy; the superior heat transfer characteristics of the materials used to construct the heat transfer devices of the present technology; and/or the reduction of gastric pressure through gastric ventilation.

Certain embodiments of the present technology provide for inducing mild therapeutic hypothermia by, for example, esophageal cooling, to treat individuals who have experienced cardiac arrest, including cocaine-induced cardiac arrest, traumatic cardiac arrest, and cardiac arrest due to non-coronary causes.

Still other embodiments of the present technology provide for controlling patient temperature through cooling or warming of a patient's nasopharynx, tympanic membrane, auricular canal, bladder, colon, rectum, or other anatomical structure. As an example, a heat exchange medium may be circulated through a heat transfer device positioned in the patient's bladder, colon, rectum, or other anatomical structure.

Certain embodiments of the present technology provides for a heat transfer system for heating or cooling a patient. The heat transfer system may include a heat transfer device, a heat exchanger, a heat transfer medium, and a network of tubular structures for circulating the heat transfer medium between the heat transfer device and the heat exchanger. In other embodiments, the heat transfer system includes a heat transfer device, a chiller, a coolant and a network of tubular structures for circulating the coolant between the heat transfer device and the chiller. In still other embodiments, the heat transfer system can be used to cool and subsequently re-warm the patient, as well as maintain the patient at a predetermined maintenance temperature.

In certain embodiments of the present technology, the heat transfer device comprises a distal end, a proximal end, and one or more lengths of tubing extending therebetween. The proximal end of the heat transfer device includes an input port for receiving a heat transfer medium from the heat exchanger and an output port allowing the heat transfer medium to return to the heat exchanger. The tubing extending from approximately the proximal end of the heat transfer device to approximately the distal end of the heat transfer device may include a heat transfer medium supply tube and a heat transfer medium return tube. The heat transfer medium supply tube and heat transfer medium return tube may be arranged, for example, in parallel or concentrically. In one non-limiting example, the heat transfer medium return tube is positioned within a lumen defined by the heat transfer medium supply tube. In another non-limiting example, the heat transfer medium supply tube is positioned within a lumen defined by the heat transfer medium return tube. The lumens of the heat transfer medium supply tube and heat transfer medium return tube may be in fluid communication such that the heat transfer medium may flow along a fluid path defined by the lumens of the heat transfer medium supply tube and heat transfer medium return tube. In certain embodiments, the flow rate of the heat transfer medium along the fluid path can be sufficient to prevent significant fluctuations in the temperature of the heat transfer medium as it flows along the fluid path. For example, the flow rate of the heat transfer medium can be from about 50 mL/min to about 1000 mL/min, preferably about 750 mL/min. As another example, the flow rate of the heat transfer medium can be sufficient to maintain the temperature of the heat transfer medium within about ±3° C., within about ±2° C., within about ±1° C., or within about ±0.5° C. between inlet and outlet temperature. In some embodiments, the flow rate of the heat transfer medium can be sufficient to maintain the temperature of the heat transfer medium within about ±0.1° C. between inlet and outlet temperature.

The thickness of the walls of the heat transfer medium supply tube and/or heat transfer medium return tube contributes to the heat transfer resistance of the device. Thus, in certain embodiments, it is preferable for the heat transfer medium supply tube and/or heat transfer medium return tube to have thin walls. For example, the wall of the heat transfer medium supply tube and/or heat transfer medium return tube may be less than about 1 millimeter. Alternatively, the wall of the heat transfer medium supply tube and/or heat transfer medium return tube may be less than about 0.01 millimeter. In some embodiments, the wall of the heat transfer medium supply tube and/or heat transfer medium return tube may be less than about 0.008 millimeters. As will be appreciated by one of skill in the art, the thickness of the walls of the heat transfer medium supply tube and/or heat transfer medium return tube may be modified in increments of about 0.001 millimeters, about 0.01 millimeters, or about 0.1 millimeters, for example.

In certain embodiments, heat transfer devices of the present technology include heat transfer regions that, for example, employ splined inner surfaces surrounding the heat exchange medium flow paths. The splined inner surfaces help to enhance the likelihood of maintenance of laminar flow, and reduce the likelihood of flow obstruction at the point of curvature of the oropharynx. Heat transfer devices comprising splined inner surfaces surrounding the heat exchange medium flow paths provide an unexpectedly superior rate of temperature change relative to other devices and methods. While not wishing to be bound by any particular theory, it is thought that heat transfer devices comprising splined inner surfaces surrounding the heat exchange medium flow paths transfer more heat per unit time than other devices.

In certain embodiments, heat transfer devices of the present technology include a heat transfer region having a substantially helical configuration. For example, the heat transfer region may comprise a helical tube. The tube may comprise any material described herein, including, for example, a semi-rigid plastic, such as ethylene tetrafluoroethylene (ETFE), polytetrafluoroethylene (PTFE), perfluoroalkoxy (PFA), and fluorinated ethylene propylene (FEP), a semi-rigid elastomer, such as silicone, or an inflatable or partially inflatable material, such as a balloon. The tube defines a lumen, which, in some embodiments, provides a fluid path for the flow of a liquid or gaseous heat transfer medium. For example, the tube and corresponding lumen may serve as the evaporative component of a freon/gas circuit and be connected with an external condenser. In an alternative embodiment, the tube defines a lumen, which is capable of receiving a solid or semi-solid heat transfer medium.

A helical arrangement of the heat transfer region, or a portion thereof, allows for access to anatomical sites beyond the placement of the heat transfer device. The substantially helical configuration of the tube creates an interior space defined by the helix, which may comprise, for example, an access lumen. In some embodiments, the helical heat transfer region, or portion thereof, defines an access lumen. For example, where the heat transfer device is for placement within the esophagus, the helical heat transfer region, or portion thereof, allows for gastric access via a gastric access lumen. A separate probe, such as a temperature probe, or separate tube, such as a nasogastric tube or an orogastric tube, can be inserted into the patient via the gastric access lumen. The nasogastric tube, orogastric tube, or probe may be provided with the heat transfer device or provided as an after-market component.

The manufacture of heat transfer devices of the present technology is relatively inexpensive. For example, an esophageal heat transfer device can be constructed using an elastomer such as biomedical grade extruded silicone rubber, and an adhesive. Commercially available elastomers and adhesives include, for example, Dow Corning Q7 4765 silicone and Nusil Med2-4213. The low cost and ease of use of such materials is expected to lead to widespread adoption of the esophageal heat transfer devices of the present technology.

In certain embodiments, the heat transfer device, including, for example, the supply tube, may comprise a semi-rigid material, such as a semi-rigid plastic, including ethylene tetrafluoroethylene (ETFE), polytetrafluoroethylene (PTFE), perfluoroalkoxy (PFA), and fluorinated ethylene propylene (FEP), or a semi-rigid elastomer, such as silicone. A heat transfer device comprising a supply tube constructed of a semi-rigid material is easier to place into a patient's esophagus than, for example, a flexible, balloon-type device. In particular, a heat transfer device comprising a flexible material, such as a balloon, requires a delivery device, such as a catheter, guide wire, or sleeve, to direct the heat transfer device into the patient's esophagus. Moreover, flexible, expandable material like a balloon is susceptible to failures, such as bursting, splitting, or puncturing. Use of a semi-rigid material in the construction of a heat transfer device, reduces the points of failure associated with balloon-type device.

In certain embodiments a rigid sleeve may be employed to guide the heat transfer device during placement into a patient. The rigid sleeve may have a section cut-out such that the sleeve comprises approximately a semi-circle in cross section. The sleeve may be removed by sliding it proximally off the heat transfer device. Such a sleeve has certain benefits over a centrally placed guide wire, including a reduced rate of complications from using a guide wire, such as loss of the guide wire into the body cavity and damage caused by the guide wire itself.

In other embodiments, an esophageal heat transfer device of the present technology possesses advantages over other temperature management modalities in that no additional devices, such as stylets, or complicated techniques, such as freezing of the tube, are required for obtaining successful placement in the patient. For example, placement of traditional gastric tubes in an anesthetized, paralyzed, and intubated patient can sometimes be difficult, and many methods have been proposed to aid in the procedure when difficulties occur, including freezing of the tubes, using malleable metal stylets, and the use of slipknots on intubating stylets. Such methods are cumbersome and complicated because additional devices and/or steps are required. In some cases, gastric tubes made of nonreinforced polymer plastic materials can be prone to kinking and coiling during insertion. The ability to place a gastric tube in a relatively simple manner without requiring additional devices or complicated techniques represents a problem that is not solved by methods such as tube freezing and/or the use of malleable metal stylets or slipknots on intubating stylets. Certain embodiments of the present technology provide methods and devices for placement of a gastric tube without requiring additional devices or complicated techniques.

A heat transfer device of the present technology may be placed easily in the patient without additional devices or complicated techniques, by simply connecting the device to the external heat exchanger, turning on the external heat exchanger, and allowing the natural flow of heat exchange medium to provide sufficient firmness to the heat transfer device to allow simple placement.

An esophageal heat transfer device of the present technology is portable, relatively easy to use, and can be inserted into a patient's esophagus by a single health care provider, including a nurse, certified first responder, paramedic, emergency medical technician, or other pre-hospital or in-hospital care provider. An esophageal heat transfer device of the present technology possesses advantages over devices that require multiple people and/or a person trained in advanced medical care. In addition, in a surgical setting, for example, an esophageal heat transfer device of the present technology possesses advantages over other temperature management modalities in that less personnel and attention is required to insert, employ, and/or monitor an esophageal heat transfer device.

For example, users of a balloon-type device must guard against over- or under-inflation of the balloon. Over-inflation can lead to undesired outcomes, including pressure necrosis. Under-inflation can reduce the ability of the device to transfer heat to/from the patient. The use of a balloon-type heat transfer devices also may require the use of a pressure monitor to monitor the inflation pressure. Even when used in conjunction with a pressure monitor, it may not be able to achieve the proper inflation of the balloon.

The heat transfer device may be, for example, a pharyngeo-esophageal heat transfer device, an esophageal heat transfer device, an esophago-gastric heat transfer device, or a pharyngeo-esophago-gastric heat transfer device. For example, an esophageal heat transfer device may include a heat transfer region of about twenty (20) centimeters. Alternatively, an esophago-gastric heat transfer device may include a heat transfer region of about forty (40) centimeters. As yet another alternative, a pharyngeo-esophago-gastric heat transfer device may include a heat transfer region of about forty-five (45) to about fifty (50) centimeters. Heat transfer devices of the present technology can include heat transfer regions of about 22, about 24, about 26, about 28, about 30, about 32, about 34, about 36, about 38, about 40, about 42, about 44, about 46, about 48, about 50, about 52, about 54, about 56, about 58, about 60, about 62, about 64 about 66, about 68 or about 70 centimeters.

Heat transfer devices of the present technology can have a heat transfer region having a diameter of, for example, about 1.0 to about 2.0 centimeters. The diameter of the heat transfer region can be about 1.1, about 1.2, about 1.3, about 1.4, about 1.5, about 1.6, about 1.7, about 1.8, or about 1.9 centimeters. In certain embodiments, a heat transfer region of a heat transfer device of the present technology has a length of about 32 centimeters and a diameter of about 1.4 centimeters, giving a surface area of about 140 cm$^2$.

Increasing the length and/or circumference of the heat transfer region of the device, and therefore the surface area of the heat transfer region, improves the speed and efficiency at which the patient is cooled or heated (or re-warmed). In certain embodiments the heat transfer region can be about 15 in$^2$, about 20 in$^2$, about 25 in$^2$, 30 in$^2$, about 35 in$^2$, about 40 in$^2$, about 45 in$^2$, about 50 cm$^2$, about 60 cm$^2$, about 70 cm$^2$, about 80 cm$^2$, about 90 cm$^2$, about 100 cm$^2$, about 110 cm$^2$, about 120 cm$^2$, about 130 cm$^2$, about 140 cm$^2$, about 150 cm$^2$, about 160 cm$^2$, about 170 cm$^2$, about 180 cm$^2$, about 190 cm$^2$, about 200 cm$^2$, about 210 cm$^2$, about 220 cm$^2$, about 230 cm$^2$, about 240 cm$^2$, about 250 cm$^2$, about 260 cm$^2$, about 270 cm$^2$, about 280 cm$^2$, about 290 cm$^2$, about 300 cm$^2$, about 310 cm$^2$, about 320 cm$^2$, about 330 cm$^2$, about 340 cm$^2$, or about 350 cm$^2$. In certain embodiments, a heat transfer region can contact substantially all of the epithelial surface of a subject's esophagus.

The heat transfer device may be adapted to permit gastric access to the patient's health care provider. The heat transfer device may incorporate, for example, a gastric tube or gastric probe. The gastric tube or gastric probe may run parallel to the heat transfer medium supply tube and the heat transfer medium return tube. Alternatively, the gastric tube, the gastric probe, or both may be in a concentric arrangement with at least one of the heat transfer medium supply tube or the heat transfer medium return tube. The gastric probe may be, for example, a temperature probe.

The heat transfer device may incorporate, for example, multiple tubes and/or probes that, for example, permit access to the patient's gastrointestinal system. The gastric tubes may be adapted to, for example, deliver alimentation directly to a patient's stomach or to a more distal component of the gastrointestinal tract, such as the jejunum. The gastric tubes may also be adapted to, for example, administer medications to various components of the gastrointestinal tract, including esophageal mucosa, stomach, duodenum, and jejunum. Such devices allow for a relatively non-invasive method for controlling a patient's temperature while simultaneously administering alimentation and/or medication. Such methods and devices are superior to contemporary methods to affect temperature control and modification, which do not readily permit simultaneous medication and/or alimentation administration and gastric decompression, despite the fact that medication administration through the gastrointestinal tract is in some cases of superior efficacy to intravenous administration. Thus, the methods and devices of the present technology allow for the provision of alimentation and medication through the gastrointestinal tract, while simultaneously, allowing for temperature control and modification. Such an approach is an improvement over intravenous administration of nutrients and medications, adding substantially to the risk of complications and the expense of treatment.

In certain embodiments, the heat transfer device may incorporate a device that measures a physiological parameter such as temperature, pressure, oxygen saturation, pH, heart rate, Doppler signals, electromagnetic fluctuations, or chemical composition. For example, the heat transfer device may include or incorporate one or more thermometers, each with one or more temperature probes, for measuring the ambient temperature, patient temperature, or heat transfer medium temperature. The thermometers may be separate devices or integrated with the heat transfer system. Likewise, the heat transfer device may include or incorporate electrochemical biosensors, or biological micro-electromechanical systems (Bio-MEMS), allowing lab-on-chip (LOC) and incorporation of Micro Total Analysis Systems (pTAS) analysis of biochemical composition of the gastroesophageal environment. In addition, at least one aspect of the present technology provides one or more methods for use of a lab-on-chip to perform biochemical assays, dielectrophoresis, real-time PCR, and immunoassays for the detection of bacteria, viruses, and cancers.

In certain embodiments of the present technology, the heat transfer system may further incorporate or include a device that measures a physiological parameter such as pressure. For example, the heat transfer system may include one or more sensors of esophageal pressure, transpulmonary pressure, and/or intra-abdominal pressure.

In certain embodiments of the present technology, the heat transfer device comprises a pressure transducer located proximately, at any point along and throughout the midpoint, or distally, to allow measurement of esophageal pressure and/or transpulmonary pressure. Direct measurement of esophageal pressure allows for a subsequent estimate of transpulmonary pressure to provide, for example, guidance in supporting a patient with mechanical ventilation.

In patients with high pleural pressure on conventional ventilator settings, under-inflation may lead to atelectasis, hypoxemia, and exacerbation of lung injury. In patients with low pleural pressure, maintaining a low positive end-expiratory pressure (PEEP) keeps trans-pulmonary pressure low, avoiding over-distention and subsequent lung injury. Esophageal manometry has been used to identify the optimal ventilator settings in order to avoid both under-inflation and over-inflation of the pulmonary system; however, the optimal level of PEEP has been difficult to determine. Therefore, at least one aspect of the present technology provides one or more methods for measuring esophageal pressure as a means to estimate the transpulmonary pressure and subsequently determine optimal PEEP values that can maintain oxygenation of patients undergoing mechanical ventilation while preventing lung injury due to alveolar collapse or over-distention.

In certain embodiments of the present technology, the heat transfer device comprises a pressure transducer located distally to allow direct measurement of intra-abdominal pressure. The pressure transducer can be used to, for example, diagnose abdominal compartment syndrome. Abdominal compartment syndrome is a complication of a wide variety of illnesses, including many of which are known or suspected to benefit from control of a patient's temperature. For example, abdominal compartment syndrome can be a primary event developing from such conditions as pancreatitis, intraperitoneal hemorrhage from blunt trauma, penetrating trauma, perforation of an ulcer, or rupture of an aortic aneurysm. Abdominal compartment syndrome can also develop as a secondary event after large burns, sepsis, large volume resuscitation, penetrating or blunt trauma, or postoperatively.

At least one aspect of the present technology provides one or more methods for measuring intra-abdominal compartment pressure and diagnosing intra-abdominal compartment syndrome through the incorporation of a pressure transducer at the distal end of the device, which allows direct measurement of intra-abdominal pressure. The devices and methods of the present technology provide for superior measurement of intra-abdominal pressure as compared to contemporary methods, such as those mentioned in US Patent Application Publication 2009/0221933 to Nagao et al., which are indirect, technically challenging, invasive, and time-consuming.

Manufacture of heat transfer devices of the present technology can be accomplished via stereolithography. Stereolithography is a manufacturing process in which parts are built one layer at a time using an ultraviolet curable photopolymer resin, in a method referred to as an additive manufacturing process.

Another embodiment of the present technology provides for a multi-lumen heat transfer device for inducing mild therapeutic hypothermia. The heat transfer device may include one or more lumens that provide a fluid path for circulation of a coolant. For example, the heat transfer device may include a coolant supply tube and a coolant return tube. The lumens of the coolant supply tube and coolant return tube may be in fluid communication with each other thereby defining a fluid path for coolant flow. The coolant supply tube and coolant return tube may be arranged, for example, in parallel or concentrically.

Another embodiment of the present technology provides for a multi-lumen heat transfer device for controlling patient temperature. The heat transfer device may include one or more lumens that provide a fluid path for circulation of a heat transfer medium. For example, the heat transfer device may include a medium supply tube and a medium return tube. The lumens of the medium supply tube and medium return tube may be in fluid communication with each other thereby defining a fluid path for medium flow. The medium supply tube and medium return tube may be arranged, for example, in parallel or concentrically.

At least one aspect of the present technology provides a heat transfer device comprising one or more lumens. For example, the device may comprise a single lumen for delivery of a heat transfer medium to a heat transfer region of the device. As described herein, the heat transfer medium may be a gas (e.g., nitrous oxide, Freon, carbon dioxide, or nitrogen), liquid (e.g., water, saline, propylene glycol, ethylene glycol, or mixtures thereof), solid (e.g., ice, metal, metal alloy, or carbon fiber), slurry, and/or gel. In certain embodiments, the single lumen may function as both the inflow lumen and the outflow lumen. For example, heat transfer medium may be delivered to the heat transfer region and extracted from the heat transfer region via the single lumen by, for example, an external pump that alternatively pumps and withdraws heat transfer medium via the single lumen. In certain other embodiments, a solid heat transfer medium, which may comprise a heating element such as a wire or coil; a thermoelectric module such as a Peltier module; or a carbon fiber such as a graphitic carbon fiber, may be inserted into the single lumen.

In certain embodiments, the one or more lumens may be defined by a tube having a substantially helical configuration. The substantially helical configuration of the tube creates an interior space defined by the helix, which may comprise, for example, an access lumen. The substantially helical tube can helically wrap around a separate probe or tube, such as a commercially available nasogastric or orogastric tube. In certain embodiments, such as esophageal heat transfer devices, the substantially helical configuration allows for gastric access. For example, the external walls of the tube having a substantially helical configuration may define an access lumen. Where the heat transfer device is for placement within the esophagus, the tube having a substantially helical configuration allows for gastric access via a gastric access lumen. A separate probe, such as a temperature probe, or separate tube, such as a nasogastric tube or an orogastric tube, can be inserted into the patient via the gastric access lumen. The separate probe or tube may be inserted within the gastric access lumen before or after inserting the device into the patient. Alternatively, the nasogastric or orogastric tube may be affixed (e.g., glued) to the substantially helical tube. The nasogastric tube, orogastric tube, or probe may be provided with the heat transfer device or provided as an after-market component.

In certain embodiments, the one or more lumens may be defined by a tube having a C-shaped cross section. In certain embodiments, such as esophageal heat transfer devices, the C-shaped design allows for gastric access. For example, the C-shaped design allows for the use of a commercially available probe, such as a temperature probe, or tube, such as a nasogastric tube or an orogastric tube, with the heat transfer device of the present technology. For example, the C-shaped tube can wrap around a commercially available nasogastric or orogastric tube. The nasogastric or orogastric tube may be inserted within the interior space defined by the C-shaped tube before or after inserting the device into the patient. Alternatively, the nasogastric or orogastric tube may be affixed (e.g., glued) to the C-shaped tube.

Thus, in some embodiments, the present technology comprises an esophageal heat transfer system comprising an esophageal heat transfer device and a nasogastric tube. In other embodiments, the present technology comprises an esophageal heat transfer system comprising an esophageal heat transfer device and an orogastric tube. In still other embodiments, the present technology comprises an esophageal heat transfer system comprising an esophageal heat transfer device and a temperature probe. In yet other embodiments, the present technology comprises an esophageal heat transfer system comprising an esophageal heat transfer device and an orogastric tube, nasogastric tube, and/or temperature probe.

Yet another embodiment of the present technology provides one or more devices for cooling or warming multiple portions of a patient's body simultaneously. The devices comprise a heat transfer device including a proximal end, a distal end, at least one flexible tube extending between the proximal and distal end, and additional flexible tubes extending from the proximal end. The proximal end includes a heat transfer medium input port, a heat transfer medium output port, and about 2 to about 4 ancillary tubes extending off the proximal end providing for additional heat transfer medium flow pathways. The distal end of the device is configured for insertion into a larger orifice of a patient, while the distal ends of the ancillary tubes are configured for insertion into additional smaller orifices or configured external as an external component for surface contact. For example, the ancillary tubes can be configured as a head and/or neck wrap to provide surface cooling.

At least one aspect of the present technology provides a heat transfer device comprising (a) a plurality of lumens configured to provide a fluid path for flow of a heat transfer medium; (b) a heat transfer region configured for contacting esophageal epithelium, nasopharyngeal epithelium, auricular canal epithelium, and/or the tympanic membranes of a patient; (c) a proximal end including an input port, an output port, and ancillary tubing containing heat transfer medium flow channels; and (d) a distal end configured for insertion into an esophagus of a patient. The heat transfer device can also comprise a hollow tube having a distal end configured to extend into the patient's stomach. The heat transfer device can be capable of contacting substantially all of the patient's esophageal epithelium, nasopharyngeal epithelium, auricular canal epithelium, or the tympanic membranes.

Without wishing to be bound by theory, it is believed that affecting temperature change through the nasopharynx and/or auricular canals has the benefit of affecting temperature change at a location in direct proximity to the brain. The methods and devices of the present technology overcome the logistical and technical challenges of affecting temperature change through the nasopharynx and/or auricular canals.

A device for cooling or warming multiple portions of a patient's body simultaneously may be used to treat or prevent, for example, injury caused by an ischemic condition; ischemia-reperfusion injury; neurological injury; or cardiac injury. The device may be used to treat patients who have experienced or are experiencing myocardial infarction; stroke; traumatic brain injury; or ARDS. The methods of treating or preventing such conditions or diseases comprise, for example, inserting the distal end of the heat transfer device orally; advancing the distal end into the patient's esophagus; advancing the ancillary tubing into the patient's nasopharynx and/or into the patient's auricular canals; initiating flow of a cooling medium along the fluid path; and circulating the cooling medium along the fluid path for a time sufficient to induce systemic hypothermia in the patient. The patient may be maintained in a state of hypothermia for at least two hours. The methods may further comprise monitoring at least one physiological parameter of the patient, such as body temperature. The methods may further comprise maintaining the patient's body temperature below about 34° C.

The device may be used to control a patient's core body temperature during, for example, surgical procedures. The methods of controlling the patient's core body temperature comprise, for example, inserting the distal end of the heat transfer device nasally or orally; advancing the distal end into the patient's esophagus; advancing the ancillary tubing into the patient's nasopharynx and/or into the patient's auricular canals; initiating flow of a cooling medium along the fluid path; and circulating the heat transfer medium along the fluid path for a time sufficient to control core body temperature in the patient. The core body temperature of the subject may be controlled for at least about two hours, for example. The methods may further comprise monitoring at least one physiological parameter of the subject, such as body temperature. The methods may further comprise maintaining the patient's body temperature, for example, below about 34° C., between about 34° C. and about 37° C., or at about 37° C.

Yet another embodiment of the present technology provides relatively non-invasive devices and methods for heating or cooling a patient's entire body while simultaneously maintaining a less drastic, or opposite direction, local temperature change. Thus, at least one aspect of the present technology provides one or more methods for inducing systemic hypothermia while simultaneously imparting local normothermia, for example to the region of the esophagus in closest proximity to the atrium of the heart. Such methods and devices are superior to contemporary methods to affect temperature control and modification, which can either warm or cool independently, but are unable to cool some sections of the body while simultaneously warming others, or vice versa. Because of differential effects of temperature change on organs and regions of the human body, the ability to impart varying degrees of temperature differential, in similar or opposite directions simultaneously at different parts of the body, is beneficial.

Certain embodiments of the present technology may utilize a controller such as that described in US20070203552 (Machold). For example, a controller may employ a Peltier module to heat or cool a heat exchange region of the device, which would allow the device to alternate between heating and cooling modalities merely by changing the polarity of the current flowing through the module. In addition, the amount of heat or cold generated can be adjusted by controlling the amount of current flowing through the module. In particular, a controller may employ a cascading proportional integrated differential (PID) control scheme. In such a scheme, a control system is provided that may be divided into two sections: (a) a Bulk PID control section which takes input from the health care provider or other user, such as target temperature, and input from the sensors on the patient representing patient temperature, and calculates an intermediate set point temperature (SP1) and an output signal to the Heat Transfer Fluid PID control; and (b) the Heat Transfer Fluid PID control, that receives input from the Bulk PID control section and from a sensor representing the temperature of a heat transfer fluid, and generates a signal that controls the temperature of the heat exchanger by, for example, varying the power input to the heat exchanger.

The heat transfer fluid circulates in heat exchanger, so the Heat Transfer Fluid PID essentially controls the temperature of the heat transfer fluid. In this way, the control scheme is able to automatically achieve a specified target based on input from sensors placed on the patient and the logic built into the controller. Additionally, this scheme allows the unit to automatically alter the patient temperature very gradually the last few tenths of a degree to achieve the target temperature very gently and avoid overshoot or dramatic, and potentially damaging, swings in the electronic power to the heat exchanger. Once the target temperature is achieved, the system continues to operate automatically to add or remove heat at precisely the rate necessary to maintain the patient at the target temperature.

In general, the controller can include a controlled variable, such as pump output, inflation/deflation pressure, or power input to the heat exchanger. A detecting unit or sensor can act as a feedback device for detecting a parameter, such as patient temperature, intra-abdominal pressure, or the presence of air in a line, and outputting a feedback signal relative to the control variable. The control unit performs a PID operation, in which the controlled variable is adjusted according to the comparison between the feedback signal and a predetermined target value.

As an example, the feedback signal T can represent patient temperature and the predetermined target value $T_{Targ}$ can represent a target temperature set by a health care professional. When the feedback signal T is larger than the target value $T_{Targ}$, it means that the patient's temperature is too high. Accordingly, the controller, for example, increases or decreases pump output or power input to the heat exchanger in order to change the temperature and/or flow rate of the heat exchange medium. When the feedback signal T is smaller than the target value $T_{Targ}$, it means that the patient's temperature is too low. Accordingly, the controller, for example, increases or decreases pump output or power input to the heat exchanger in order to change the temperature and/or flow rate of the heat exchange medium.

As another example, the feedback signal P can represent the patient's intra-abdominal, esophageal, and/or gastric pressure and the predetermined target value $P_{Max}$ can represent a maximum pressure set by a health care professional. In certain embodiments, placement of an esophageal heat transfer device having an inflatable heat transfer region may cause elevated intra-abdominal, gastric, and/or esophageal pressure by preventing adequate gastric ventilation. When the feedback signal P approaches, reaches, and/or surpasses $P_{Max}$, it means that the patient's intra-abdominal, esophageal, and/or gastric pressure is in danger of or has become unacceptably high. Accordingly, the controller, for example, decreases pump output or otherwise deflates the inflatable heat transfer region in order to allow for gastric ventilation. Following gastric ventilation, the feedback signal P should approach, reach, and/or fall below $P_{Max}$ as the patient's intra-abdominal, esophageal, and/or gastric pressure is returning to or has returned to an acceptable level. Accordingly, the controller, for example, increases pump output or otherwise inflates the inflatable heat transfer region, thereby at least partially restricting gastric ventilation.

As yet another example, the controller may be programmed to periodically inflate and deflate the inflatable heat transfer region to prevent the build-up of intra-abdominal, esophageal, and/or gastric pressure. For example, the controller may increase pump output or otherwise inflate the inflatable heat transfer region. The inflation time period may be about 5 to about 60 minutes, including about 10, about 15, about 20, about 25, about 30, about 35, about 40, about 45, about 50, or about 55 minutes. During this period of inflation, the subject may experience elevated intra-abdominal, gastric, and/or esophageal pressure because adequate gastric ventilation is restricted by placement of the inflatable heat transfer region within the esophagus. Periodic deflation of the inflatable heat transfer region allows for adequate gastric ventilation. For example, the controller may decrease pump output or otherwise deflate the inflatable heat transfer region. The deflation time period may be about 1 to about 10 minutes, including about 2, about 3, about 4, about 5, about 6, about 7, about 7, about 8, or about 9 minutes.

Certain embodiments of the present technology provide an unexpectedly superior rate of temperature change relative to other devices and methods. The present methods and devices can provide a rate of cooling of about 0.5° C./hour to about 2.2° C./hour in a large animal model of similar size to an average adult human. Present methods and devices are capable of demonstrating a total heat extraction capability of about 250 kJ/hour to about 750 kJ/hour. For example, the present methods and devices can provide a rate of cooling of about 1.2° C./hr to about 2.4° C./hr in a large animal model of similar size to an average adult human. Alternatively, the present methods and devices can provide a rate of cooling of about 1.2° C./hour to about 1.8° C./hour in a large animal model of similar size to an average adult human, which demonstrates a total heat extraction capability of about 350 kJ/hour to about 530 kJ/hour. Methods and devices of the present technology can provide a rate of cooling of about 1.3, about 1.4, about 1.5, about 1.6, and about 1.7° C./hour. Methods and devices of the present technology are capable of demonstrating a total heat extraction capability of about 350, about 360, about 370, about 380, about 390 about 400, about 410, about 420, about 430, about 440, about 450, about 460, about 470, about 480, about 490, about 500, about 510, and about 520 kJ/hour.

While not wishing to be bound by any particular theory, it is thought that the methods and devices of the present technology transfer more heat per unit time than other devices. For example, heat transfer devices of the present technology include heat transfer regions that, for example, extend to substantially the entire length and/or circumference of the patient's esophagus, providing increased contact surface between the heat transfer region of the heat transfer device and patient anatomy including, the esophageal epithelium and the vasculature that surrounds the esophagus. Heat transfer devices of the present technology additionally enable reduction of gastric pressure through gastric ventilation, thereby reducing the possibility of ballooning and distention of the esophageal mucosa away from contact with the esophageal mucosa, and further enhancing heat transfer across the esophageal mucosa. In addition, materials for constructing the heat transfer devices of the present technology include those with superior heat transfer characteristics. Heat transfer devices of the present technology can be manufactured with thinner wall thicknesses, further reducing the heat transfer resistance across the device and increasing the effectiveness of heat extraction from, or heat addition to, the patient.

The presently described technology now will be described with respect to the appended figures; however, the scope of the present technology is not intended to be limited thereby. It is to be understood that the scope of the present technology is not to be limited to the specific embodiments described herein. The technology may be practiced other than as particularly described and still be within the scope of the claims.

FIG. 1 is a schematic view of a heat transfer system 100 according to an embodiment of the present technology. The heat transfer system 100 includes a heat transfer device 102, a heat exchanger 104, a heat transfer medium 106, and a network of tubular structures 108 for circulating the heat transfer medium 106 between the heat transfer device 102 and the heat exchanger 104.

The heat exchanger 104 is configured to heat or chill the heat transfer medium 106. The heat exchanger 104 may be any of a variety of conventionally designed heat exchanger 104s. For example the heat exchanger 104 may be a standard chiller, such as an RF-25 Recirculating Chiller manufactured by New Brunswick Scientific. The heat transfer medium 106 may be a gas, such as, for example, nitrous oxide, Freon, carbon dioxide, or nitrogen. Alternatively, the heat transfer medium 106 may be a liquid, such as, for example, water, saline, propylene glycol, ethylene glycol, or mixtures thereof. In other embodiments, the heat transfer medium 106 may be a slurry, such as, for example, a mixture of ice and salt. In still other embodiments, the heat transfer medium 106 may be a gel, such as, for example, a refrigerant gel. Alternatively, the heat transfer medium 106 may be a solid, such as, for example, ice or a heat conducting metal. For example, the heat transfer medium 106 may comprise a heating element, such as a wire or ribbon. Such a wire or ribbon may be straight or coiled and may comprise any metal or combination of metals, including those that are routinely used such as iron-chromium-aluminum wires, nichrome wires, and copper-nickel wires. Alternatively, the heat transfer medium 106 may comprise a cooling tube comprising a heat conducting metal. For example, the heat transfer medium 106 may comprise a copper tube. The copper tube may carry a refrigerant or blend comprising, for example, freon, hydrofluorocarbon, chlorofluorocarbon, or hydrochlorofluorocarbon. In yet another embodiment, a solid heat transfer medium 106 may comprise a carbon fiber, such as graphitic carbon fibers. In other embodiments, the heat transfer medium 106 may be formed, for example, by mixing a powder with a liquid. Thus, it should be understood that combinations and/or mixtures of the above-mentioned media may be employed to achieve a heat transfer medium 106 according to the present technology.

The network of tubular structures 108 for circulating the heat transfer medium 106 may include an external supply tube 110 and an external return tube 112. The external supply tube 110 defines an external supply lumen 114 providing a fluid path for flow of the heat transfer medium 106 from the heat exchanger 104 to the heat transfer device 102. The external return tube 112 defines an external return lumen 116 providing a fluid path for flow of the heat transfer medium 106 from the heat transfer device 102 to the heat exchanger 104. A pump 118 may be employed to circulate the heat transfer medium 106 through the network of tubular structures 108, and the flow rate of the medium, and, hence the heat transfer capabilities of the device, can be regulated by adjusting the pumping rate.

The heat transfer device 102 is adapted for placement within an anatomical structure of a mammalian patient. The heat transfer device 102 has a proximal and a distal end. The distal end of the heat transfer device 102 may be configured for insertion into a body orifice. For example, the distal end of the heat transfer device 102 may be configured for insertion into the nostrils, mouth, anus, or urethra of a patient. When properly inserted, the distal end of the heat transfer device 102 may be ultimately positioned in the esophagus, rectum, colon, bladder, or other anatomical structure. The proximal end of the heat transfer device 102 includes an input port 120 and an output port 122. The input port 120 and output port 122 are connected to the network of tubular structures 108 for circulating the heat transfer medium 106. For example, the input port 120 may be connected to the external supply tube 110 and the output port 122 may be connected to the external return tube 112. Thus, in certain embodiments, the heat exchanger 104 may be in fluid communication with the heat transfer device 102 via the network of tubular structures 108.

In operation, the heat transfer device 102 is positioned into an anatomical structure, such as the esophagus. The heat exchanger 104 is used to heat or chill the heat transfer medium 106 that is supplied to the heat transfer device 102 via the external supply tube 110. The heat transfer medium 106 flows through the external supply tube 110 and enters the heat transfer device 102 through the input port 120. The heat transfer medium 106 circulates through the heat transfer device 102 and exits the heat transfer device 102 through the output port 122, and returns to the heat exchanger 104 via the external return tube 112. Raising or lowering the temperature of the heat transfer medium 106 alters the body temperature of the patient.

The heat transfer system 100 may further incorporate a device that measures a physiological parameter such as temperature, pressure, or electromagnetic fluctuations. For example, the heat transfer system 100 may include one or more thermometers 124, each with one or more temperature probes 126, for measuring the ambient temperature, patient temperature, or heat transfer medium 106 temperature. The thermometers may be separate devices or integrated with the heat transfer system 100.

Figure 2:
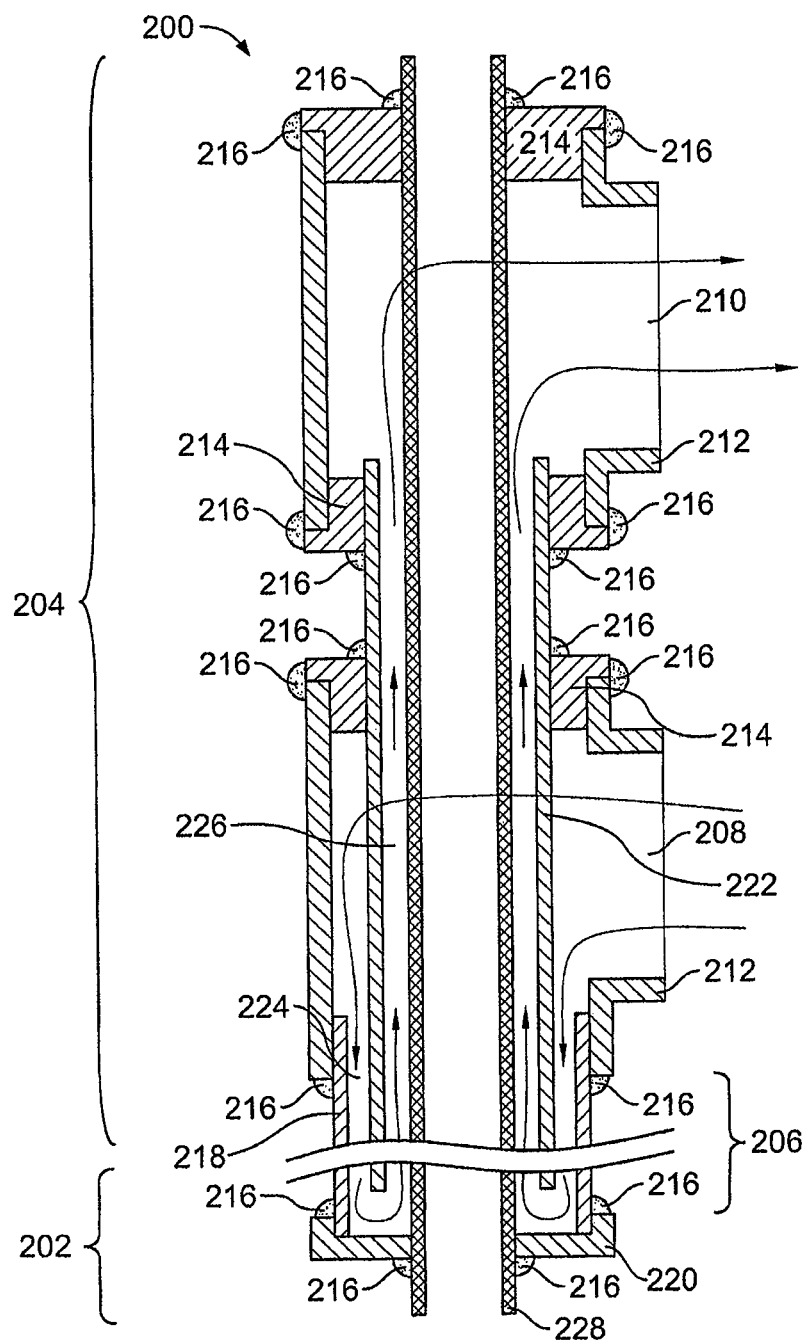
FIG. 2 depicts a heat transfer device according to an exemplary embodiment of the present technology.

FIG. 2 depicts a heat transfer device 200 according to an embodiment of the present technology. For purposes of further elucidating this embodiment, the heat exchanger will be referred to as a chiller (not shown) and the heat transfer medium will be referred to as a coolant. However, it should be understood that any suitable heat exchanger and any suitable heat transfer medium may be employed with the heat transfer device depicted in FIG. 2.

The heat transfer device 200 comprises a distal end 202, a proximal end 204, and a length of flexible tubing 206 extending therebetween. The proximal end 202 includes an input port 208 for receiving coolant from the chiller and an output port 210 allowing coolant to return to the chiller.

The input port 208 comprises a standard plumbing tee fitting 212. Alternatively, any fitting with two or more open ends, such as a wye fitting may be employed. The fitting may be composed of any suitable material, including, for example metal, such as, copper or iron; metal alloy, such as steel or brass; or plastic, such as, polyvinyl chloride ("PVC") or polyethylene ("PE"). A brass plug 214 is affixed to the proximal open end of the tee fitting 212. Alternatively, standard caps, such as metal or plastic caps, may be affixed to the proximal open end of the fitting. The plug 214 includes an opening to allow for tubing clearance. The plug 214 is affixed to the fitting with chemical sealant 216, such as, for example, Room-Temperature Vulcanization ("RTV") Silicone Sealant. In other embodiments, the input port 208 may be manufactured in a way that eliminates the need for affixed end caps, such as, for example, by extrusion.

The output port 210 comprises a standard plumbing tee fitting 212. Alternatively, any fitting with two or more open ends, such as a wye fitting may be employed. The fitting may be composed of any suitable material, including, for example metal, such as, copper or iron; metal alloy, such as steel or brass; or plastic, such as, PVC or PE. Brass plugs 214 are affixed to the proximal open end and distal open end of the tee fitting. Alternatively, standard caps, such as metal, metal alloy, or plastic caps, may be affixed to the open ends of the fitting. Each plug 214 may include an opening to allow for tubing clearance. The plugs 214 are affixed to the fitting with chemical sealant 216, such as, for example, RTV Silicone Sealant. In other embodiments, the output port 210 may be manufactured in a way that eliminates the need for affixed end caps, such as, for example, by extrusion.

The length of tubing 206 extending between the proximal end 204 and distal end 202 of the heat transfer device 200 is a coolant supply tube 218. The coolant supply tube 218 may be composed of clear vinyl. Alternatively, the coolant supply tube 218 may be composed of other suitable materials, such as, for example, flexible medical grade transparent PVC. The dimensions of the coolant supply tube 218 may be approximately 0.625" outside diameter ("OD")× 0.500" inside diameter ("ID"). The coolant supply tube 218 is affixed to the input port 208 with chemical sealant 216, such as, for example, RTV Silicone Sealant. The coolant supply tube 218 extends from the input port 208 to the distal end 202 of the heat transfer device 200. The length of the coolant supply tube 218 may be about eighteen (18) to about fifty-two (52) centimeters. In certain embodiments, the length of the coolant supply tube 218 may be from about eighteen (18) to about twenty-two (22) centimeters. In certain embodiments, the length of the coolant supply tube 218 may be from about thirty (30) to about forty-two (42) centimeters. In other embodiments, the length of the coolant supply tube 218 may be from about forty-five (45) to about fifty-two (52) centimeters. The length of the coolant supply tube 218 can be about thirty-two (32) centimeters.

The distal end 202 of the heat transfer device 200 includes an end cap 220. The end cap 220 may be composed of any suitable material, including, for example, metal, such as, copper or iron; metal alloy, such as steel or brass; or plastic, such as, PVC or PE. The end cap 220 is affixed to the coolant supply tube with chemical sealant 216, such as, for example, RTV Silicone Sealant.

A coolant return tube 222 may be positioned within the coolant supply tube 218. The coolant return tube 222 may be composed of clear vinyl. Alternatively, the coolant return tube 222 may be composed of other suitable materials, such as, for example, flexible medical grade transparent PVC. The outside diameter of the coolant return tube 222 is smaller than the inside diameter of the coolant supply tube 218. For example, the dimensions of the coolant return tube 222 may be approximately 0.437" outside diameter ("OD")× 0.312" inside diameter ("ID"). The coolant return tube 222 may be affixed to one or both of the input port 208 or output port 210 with chemical sealant 216, such as, for example, RTV Silicone Sealant.

The coolant return tube 222 does not extend to the end cap 220 at the distal end 202 of the heat transfer device 200. Thus, the lumen of the coolant supply tube 224 and the lumen of the coolant return tube 226 may be in fluid communication with each other, thereby defining a fluid path for coolant flow.

In operation, the coolant enters the input port 208 and flows through the lumen of the coolant supply tube 224 to the distal end 202 of the heat transfer device 200, which may be positioned in, for example, the esophagus of a patient. The coolant then flows through the lumen of the coolant return tube 226 to the output port 210. In operation, heat is transferred from, for example, the esophagus to the coolant, resulting in a decrease in the temperature of the esophagus, as well as adjacent organs, and ultimately, systemic hypothermia.

In certain embodiments, additives with high heat transfer coefficient, such as copper, for example, may be added to the material used for manufacture of the coolant supply tube 218 or the coolant return tube 222. In one embodiment, lengths of wire, for example, running linearly or spiraling along the length of the tube may be included. In other embodiments, particulate matter with a high heat transfer coefficient may be mixed in to the material used for manufacture of the coolant supply tube 218 or the coolant return tube 222 (for example, vinyl or PVC) before or during extrusion.

In certain embodiments, the walls of the coolant supply tube 218 and/or coolant return tube 222 may be relatively thin. For example, the wall of the coolant supply tube 218 may be less than about 1 millimeter. Alternatively, the wall of the coolant supply tube 218 may be less than about 0.01 millimeter. In some embodiments, the wall of the coolant supply tube 218 may be less than about 0.008 millimeters. As will be appreciated by one of skill in the art, the thickness of the walls of the heat transfer medium supply tube and/or heat transfer medium return tube may be modified in increments of about 0.001 millimeters, about 0.01 millimeters, or about 0.1 millimeters, for example.

Optionally, the heat transfer device 200 may include a gastric tube 228, to allow for gastric access and, for example, gastric suctioning as well as gastric lavage for diagnosis and/or therapeutic purposes, if so desired. The gastric tube 228 may be composed of clear vinyl. Alternatively, the gastric tube 228 may be composed of other suitable materials, such as, for example, flexible medical grade transparent PVC. The outside diameter of the gastric tube 228 is smaller than the inside diameter of the coolant return tube 222. For example, the dimensions of the gastric tube 228 may be approximately 0.250" outside diameter ("OD")×0.170" inside diameter ("ID"). The gastric tube 228 may be affixed to the most proximal port, either the input port 208 or the output port 210, with chemical sealant 216, such as, for example, RTV Silicone Sealant. The gastric tube 228 may allow the patient's health care provider to insert, for example, a nasogastric tube that allows for suctioning of the gastric contents. Alternatively, the gastric tube 228 may allow the patient's health care provider to insert, for example, a gastric temperature probe (not shown).

Optionally, an antibiotic or antibacterial coating may be applied to portions of the coolant supply tube 218, the coolant return tube 222, or the gastric tube 228. Particularly, an antibiotic or antibacterial coating may be applied to portions of the tubes that, upon insertion to a patient, may contact, for example, a mucosal lining of the patient. For example, topical antibiotics, such as tobramycin, colistin, amphotericin B, or combinations thereof, may be applied to the tubes. Incorporation of an antibiotic or antibacterial coating may allow selective decontamination of the digestive tract ("SDD"), which may further improve outcome.

As another alternative, all or part of the heat transfer device 200 can be manufactured by, for example, extrusion. Employing such a manufacturing modality would eliminate the need to seal junctions or affix end caps and reduce the points at which leaks may occur.

Figure 3B:
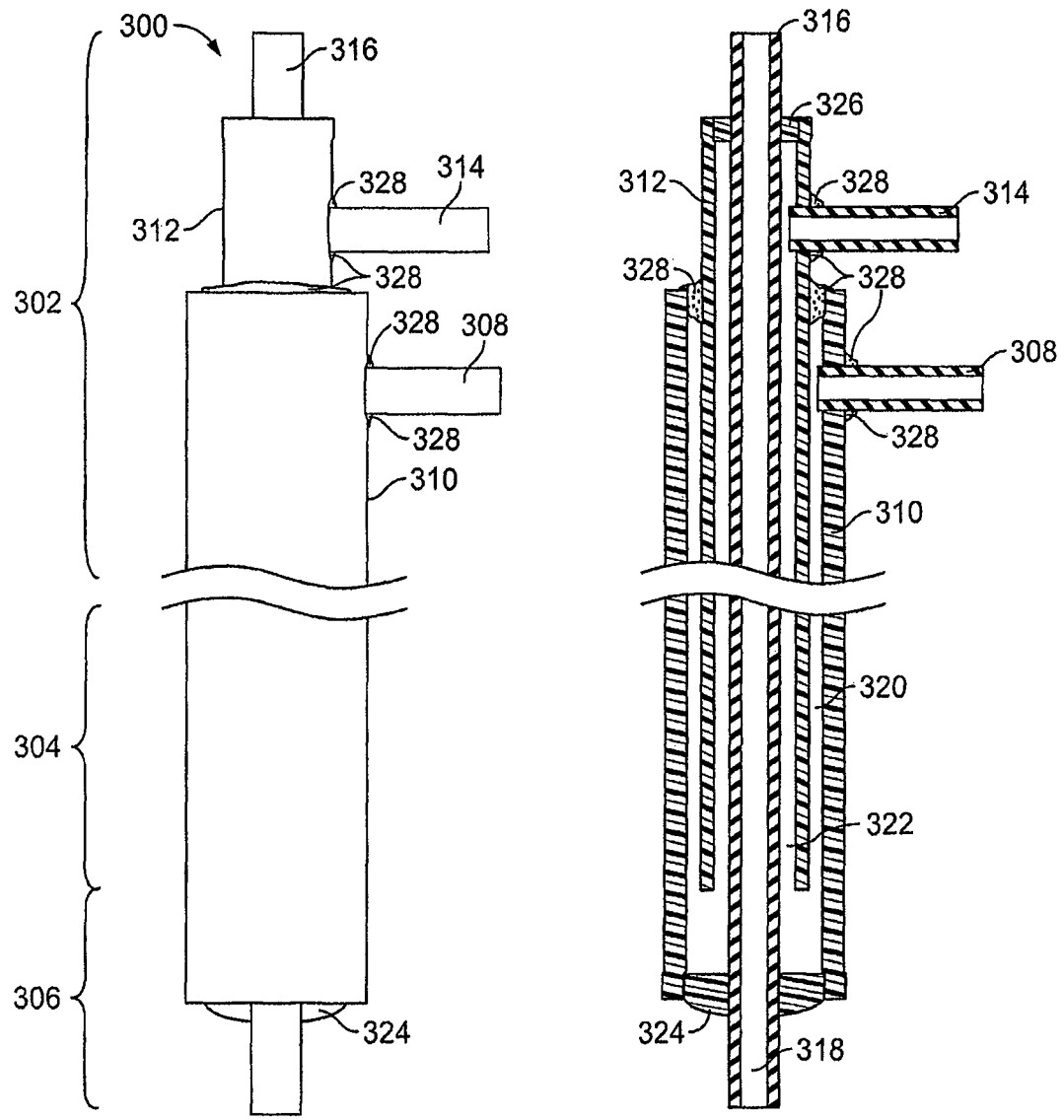
FIG. 3B shows a top down view of a heat transfer device according to an exemplary embodiment of the present technology.
Figure 3B:
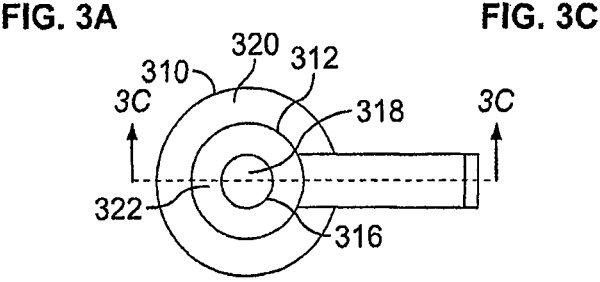

FIG. 3 depicts a heat transfer device 300 according to an embodiment of the present technology. The heat transfer device 300 comprises a proximal end 302, a distal end 306, and a length of flexible tubing 304 extending therebetween.

All or part of the heat transfer device 300 can be manufactured by, for example, extrusion. Employing such a manufacturing modality would eliminate the need to seal junctions or affix end caps and reduce the points at which leaks may occur. Alternatively, or additionally, a fast curing adhesive, such as RTV silicone sealant or temperature-curable sealant can be used to seal junctions and/or bond tubing together. The heat transfer device 300 can be constructed using a biocompatible elastomer and/or plastic, and, optionally, adhesive. For example, biomedical grade extruded silicone rubber such as Dow Corning Q7 4765 silicone, and an adhesive such as Nusil Med2-4213 can be used to manufacture heat transfer device 300.

FIG. 3A shows a schematic view of the exterior of heat transfer device 300. The heat transfer device 300 includes an input port 308, a heat transfer medium supply tube 310, a heat transfer medium return tube 312, and an output port 314. In one embodiment, the outer wall of the heat transfer medium supply tube 310 can be in direct contact with patient tissue upon placement of the heat transfer device 300 in a patient. For example, the outer wall of heat transfer medium supply tube 310 can be in direct contact with the patient's esophagus when the heat transfer device 300 is inserted orally or nasally. The portion of the heat transfer medium supply tube 310 that can be in direct contact with patient tissue can be part of the heat transfer region of the heat transfer device 300. Input port 308 is connected to the heat transfer medium supply tube 310 and allows for heat transfer medium to be delivered to the lumen of the heat transfer medium supply tube 310. Input port 308 may be positioned along the length of the heat transfer medium supply tube 310, preferably proximal to the region of the heat transfer medium supply tube 310 that is capable of directly contacting the patient tissue. Heat transfer medium may flow through the heat transfer medium supply tube 310 to the heat transfer medium return tube 312. Output port 314 is connected to the heat transfer medium return tube 312 and may allow for heat transfer medium to exit the device. Output port 314 may be positioned along the length of the heat transfer medium return tube 312, preferably proximal to the heat transfer region of heat transfer device 300. The heat transfer device also includes a central tube 316 that, for example, allows for gastric access. The central tube 316 is in a concentric arrangement with the heat transfer medium supply tube 310 or the heat transfer medium return tube 312 (see FIG. 3B). The central tube lumen 318 provides the health care professional with access to, for example, the patient's stomach while the heat transfer device is positioned within the patient's esophagus.

FIG. 3C is a cross-sectional view along the line 3C, which is identified in FIG. 3B.

The outermost tube is the heat transfer medium supply tube 310. The heat transfer medium supply tube 310 extends from about the input port 308 to about the distal end 306 of the heat transfer device 300. The length of the heat transfer medium supply tube 310 can be about eighteen (18) to about seventy-five (75) centimeters. In a particular embodiment, the length of the heat transfer medium supply tube 310 is about thirty-two (32) centimeters. The outside diameter of the heat transfer medium supply tube 310 can be, for example, about 1.0 to about 2.0 centimeters. In a particular embodiment, the outside diameter of the heat transfer medium supply tube 310 is about 1.4 centimeters.

Upon insertion into, for example, the esophagus of a patient, the wall of the heat transfer medium supply tube 310 can be in direct contact with the patient's esophagus. As noted above, the length and/or circumference of the heat transfer medium supply tube 310, and therefore the surface area of heat transfer medium supply tube 310, can vary. Increasing the area of contact between the heat transfer device 300 and the patient's esophagus improves the speed and efficiency at which the patient is cooled or heated (or re-warmed). In certain embodiments the surface area of the heat transfer medium supply tube 310 can be from about 50 $cm^2$ to about 350 $cm^2$. In a particular embodiment, the surface area of the heat transfer region of the heat transfer medium supply tube 310 can be about 140 $cm^2$. In certain embodiments, the heat transfer medium supply tube 310 can contact substantially all of the epithelial surface of a patient's esophagus.

Positioned within the heat transfer medium supply tube 310 is the heat transfer medium return tube 312. The outside diameter of the heat transfer medium return tube 312 is smaller than the inside diameter of the heat transfer medium supply tube 310. The heat transfer medium return tube 312 does not extend to the distal end of the heat transfer medium supply tube 310. Thus, the heat transfer medium supply tube lumen 320 and the heat transfer medium return tube lumen 322 are in fluid communication with each other, thereby defining a fluid path for the flow of the heat transfer medium.

Positioned within the heat transfer medium return tube is the central tube 316. The outside diameter of the central tube 316 is smaller than the inside diameter of the heat transfer medium return tube 312. The central tube 316 can be, for example, a gastric tube, to allow for gastric access. The central tube 316 can act as a gastric tube that, for example, allows for suctioning of the gastric contents. The central tube 316 also allows a health care professional to insert, for example, a nasogastric tube that allows for suctioning of the gastric contents. Alternatively, the central tube 316 allows a health care professional to insert, for example, a gastric temperature probe.

The distal end of the heat transfer medium supply tube 310 can be sealed with an end cap 324. The end cap 324 can be constructed from, for example, silicone. The end cap 324 can include a hole or other passageway through which central tube 316 can pass. Likewise, the proximal end of the heat transfer medium return tube 312 can be sealed with an end cap 326. The end cap 326 can be constructed from, for example, silicone. The end cap 326 can include a hole or other passageway through which central tube 316 can pass. Junctions between the various components and tubes can be sealed with a sealant 328, such as Nusil Med2-4213.

Figure 4:
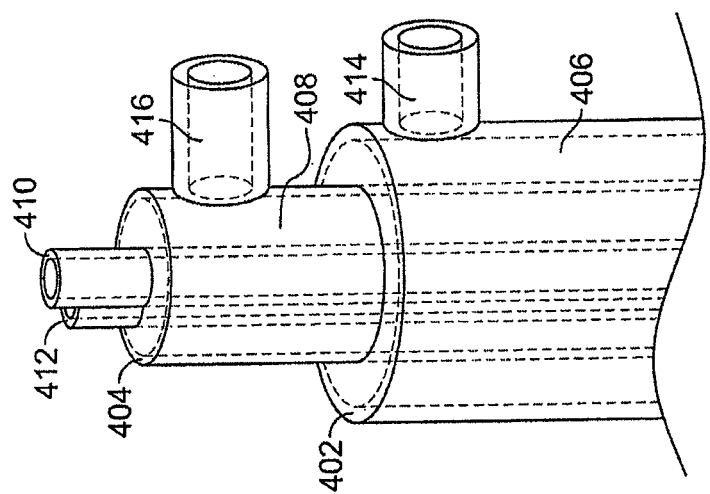
FIG. 4 shows a schematic view of a proximal end of a heat transfer device according to an exemplary embodiment of the present technology.

FIG. 4 shows several views of a proximal end of a heat transfer device according to the present technology.

The heat transfer device comprises at least two concentrically arranged tubes, such as a heat transfer supply tube 402 and a heat transfer return tube 404, forming a multi-lumen heat transfer device having a generally coaxial lumen configuration. The proximal ends of each of the heat transfer supply tube 402 and the heat transfer return tube 404 can be sealed with end caps (not shown). The heat transfer device, optionally, includes a first central tube 410 and/or a second central tube 412. For example, the heat transfer device can comprise one or more gastric tubes.

The heat transfer supply tube lumen 406 is of sufficient diameter to allow passage of the heat transfer return tube 404. Likewise, the heat transfer return tube lumen 408 may be of sufficient diameter to allow passage of the first central tube 410 and/or the second central tube 412. The first central tube 410 and the second central tube 412 can be for example gastric tubes that provide access to the patient's stomach and allow for suctioning of gastric contents and/or placement of a gastric temperature probe. The end cap (not shown) of the heat transfer return tube 404 can include a hole or other passageway through which central tubes 410 and 412 pass.

The heat transfer supply tube 402 may be coupled to an input port 414. Preferably, input port 414 is in a position such that upon insertion of the device, input port 414 remains external to the patient. The input port 414 may be coupled to an external supply tube (not shown) equipped with standard connectors for interface with a chiller and/or warming device. The heat transfer return tube 404 may be coupled to an output port 416. Preferably, output port 416 is in a position such that upon insertion of the device, output port 416 remains external to the patient. The output port 416 may be coupled to an external return tube (not shown) equipped with standard connectors for interface with the chiller and/or warming device.

FIG. 5 shows schematic and cross-section views of a distal end of a heat transfer device according to the present technology.

Figure 5A:
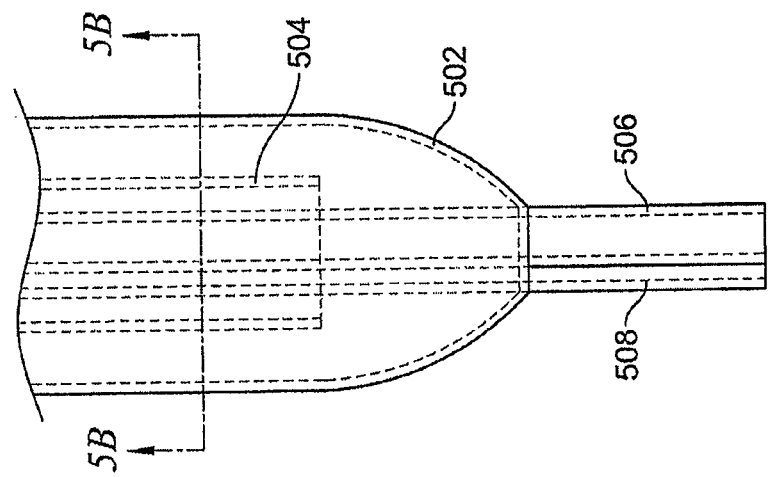
FIG. 5A shows a schematic view of a distal end of a heat transfer device according to an exemplary embodiment of the present technology.

The heat transfer device as depicted in FIG. 5A comprises at least two concentrically arranged tubes, such as a heat transfer supply tube 502 and a heat transfer return tube 504, to form a multi-lumen heat transfer device having a generally coaxial lumen configuration. The distal end of the heat transfer supply tube 502 extends beyond the distal end of heat transfer return tube 504 such that the heat transfer supply tube 502 and heat transfer return tube 504 form a heat transfer flow path. The distal end of the heat transfer supply tube 502 can be rounded or otherwise formed to facilitate insertion and positioning of the heat transfer device in the patient's esophagus. The heat transfer device can also comprise a first central tube 506 and/or a second central tube 508. The first central tube 506 and the second central tube 508 can be, for example gastric tubes that provide access to the patient's stomach and allow for suctioning of gastric contents and/or placement of a gastric temperature probe.

Figure 5B:
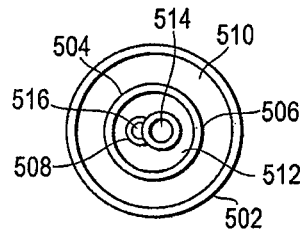
FIGS. 5B-5Q show several cross-sectional views and corresponding schematic views of a distal end of a heat transfer device according to an exemplary embodiment of the present technology.
Figure 5J:
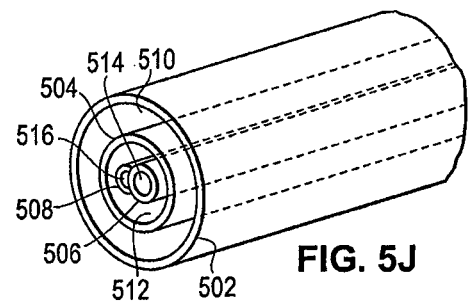

FIG. 5B is a cross-sectional view along the line 5B, which is identified in FIG. 5A. The heat transfer supply tube 502 and the heat transfer return tube 504 are arranged concentrically. The heat transfer return tube 504 is positioned within the heat transfer supply tube lumen 510. The first central tube 506 and the second central tube 508 are positioned within the heat transfer return tube lumen 512. A health care professional can, for example, insert a gastric temperature probe (not shown) through the first central tube lumen 514 and/or the second central tube lumen 516.

Figure 5C:
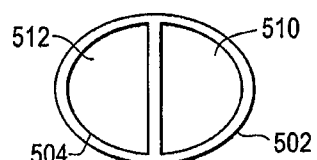
Figure 5K:
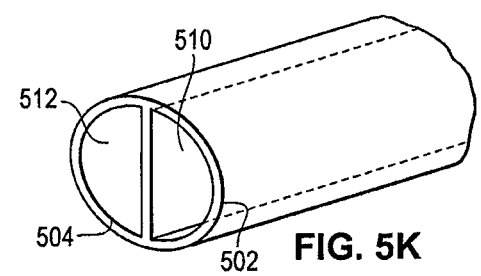
Figure 5D:
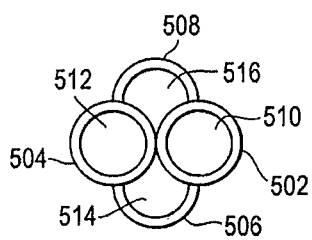
Figure 5L:
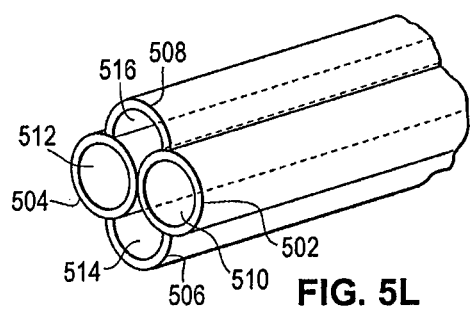
Figure 5E:
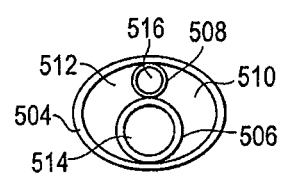
Figure 5M:
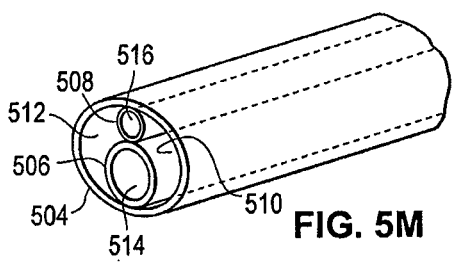
Figure 5F:
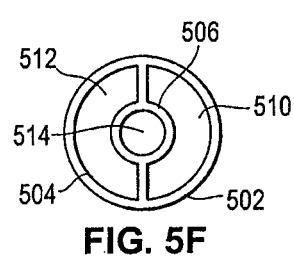
Figure 5N:
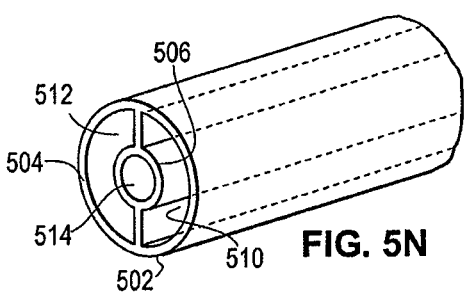
Figure 5G:
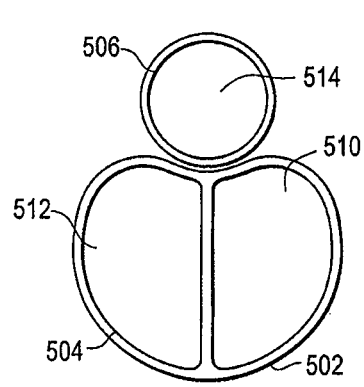
Figure 5O:
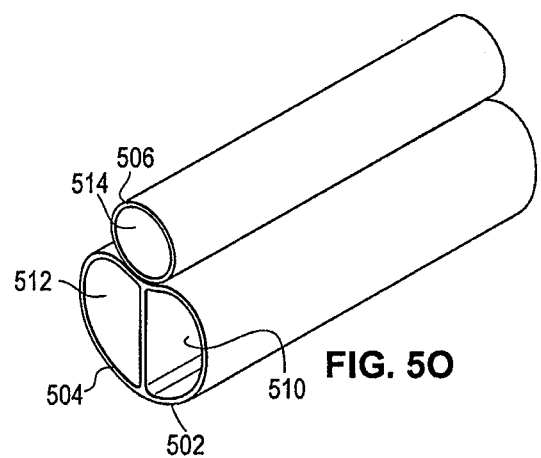
Figure 5H:
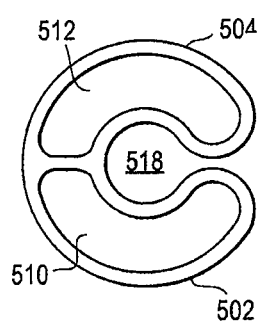
Figure 5P:
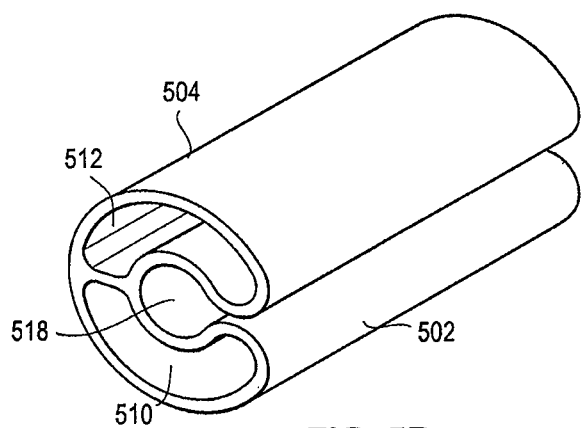
Figure 5I:
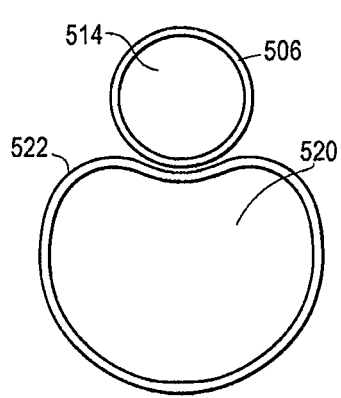
Figure 5Q:
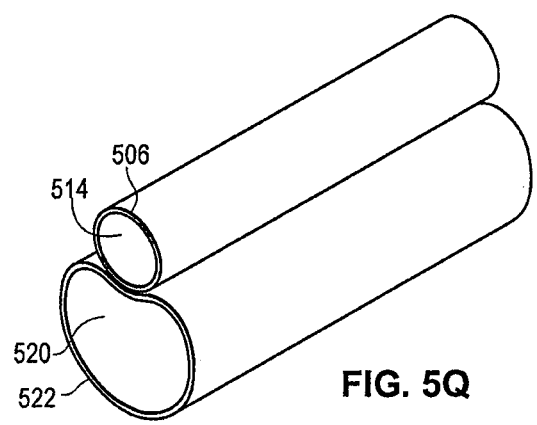

FIGS. 5B-5Q depict additional arrangements of the tubes and lumens that comprise exemplary heat transfer devices and systems of the present technology. FIGS. 5B-5Q show cross-sectional (FIGS. 5B-5I), and corresponding schematic (5J-5Q), views of several alternative configurations of multi-lumen and single-lumen heat transfer devices and/or systems according to embodiments of the present technology.

As shown in FIG. 5C and corresponding FIG. 5K, the heat transfer supply tube lumen 510 and the heat transfer return tube lumen 512 can be arranged in parallel to each other. As shown in FIG. 5D and corresponding FIG. 5L, the first central tube lumen 514 and the second central tube lumen 516 can also be arranged in parallel to the heat transfer supply tube lumen 510 and the heat transfer return tube lumen 512. Alternatively and as shown in FIGS. 5E and 5F, and corresponding FIGS. 5M and 5N, the first central tube lumen 514 and/or the second central tube lumen 516 can be positioned between the heat transfer supply tube lumen 510 and the heat transfer return tube lumen 512. In yet another alternative and as shown in FIG. 5G and corresponding FIG. 5O, the first central tube lumen 514 can abut and run in parallel to the heat transfer supply tube 502 and/or the heat transfer return tube 504. Optionally, a gastric tube or a gastric probe can be inserted into a patient's stomach via the first central tube lumen 514 and/or the second central tube lumen 516. In some embodiments, a commercially available tube, such as a nasogastric tube or an orogastric tube, can be inserted into the patient's stomach via the first central tube lumen 514 and/or the second central tube lumen 516. Such tubes are well known to those of skill in the art. In certain embodiments, the first central tube 506 and/or the second central tube 508 serve as a gastric tube and the need to place a separate nasogastric or orogastric tube is eliminated.

As shown in FIG. 5H and corresponding FIG. 5P, heat transfer supply tube 502 defining the heat transfer supply tube lumen 510 and the heat transfer return tube 504 defining the heat transfer return tube lumen 512 can be arranged to form a C-shape, defining a central interior 518. In embodiments such as an esophageal heat transfer device, the C-shaped design can allow for gastric access. For example, the C-shaped design allows for the use of a commercially available probe, such as a temperature probe, or tube, such as a nasogastric tube or an orogastric tube, with the heat transfer device. The nasogastric tube, orogastric tube, or probe (not shown) may be placed within the central interior 518 of the C-shape formed by the heat transfer supply tube 502 and the heat transfer return tube 504. The nasogastric tube, orogastric tube, or probe (not shown) may be provided with the heat transfer device or provided as an after-market component.

As shown in FIG. 5I and corresponding FIG. 5Q, a heat transfer device may comprise a single heat transfer lumen 520 defined by heat transfer tube 522. The single heat transfer lumen 520 may serve as the heat transfer supply tube lumen 510 and the heat transfer return tube lumen 512. For example, heat transfer medium may be delivered to a heat transfer region of the device and extracted from the heat transfer region via the single heat transfer lumen 520 by, for example, an external pump (not shown) that alternatively pumps and withdraws heat transfer medium via the single lumen. In certain other embodiments, a solid heat transfer medium, which may comprise a heating element such as a wire or coil; a thermoelectric module such as a Peltier module; or a carbon fiber such as a graphitic carbon fiber, may be inserted into the single heat transfer lumen 520. Optionally, at least one central tube 506 defining at least one central lumen 514 can abut and run in parallel to heat transfer tube 522. The central tube 506 can be, for example a gastric tube that provides access to the patient's stomach and allows for suctioning of gastric contents and/or placement of a gastric temperature probe. A gastric tube, such as a nasogastric or orogastric tube, or a gastric probe can be inserted into a patient's stomach via the central tube lumen 514. Alternatively, the central tube 506 can serve as a gastric tube and the need to place a separate nasogastric or orogastric tube is eliminated.

The esophageal heat transfer device shown in FIGS. 2-5 and further discussed herein above is merely exemplary and not meant to be limiting to the present technology. The heat transfer device of the present technology may be configured for insertion into the ears, nostrils, mouth, anus, or urethra of a patient. When properly inserted, the heat transfer portion of the device may be ultimately positioned in the auricular canal, nasopharynx, esophagus, stomach, rectum, colon, bladder, or other anatomical structure.

FIG. 6 depicts a cross-sectional and longitudinal view of heat transfer device 600 according to an embodiment of the present technology.

Figure 6A:
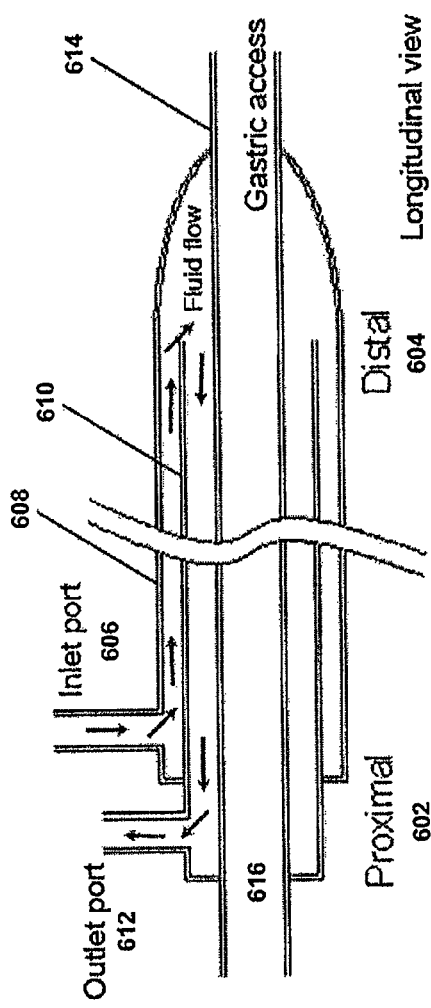
FIG. 6A of a heat transfer device according to an exemplary embodiment of the present technology.

FIG. 6A depicts a longitudinal view of heat transfer device 600 according to an embodiment of the present technology. The heat transfer device 600 comprises a proximal end 602 and a distal end 604. The heat transfer device 600 includes an inlet port 606, a heat transfer medium supply tube 608, a heat transfer medium return tube 610, and an outlet port 612. The distal end of the heat transfer medium supply tube 608 extends beyond the distal end of heat transfer medium return tube 610 such that the heat transfer medium supply tube 608 and heat transfer medium return tube 610 form a heat transfer medium flow path. The heat transfer device also includes a central tube 614 that, for example, allows for gastric access. The central tube 614 is in a concentric arrangement with the heat transfer medium supply tube 608 or the heat transfer medium return tube 610 or both, to form a multi-lumen heat transfer device having a generally coaxial lumen configuration. The central tube 614 can be, for example, a gastric tube that provides access to the patient's stomach and allows for suctioning of gastric contents and/or placement of a gastric temperature probe. The central tube lumen 616 provides the health care professional with access to, for example, the patient's stomach while the heat transfer device is positioned within the patient's esophagus.

Figure 6B:
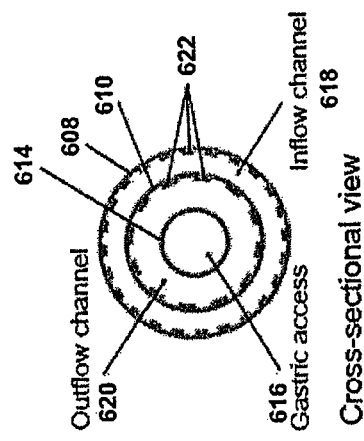
FIG. 6B shows a longitudinal view and a cross-sectional view of a heat transfer device according to an exemplary embodiment of the present technology.

FIG. 6B depicts a cross-sectional view of heat transfer device 600 according to an embodiment of the present technology. The heat transfer medium supply tube 608 and the heat transfer medium return tube 610 are arranged concentrically. The heat transfer medium return tube 610 is positioned within the inflow channel 618, which is defined by heat transfer medium supply tube 608. The central tube 614 is positioned within outflow channel 620, which is defined by heat transfer medium return tube 610. A health care professional can, for example, insert a gastric temperature probe (not shown) through the central tube lumen 616. The heat transfer medium supply tube 608 and the heat transfer medium return tube 610 have inner surfaces comprised of a plurality of splines 622. The plurality of splines 622 surround the heat transfer medium flow path, thereby helping to enhance the likelihood of maintenance of laminar flow, and reduce the likelihood of flow obstruction.

Figure 7:
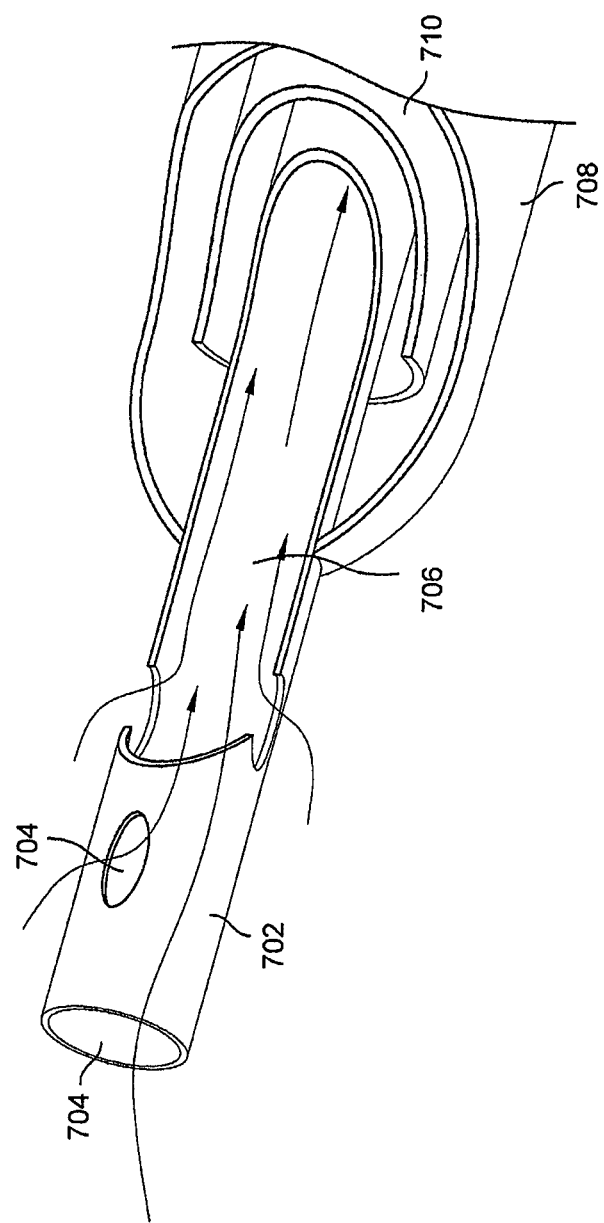
FIG. 7 is a schematic diagram of a distal end of a heat transfer device according to an exemplary embodiment of the present technology.

FIG. 7 depicts a schematic view of a distal end of a heat transfer device according to an embodiment of the present technology.

In certain embodiments, an esophageal heat transfer device incorporates a gastric tube 702. The gastric tube 702 may be the center tube of the concentric arrangement of tubes and may comprise a generally hollow tube that provides gastric access. For example, a tube that allows for suctioning of the gastric contents may be inserted into the patient's stomach via the gastric tube 702. In certain embodiments a commercially available tube, such as a nasogastric tube or an orogastric tube, can be inserted into the patient's stomach via the gastric tube 702. Such tubes are well known to those of skill in the art. In certain embodiments, the gastric tube 702 serves as a tube for suctioning stomach contents and the need to place a separate nasogastric tube is eliminated. As another example, a gastric temperature probe may be inserted via the gastric tube 702.

The gastric tube 702 may include several ports 704 that serve as small tubular connections or passageways from the external environment (here, the patient's stomach) to gastric tube lumen 706. The ports 704 may communicate directly (and only) with the gastric tube lumen 706. The ports 704 may be positioned at the distal end of the heat transfer device to provide additional communication portals between the patient's stomach and the gastric tube 702. The ports 704 provide for additional passageways for gastric contents to flow from the patient's stomach out through the gastric tube lumen 706, thereby reducing the likelihood of blockage of the single lumen from semi-solid stomach contents.

In other embodiments, an esophago-gastric heat transfer device comprises concentric tubes such that the center-most tube serves as a gastric tube 702. In such an arrangement, the outermost tube can be, for example, a heat transfer medium supply tube 708. A heat transfer medium return tube 710 can be positioned within the heat transfer medium supply tube 708. Likewise, the gastric tube 702 can be positioned within the heat transfer medium return tube 710.

As shown in FIG. 7, the heat transfer device may be an esophageal or esophago-gastric heat transfer device and comprise three concentrically arranged tubes, including a heat transfer medium supply tube 708, a heat transfer medium return tube 710, and a gastric tube 702 to form a multi-lumen heat transfer device having a generally coaxial lumen configuration. The heat transfer portion of the heat transfer device may be confined to the patient's esophagus, while the gastric tube 702 extends into the patient's stomach.

The heat transfer device may further include ports 704 along the side of the gastric tube 702. The distal end of the gastric tube 702 includes several ports along the side of the tube to provide access to the gastric tube lumen 706, thereby reducing the likelihood of blockage of the single lumen from semi-solid stomach contents. The addition of such ports 704 may improve and enhance the removal of stomach contents, which, in turn, may improve contact between gastric mucosa and the heat transfer device. Such improved contact may enhance heat transfer between the heat transfer device and the gastric mucosa.

The configuration of the ports as shown in FIG. 7 is oval. However, the ports can be, for example, circular, rectangular, or any other shape that permits flow of gastric contents from the stomach to the gastric tube lumen 706.

FIG. 8 depicts a heat transfer device 800 according to an embodiment of the present technology. The heat transfer device 800 comprises a proximal end 802, a distal end 806, and a length of flexible tubing 804 extending therebetween. The length of flexible tubing 804 may comprise a heat transfer region. The distal end 806 of the heat transfer device 800 may be configured for insertion into a body orifice. For example, the distal end 806 of the heat transfer device 800 may be configured for insertion into the nostrils or mouth of a patient. When properly inserted, the heat transfer region of the heat transfer device 800 may be ultimately positioned in the esophagus, or other anatomical structure. Upon placement in, for example, the esophagus of a patient, the heat transfer region of the heat transfer device 800 can be in direct contact with the patient's esophagus. In certain embodiments, the heat transfer region of the heat transfer device 800 can contact substantially all of the epithelial surface of a patient's esophagus. The distal end 806 of the heat transfer device 800 may be configured to extend into a stomach of a patient.

All or part of the heat transfer device 800 can be manufactured by, for example, extrusion. Employing such a manufacturing modality would eliminate the need to seal junctions or affix end caps and reduce the points at which leaks may occur. Alternatively, or additionally, a fast curing adhesive, such as RTV silicone sealant or temperature-curable sealant can be used to seal junctions and/or bond tubing together. The heat transfer device 800 can be constructed using a biocompatible elastomer and/or plastic, and, optionally, adhesive. For example, biomedical grade extruded silicone rubber such as silicone rubber available from Dow Corning (e.g., Q7-4765, C6-165, and/or C6-550), and an adhesive such as Nusil Med2-4213 can be used to manufacture heat transfer device 800.

FIG. 8A shows a schematic view of the exterior of heat transfer device 800. The heat transfer device 800 includes an input port 808 and an output port 810. The heat transfer device 800 includes a gastric tube 812 that, for example, allows for gastric access. The proximal end of the gastric tube can be adapted to accommodate attachment to, for example, a suctioning device.

Figure 8C:
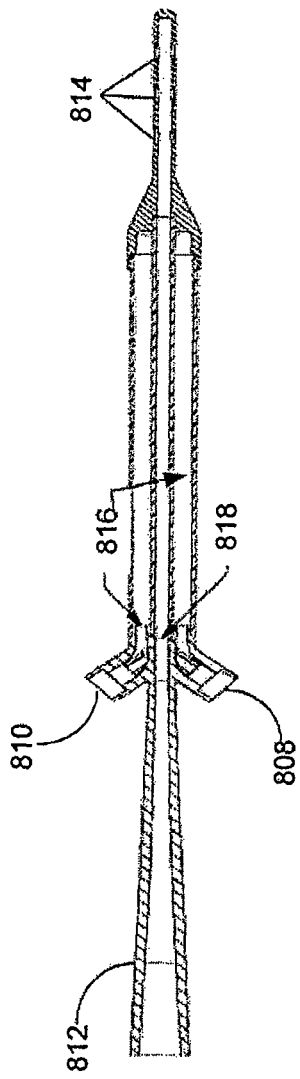
FIGS. 8C and 8D show cross-sectional views of a heat transfer device according to an exemplary embodiment of the present technology.

FIG. 8C is a cross-sectional view of the heat transfer device 800. The heat transfer device 800 comprises an internal cavity 816 and a gastric tube 812. The gastric tube 812 defines a gastric lumen 818. As shown in FIGS. 8B and 8C, the distal end 806 of the heat transfer device 800 includes one or more ports 814 along the side of the gastric tube 812. The ports 814 may provide for communication between the space exterior to the device 800 and the gastric tube lumen 818. For example, the ports 814 may act as a portal between the patient's stomach and the gastric tube lumen 818 allowing the gastric contents to be suctioned from the patient's stomach out through the gastric tube lumen 818. The presence of multiple ports 814 provides reduced likelihood of blockage of the gastric tube lumen 818 from semi-solid stomach contents. Alternatively, multiple gastric tube lumens may be employed. The addition of ports 814 may improve and enhance the removal of stomach contents, which, in turn, may improve contact between gastric mucosa and the heat transfer device 800. Such improved contact may enhance heat transfer between the heat transfer device 800 and the gastric mucosa. The configuration of the ports 814 shown in FIG. 8 is oval. However, the ports 814 can be, for example, circular, rectangular, or any other shape that permits flow of gastric contents from the stomach to the gastric tube lumen 818.

Figure 8D:
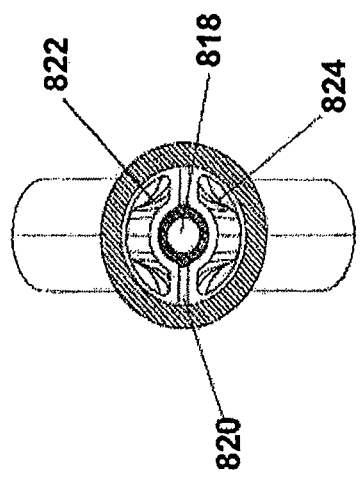
Figure 9A:
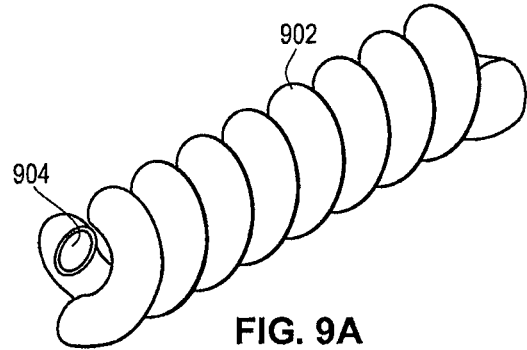
FIG. 9A is a perspective view of a portion of an exemplary heat transfer device.
Figure 9B:
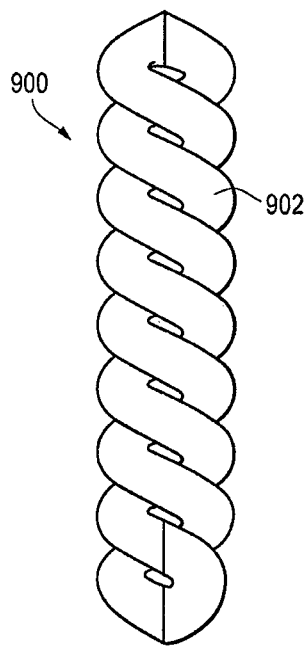
FIG. 9B is a longitudinal front side view of a portion of an exemplary heat transfer device.
Figure 9C:
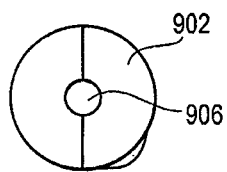
FIG. 9C is a bottom side view of a portion of an exemplary heat transfer device.
Figure 9D:
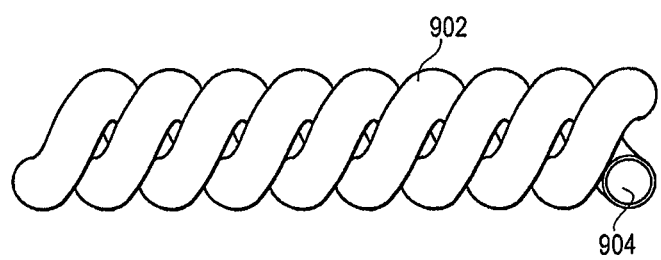
FIG. 9D is a horizontal front side view of a portion of an exemplary heat transfer device.

FIG. 8D is a cross-sectional view of the heat transfer device 800 along the line D-D shown in FIG. 8A. The internal cavity 816 can be divided by wall 820 into a multi-lumen cavity comprising, for example, a heat transfer medium supply lumen 822 and a heat transfer medium return lumen 824. The heat transfer medium supply tube lumen 822 and the heat transfer medium return tube lumen 824 may be in fluid communication with each other, thereby defining a fluid path for the flow of the heat transfer medium.

The gastric lumen 818 is in a concentric arrangement with the interior cavity 816. As discussed above, the gastric tube lumen 818 provides the health care professional with access to, for example, the patient's stomach while the heat transfer device 800 is positioned within the patient's esophagus.

FIGS. 9A-9D depict schematic representations of a portion of an exemplary heat transfer device according to the present technology. The portion of the heat transfer device represents all or part of a heat transfer region 900. The heat transfer region 900 comprises a tube 902 having a substantially helical configuration. The tube 902 defines an internal lumen 904, which is capable of receiving a heat transfer medium. For example, the internal lumen 904 may provide a fluid path for the flow of a liquid or gaseous heat transfer medium. In one embodiment, the tube 902 may serve as the evaporative component of a freon/gas circuit and be connected with an external condenser (not shown). Alternatively, the internal lumen 904 may be capable of receiving a solid or semi-solid heat transfer medium.

The substantially helical configuration of the tube 902 creates an interior space 906 defined by the helix, which serves as, for example, an access lumen. The access lumen allows for access to anatomical sites beyond the placement of the heat transfer device. For example, where the heat transfer device is for placement within the esophagus, the helical arrangement allows for gastric access via the interior space 906, which serves as, for example, a gastric access lumen. The helical design allows for the use of a commercially available probe, such as a temperature probe, or tube, such as a nasogastric tube or an orogastric tube, with the heat transfer device. The nasogastric tube, orogastric tube, or probe (not shown) may be placed within the interior 906. The nasogastric tube, orogastric tube, or probe (not shown) may be provided with the heat transfer device or provided as an after-market component.

In certain embodiments, the term "patient" refers to a mammal in need of therapy for a condition, disease, or disorder or the symptoms associated therewith. The term "patient" includes dogs, cats, pigs, cows, sheep, goats, horses, rats, mice and humans. The term "patient" does not exclude an individual that is normal in all respects.

As used herein, the term "treating" refers to abrogating; preventing; substantially inhibiting, slowing or reversing the progression of; substantially ameliorating clinical and/or non-clinical symptoms of; or substantially preventing or delaying the appearance of clinical and/or non-clinical symptoms of a disease, disorder or condition.

In the preceding paragraphs, use of the singular may include the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

Likewise, the following examples are presented in order to more fully illustrate the present technology. They should in no way be construed, however, as limiting the broad scope of the technology disclosed herein.

EXAMPLES

Example 1: Cooling of a Model System

Figure 10:
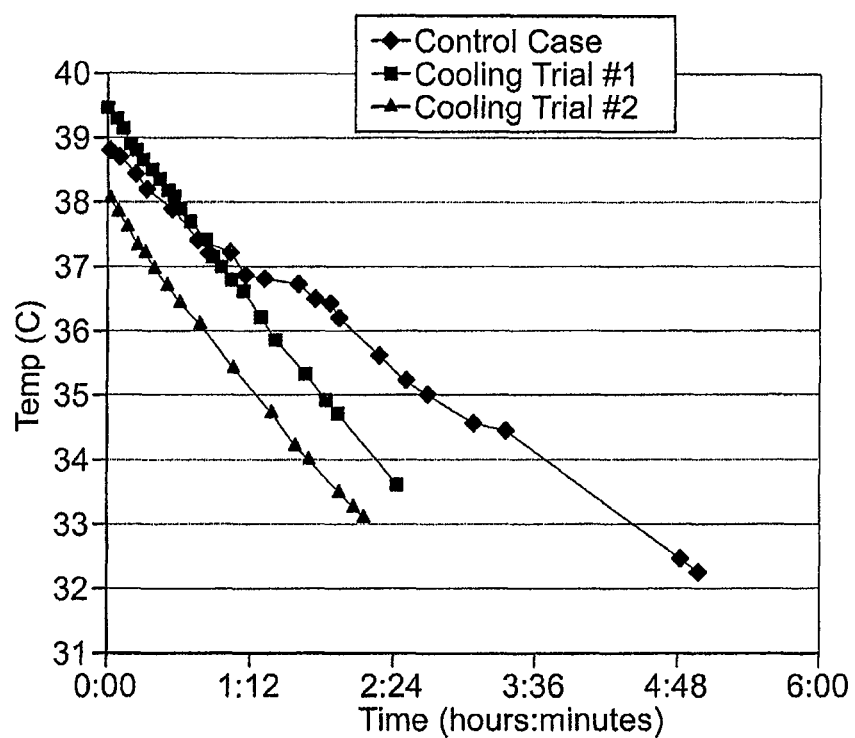
FIG. 10 is a graph depicting the cooling achieved with an exemplary cooling device according to an embodiment of the present technology.

An experiment was conducted to quantify the approximate rate of temperature reduction achievable by use of an exemplary embodiment of the present technology. Target temperature reduction is 4° C. Data were collected and plotted on a common X-Y graph, as shown in FIG. 10.

The arrangement of equipment for this experiment is shown in FIG. 1. A brief description of each piece of equipment is as follows:

1. The heat transfer device 102 was an exemplary embodiment of a heat transfer device according to the present technology
2. An insulated container, 96 cm (l)×36 cm (w)×36 cm (h), containing 88 kg water at the initial temperature shown in Table 1 represented the mass to be cooled.
3. A 110V electric pump, Little Giant Model PES-70 (4.4 L/min free-flow) was used to circulate hot water within the insulated container (2) to maintain homogeneous temperature of water within this container.
4. The heat exchanger 104 comprised an insulated container, 51 cm (l)×28 cm (w)×34 cm (d), containing 40 kg ice water.
5. The pump 118 comprised a 110V electric pump, Little Giant Model PES-70 (250 mL/min as installed) and was used to provide circulation of coolant from the heat exchanger 104 through the external supply tube 110, then through the heat transfer device 102, then through the external return tube 112, and back to the heat exchanger 104.
6. The external supply tube 110 comprised a Watts clear vinyl #SVKI10, ⅝" (od)×½" (id)×42" (l), to carry coolant from the heat exchanger 104 to the heat transfer device 102.
7. The external return tube 112 comprised a Watts clear vinyl #SVKI10, ⅝" (od)×½" (id)×42" (l), to carry coolant from heat transfer device 102 to the heat exchanger 104.
8. A thermometer 124, such as a digital waterproof thermometer including 2 remote probes 126, Taylor Model 1441, was used to monitor:
   a. coolant temperature ($T_3$ as shown in FIG. 1) near the discharge of the external return tube 112 into the heat exchanger 104;
   b. ambient temperature ($T_4$ as shown in FIG. 1) within test cell.
9. A thermometer 124, such as a digital waterproof thermometer including 2 remote probes 126, Taylor Model 1441, was used to monitor:
   a. hot water temperature ($T_1$ as shown in FIG. 1) within insulated container (2), at the end opposite circulation pump (3).
   b. hot water temperature ($T_2$ as shown in FIG. 1) within insulated container (2), at the end nearest circulation pump (3).

The body to be cooled in each iteration of this experiment was an 88-kg mass of water, which was held in an insulated container (2) measuring 94×36×26 cm. This mass was chosen as it is representative of the body mass of a typical adult male. Heat transfer to ambient air by free convection was through the 94×36 cm top surface of the body of water. Initial temperature of this mass of water for each iteration of the procedure is shown in Table 1.

The coolant for each iteration of this experiment was a 30-kg mass of water containing an additional 10-kg of ice, which was held in an insulated container. Ice was used to keep the temperature of the coolant nearly constant for the duration of each iteration of the experiment without the need for a powered chiller, and was replenished at the start of each iteration for which the conductive cooling mode was enabled.

There are two modes of temperature reduction to consider in this experiment. They are convective cooling to ambient air, and conductive cooling through the heat transfer device. To quantify the contribution of each mode to the total temperature reduction, a control case was run with the conductive cooling mode disabled (no coolant circulated through the heat transfer device). The procedure was then run two additional times with the conductive cooling mode enabled (the heat transfer device was submerged in the body of hot water, and coolant circulated through it). The difference between temperature reduction rates, with and without conductive cooling enabled, is the temperature reduction rate due to conductive cooling through the heat transfer device.

Summary of data for each iteration of the experiment is shown in Table 1 below:

TABLE 1

Cooling Experiment Results

| Iteration | Description | $T_{init,avg}$ ° C. | $T_{amb,avg}$ ° C. | $T_{coolant,avg}$ ° C. | 4° C. drop time (hh:mm) |
|---|---|---|---|---|---|
| 1 | Control case, convection to ambient only | 38.8 | 19.6 | N/A | 02:53 |
| 2 | Conductive cooling enabled, Run #1 | 39.4 | 20.3 | 3.9 | 01:39 |

TABLE 1-continued

Cooling Experiment Results

| Iteration | Description | $T_{init,avg}$ ° C. | $T_{amb,avg}$ ° C. | $T_{coolant,avg}$ ° C. | 4° C. drop time (hh:mm) |
|---|---|---|---|---|---|
| 3 | Conductive cooling enabled, Run #2 | 38.1 | 20.4 | 3.5 | 01:38 |

In Table 1:
"$T_{init,avg}$" is the average initial temperature of the body to be cooled, average of two readings
"$T_{amb,avg}$" is the average ambient temperature for the duration of the iteration
"$T_{coolant,avg}$" is the average coolant temperature for the duration of the iteration
"4° C. drop time" is the time required to achieve a 4° C. reduction in average temperature of the body to be cooled.

Thus, conductive cooling through the exemplary heat transfer device employed in this Example significantly decreases time to achieve a 4° C. temperature reduction.

Example 2: Operative Temperature Management

A heat transfer device according to the present technology was utilized in an animal study as described below. The heat transfer region of the heat transfer device was approximately 70 centimeters in length (to accommodate the length of the snout) and had a diameter of about 1.4 centimeters, for a surface area of about 305 cm².

A large swine with a mass of 70 kg was chosen to best represent the size and average mass of a human patient. The swine was singly housed in an Association for the Assessment and Accreditation of Laboratory Animal Care, International (AAALAC) accredited facility, with primary enclosures as specified in the USDA Animal Welfare Act (9 CFR Parts 1, 2 and 3) and as described in the *Guide for the Care and Use of Laboratory Animals* (National Academy Press, Washington D.C., 1996).

The swine was anesthetized with a pre-anesthetic mix of Telozole/Xylazine, then provided with anesthesia via inhalational route with isoflurane 2% after endotracheal intubation achieved with standard endotracheal intubation equipment and technique well known to those skilled in the art. Muscular paralysis was obtained with intravenous paralytic. Temperature was monitored continuously via rectal thermocouple probe placed after anesthesia and endotracheal intubation.

A commercially available thermal water bath and circulator (Gaymar Meditherm MTA-5900) was utilized to provide a controlled-temperature heat transfer medium to the heat transfer device. The specific heat transfer medium utilized was distilled water. Specifications of the commercially available thermal water bath and circulator are as follows:
  Dimensions: 94 cm H×35 cm W×48 cm D
  Weight: 54.9 kg empty; 64.0 kg full
  Material: Aluminum Shell, 16 Gauge Steel Chassis
  Flow Rate: 1 liter per minute
  Power: 220V, 240V, 50 Hz, 6 A
  Temperature: Manual: 4 to 42° C., Automatic: 30 to 39° C.
  Electrical Cord: 4.6 m detachable power cord The heat transfer device was connected to the thermal water bath and circulator, which was then powered on and allowed to equilibrate while preparing the swine.

After successful anesthesia, paralysis, and endotracheal intubation of the swine, a central semi-rigid stylet was placed into the heat transfer device and the heat transfer device was lubricated with a biocompatible lubricant.

The heat transfer device was then introduced into the esophagus of the swine using standard esophageal intubation technique well known to those skilled in the art. An external measurement of the distance from oropharyngeal opening to xiphoid process served as an indicator to which the depth of the heat transfer device was inserted. Confirmation of proper depth of insertion was obtained by successful aspiration of gastric contents through the gastric lumen of the heat transfer device.

In order to demonstrate the capacity of the heat transfer device to successfully warm a patient under hypothermic conditions typically found in the operating room environment, the swine was cooled by setting the supply temperature of the heat transfer medium to the low set point (4° C.) for a time sufficient to reduce the temperature of the swine to 33.6° C.

Data from the cooling portion of the experiment are shown in Table 2. As can be seen in Table 2, a 1° C. reduction in core body temperature of a 67.5 kg swine was achieved in about 40 minutes; a 2° C. reduction in core body temperature of a 67.5 kg swine was achieved in about 80 minutes; a 3° C. reduction in core body temperature of a 67.5 kg swine was achieved in about 125 minutes; and a 4° C. reduction in core body temperature of a 67.5 kg swine was achieved in about 175 minutes.

TABLE 2

Esophageal Cooling.

| Time (min) | Rectal Temperature (° C.) |
|---|---|
| 0 | 37.8 |
| 10 | 37.8 |
| 15 | 37.6 |
| 20 | 37.4 |
| 25 | 37.3 |
| 32 | 37.2 |
| 35 | 37 |
| 40 | 36.8 |
| 45 | 36.7 |
| 50 | 36.6 |
| 55 | 36.4 |
| 60 | 36.3 |
| 65 | 36.1 |
| 70 | 36 |
| 75 | 35.9 |
| 80 | 35.7 |
| 85 | 35.6 |
| 90 | 35.5 |
| 95 | 35.4 |
| 100 | 35.3 |
| 105 | 35.2 |
| 110 | 35.1 |
| 115 | 35 |
| 120 | 34.9 |
| 125 | 34.8 |
| 130 | 34.7 |
| 135 | 34.6 |
| 140 | 34.5 |
| 145 | 34.4 |
| 150 | 34.4 |
| 155 | 34.3 |
| 160 | 34.2 |
| 165 | 34.1 |
| 170 | 33.9 |
| 175 | 33.8 |
| 180 | 33.7 |
| 185 | 33.6 |

Figure 11:
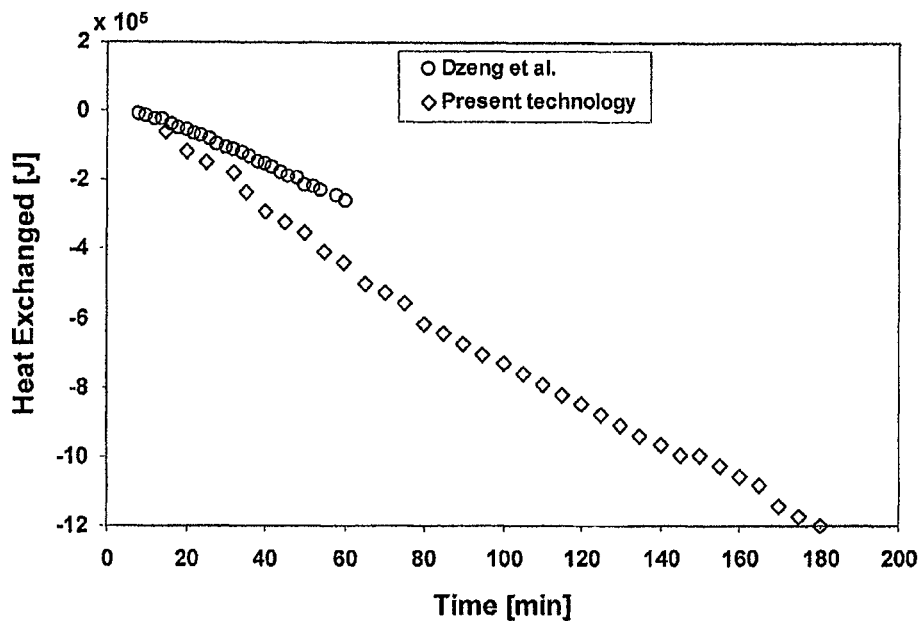
FIG. 11 is a graphed comparison of the rate of cooling achieved by a heat transfer device of the present technology as compared to the rate of cooling demonstrated in US Patent Application Publication 2004/0210281 to Dzeng et al.

FIG. 11 shows a comparison of the rate of cooling achieved by a heat transfer device of the present technology as compared to the rate of cooling demonstrated in US Patent Application Publication 2004/0210281 to Dzeng et al. (now U.S. Pat. No. 7,758,623). In order to make an accurate comparison, and to properly account for the differences in mass between the two experiments, the total amount of heat extracted in each case is calculated in standard units of Joules. Using a standard specific heat capacity of water ($c_p$=4.186 J/g C) to model the specific heat capacity of the experimental animal, the heat extracted at each time point is calculated as $Q=m(\Delta T)c_p$, where m is the mass of the experimental animal, and $\Delta T$ is the temperature difference obtained at each time point.

At the time point of one hour, the total heat extracted is 439 kJ in one hour (122 Watts) with a heat transfer device of the present technology, as compared to a total heat extraction of 260 kJ in one hour (72 Watts) achieved with the device mentioned by Dzeng et al. in US Patent Application Publication 2004/0210281 (now U.S. Pat. No. 7,758,623).

The results of the swine cooling experiment show that even in a relatively large animal, with correspondingly greater heat reservoir capacity, a significantly greater heat transfer rate is achievable with a heat transfer device of the present technology than with prior devices such as those mentioned by Dzeng et al. in US Patent Application Publication 2004/0210281 (now U.S. Pat. No. 7,758,623). From the data presented, the total heat extracted, and the consequent cooling achieved, can be seen to be significantly greater with a heat transfer device of the present technology as compared to the rate of heat transfer and cooling achieved with prior devices such as those mentioned by Dzeng et al. in US Patent Application Publication 2004/0210281 (now U.S. Pat. No. 7,758,623). Thus, it was unexpectedly and surprisingly observed that the cooling rate achieved with a heat transfer device of the present technology is significantly greater than that achieved with other devices and that the methods and devices of the present technology transfer more heat per unit time than other devices. Without wishing to be bound by any particular theory, it is thought that these unexpected findings can be attributed to, for example, one or more of the following features of the heat transfer device: the increased contact surface between the heat transfer region of the heat transfer device and the patient's anatomy; the reduction in heat transfer resistance across the device achieved by manufacturing heat transfer devices of the present technology with thinner wall thicknesses; the superior heat transfer characteristics of the materials used to construct the heat transfer devices of the present technology; and the reduction of gastric pressure through gastric ventilation.

Following cooling, the set point temperature of the heat transfer medium was switched to a warming mode (42° C.).

To further simulate the hypothermia inducing conditions of the operating room, the swine was left exposed to the ambient temperature of the room (22° C.), continuously anesthetized with inhalational anesthesia, paralyzed with a non-depolarizing paralytic to prevent shivering, and provided with a continuous flow of maintenance room temperature intravenous fluid hydration.

Figure 12:
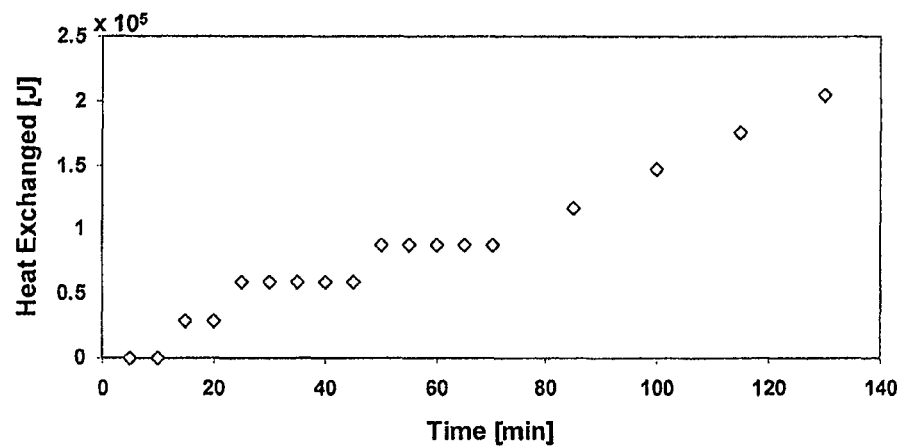
FIG. 12 is a graph showing the total amount of heat transferred during the warming and maintenance phase of the experiment.

Data from the warming and maintenance phase of the experiment are shown in Table 3. The data in Table 3 demonstrate an initial maintenance of the swine body temperature at 33.6° C., followed by a successful safe, gradual increase in body temperature for the duration of the experiment. FIG. 12 shows the total amount of heat transferred, as calculated above, during the warming and maintenance phase of the experiment.

TABLE 3

Operative Temperature Management and Warming

| Time (min) | Rectal Temperature (° C.) |
| --- | --- |
| 0 | 33.6 |
| 5 | 33.6 |
| 10 | 33.6 |
| 15 | 33.7 |
| 20 | 33.7 |
| 25 | 33.8 |
| 30 | 33.8 |
| 35 | 33.8 |
| 40 | 33.8 |
| 45 | 33.8 |
| 50 | 33.9 |
| 55 | 33.9 |
| 60 | 33.9 |
| 65 | 33.9 |
| 70 | 33.9 |
| 85 | 34 |
| 100 | 34.1 |
| 115 | 34.2 |
| 130 | 34.3 |
| 145 | 34.3 |
| 160 | 34.3 |
| 175 | 34.4 |
| 190 | 34.5 |
| 205 | 34.5 |

Consequently, the data demonstrate that a heat transfer device of the present technology can maintain, and increase, body temperature while the patient is exposed to adverse hypothermic conditions of an operating room environment.

Example 3: Temperature Modulation

In an experimental model of therapeutic temperature modulation, a heat transfer device according to the present technology was utilized in an animal study as described below.

Five large swine with masses of between 60 kg and 70 kg were chosen to best represent the size and average mass of a human patient. The study utilized methods consistent with current veterinary and USDA standards, with a state-of-the-art, Association for Assessment and Accreditation of Laboratory Animal Care (AAALAC) International-accredited vivarium. Animal care and handling of was in accord with Office of Laboratory Animal Welfare guidance for humane care and use of animals and with regulations outlined in the USDA Animal Welfare Act (9 CFR Parts 1, 2 and 3) and the conditions specified in the Guide for the Care and Use of Laboratory Animals (National Academy Press, Washington D.C., 1996).

Swine were anesthetized with a pre-anesthetic dose of ketamine, then provided with anesthesia via inhalational route with isoflurane 2% after endotracheal intubation achieved with standard endotracheal intubation equipment and technique well known to those skilled in the art.

Temperature was monitored continuously via continuous rectal thermometer, intravascular thermometer, and both vaginal and/or bladder thermometer using temperature-sensing Foley catheters, all placed after anesthesia and endotracheal intubation.

A commercially available thermal water bath and circulator (Gaymar Meditherm III, MTA-7900) was utilized to provide a controlled-temperature heat transfer medium to the heat transfer device. The specific heat transfer medium utilized was distilled water. Specifications of the commercially available thermal water bath and circulator are as follows:

Size: 37"h×14"w×18¾"d (94 cm×36 cm×46 cm)
Weight: Empty: 121 lbs. (54.9 kg), Full: 141 lbs. (64.0 kg)
Material: Aluminum shell, 16-gauge steel chassis
Flow Rate: 17 gph per minute
Power: 120 VAC, 60 Hz, 11.5 amps
Electrical Cord: 15 ft. (4.6 m) power cord (16/3 SO), hospital-grade plug
Temperature Settings: Manual: Water temperature selection range 4 to 42° C. (39.2 to 107.6° F.)
Automatic: Patient temp. selection range 30 to 41° C. (86 to 105.8° F.)
Code: UL416 and CSA C22.2, EMC meets EN60601-1-2

After successful anesthesia and endotracheal intubation of the swine, the heat transfer device was connected to the external thermal water bath and circulator which was then powered on to initiate the flow of heat exchange medium (distilled water). The heat transfer device was then lubricated with a biocompatible lubricant and introduced into the esophagus of the swine using standard esophageal intubation technique well known to those skilled in the art. No stylets or additional techniques to enhance rigidity of the heat transfer device were necessary to allow proper placement. An external measurement of the distance from oropharyngeal opening to xiphoid process served as an indicator to which the depth of the heat transfer device was inserted. Confirmation of proper depth of insertion was obtained by successful auscultation of stomach gurgling upon injection of 20 mL of air, aspiration of gastric contents through the gastric lumen of the heat transfer device, and x-ray fluoroscopy demonstrating presence of the radio-opaque stripe and tip in the stomach.

Starting from baseline temperature measured prior to preparation, swine temperature was reduced by 4° C. by setting the external chiller to run in an automatic mode, with set point that was 4° C. below the baseline temperature. At 24 hours after initiation of cooling, a rewarming protocol was initiated, in which the external heat exchanger was set to a warming mode, while swine temperature was gradually allowed to rewarm at a rate of approximately 0.5° C. per hour. Upon surpassing a goal temperature of 36° C., recovery from anesthesia was initiated, and each swine was then monitored post recovery for periods of between 3 and 14 days.

Figure 13:
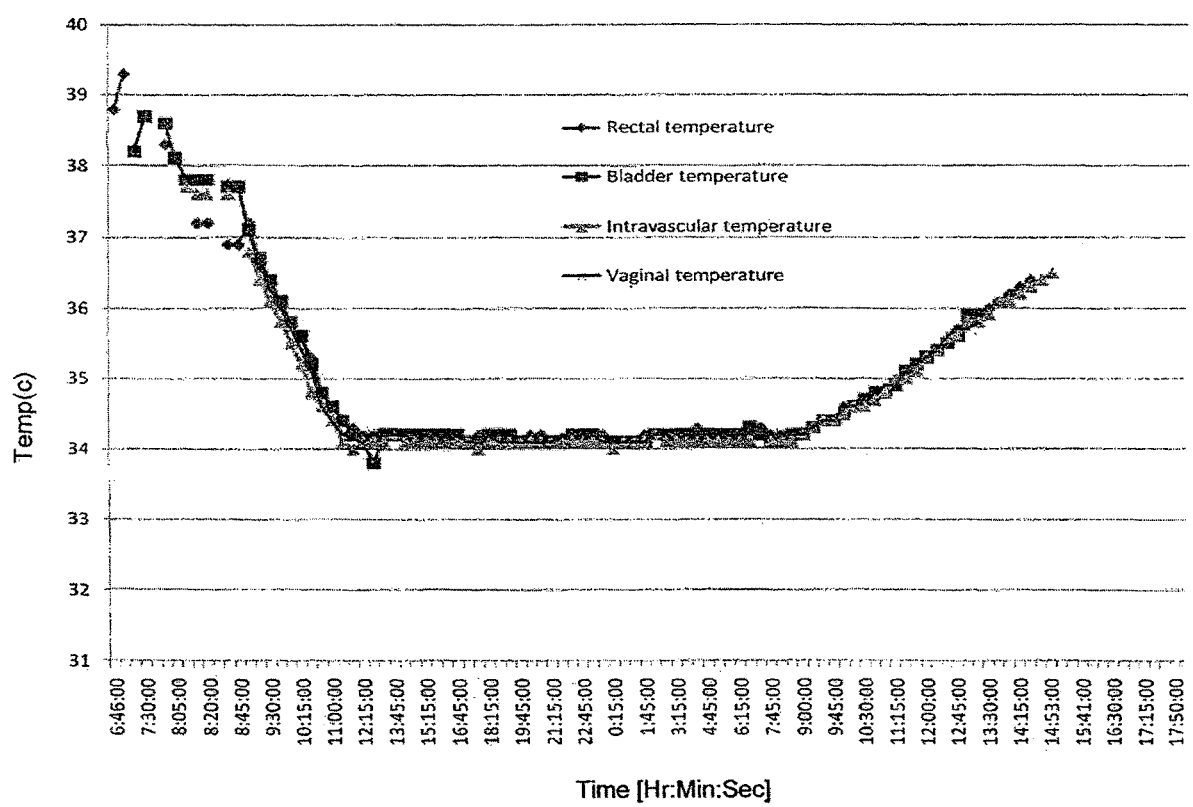
FIG. 13 is a temperature plot depicting temperature modulation achieved with an exemplary cooling device according to an embodiment of the present technology.

A representative plot of temperature versus time is shown in FIG. 13. Throughout the entire protocol, no evidence of thermoregulatory shivering was seen, and therefore no muscular paralysis medications were required, and no medications commonly utilized to treat shivering (such as meperidine, dexmedetomidine, midazolam, fentanyl, ondansetron, or magnesium sulfate) were required.

Existing methods to control and modify patient temperature typically demonstrate significant variation around goal temperature during treatment, with up to plus or minus 1.3° C. variance from goal temperature seen in some cases. Inadvertent increases above the goal temperature lessen the therapeutic benefit of hypothermia. Inadvertent overcooling can result in significant complications, including cardiac arrhythmias, coagulopathy, and an increased rate of infection. In contrast, devices of the present technology provided the surprising and unexpected benefit of reduced variation around the goal temperature throughout the steady-state of the treatment protocol. Variation around the goal temperature fell far below that which is demonstrated by other devices, and in fact remained for almost the entire protocol within plus or minus 0.1° C. of goal temperature.

During the cooling process, temperature measurements were performed every 15 minutes initially, and then every 30 minutes once steady state was reached. The rate of temperature reduction ranged from 0.8° C./hour to as fast as 2.4° C./hour, with an average of 1.4° C./hour. The rate of temperature reduction was as fast as 703 kJ/hour, with an average of 410 kJ/hour. Thus, it was unexpectedly and surprisingly observed that the cooling rate achieved with a heat transfer device of the present technology is greater than that achieved with many other devices and that the methods and devices of the present technology extract more heat per unit time than many other devices.

During the warming process, temperature measurements were performed every 15 minutes. As can be seen in the figure, at each 15 min. interval, the rate of temperature increase ranged from zero to as high as 1.2° C./hour, with an average of 0.39° C./hour. Thus, it was unexpectedly and surprisingly observed that the warming rate achieved with a heat transfer device of the present technology is greater than that achieved with many other devices and that the methods and devices of the present technology impart more heat per unit time than many other devices.

SPECIFIC EMBODIMENTS

The methods described herein can be illustrated by the following embodiments enumerated in the numbered sentences that follow:

1. A method for inducing systemic hypothermia comprising:
   inserting a heat transfer device into an esophagus of a patient, wherein the heat transfer device includes a fluid path defined by an inflow lumen and an outflow lumen;
   initiating flow of a cooling medium along the fluid path; and
   circulating the medium along the fluid path for a time sufficient to induce systemic hypothermia in the patient.

2. The method of sentence 1, wherein the heat transfer device includes a discrete heat transfer region and the heat transfer region is confined to the esophagus.

3. The method of sentence 1, further comprising cooling the medium to a temperature below normothermia.

4. The method of sentence 1, further comprising maintaining the patient in a state of hypothermia for at least two hours.

5. The method of sentence 1, further comprising monitoring at least one physiological parameter of the patient.

6. The method of sentence 5, wherein the at least one physiological parameter is body temperature.

7. The method of sentence 6, further comprising maintaining the body temperature below about 34° C.

8. The method of sentence 7, further comprising maintaining the body temperature between about 32° C. to about 34° C.

The devices described herein can be illustrated by the following embodiments enumerated in the numbered sentences that follow:

1. An esophageal heat transfer device comprising:
   (a) a plurality of lumens configured to provide a fluid path for flow of a heat transfer medium;
   (b) a proximal end including an input port and an output port;
   (c) a distal end configured for insertion into an esophagus of a patient.

2. The heat transfer device of sentence 1, further comprising a hollow tube having a distal end configured to extend into a stomach of the patient.

3. The heat transfer device of sentence 1, further comprising an anti-bacterial coating.

4. The heat transfer device of sentence 1, further comprising an expandable balloon.

The methods described herein can be illustrated by the following embodiments enumerated in the numbered sentences that follow:

1. A method for treating or preventing injury caused by an ischemic condition comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

2. A method for treating or preventing ischemia-reperfusion injury comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

3. A method for treating or preventing neurological injury comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

4. The method of sentence 3, wherein the neurological injury is associated with stroke, traumatic brain injury, spinal cord injury, subarachnoid hemorrhage, out-of-hospital cardiopulmonary arrest, hepatic encephalopathy, perinatal asphyxia, hypoxic-anoxic encephalopathy, infantile viral encephalopathy, near-drowning, anoxic brain injury, traumatic head injury, traumatic cardiac arrest, newborn hypoxic-ischemic encephalopathy, hepatic encephalopathy, bacterial meningitis, cardiac failure, post-operative tachycardia, or acute respiratory distress syndrome.

5. The method of sentence 4, wherein the stroke is ischemic stroke.

6. A method for treating or preventing cardiac injury comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

7. A method for treating myocardial infarction comprising:
inducing mild therapeutic hypothermia.

8. A method for treating stroke comprising:
inducing mild therapeutic hypothermia.

9. A method for treating traumatic brain injury comprising:
inducing mild therapeutic hypothermia.

10. A method for treating Acute Respiratory Distress Syndrome comprising:
inducing mild therapeutic hypothermia.

11. The method of any one of sentences 7-10, wherein the hypothermia is systemic hypothermia.

12. The method of any one of sentences 7-10, wherein the hypothermia is induced via esophageal cooling.

13. The method of any one of sentences 7-10, further comprising maintaining the patient in a state of hypothermia for at least two hours.

14. The method of sentence 13, further comprising maintaining the patient in a state of hypothermia for at least twenty-four hours.

15. The method of sentence 14, further comprising maintaining the patient in a state of hypothermia for at least seventy-two hours.

16. The method of any one of sentences 7-10, further comprising monitoring at least one physiological parameter of the patient.

17. The method of sentence 16, wherein the at least one physiological parameter is body temperature.

18. The method of sentence 17, further comprising maintaining the body temperature below about 34° C.

19. The method of sentence 18, further comprising maintaining the body temperature between about 32° C. to about 34° C.

20. The method of sentence 12, further comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

21. A method for treating cardiac arrest comprising:
inducing systemic hypothermia via esophageal cooling.

22. The method of sentence 21, further comprising:
inserting a heat transfer device into an esophagus of a patient, wherein the heat transfer device includes a fluid path defined by an inflow lumen and an outflow lumen;
initiating flow of a cooling medium along the fluid path; and
circulating the medium along the fluid path for a time sufficient to induce systemic hypothermia in the patient.

The methods and devices described herein can be illustrated by the following embodiments enumerated in the numbered sentences that follow:

1. A device for cooling or warming at least one portion of a patient's body, comprising:
a heat transfer device including a proximal end, a distal end, and at least one flexible tube extending therebetween;
the proximal end including a heat transfer medium input port and a heat transfer medium output port;
the distal end configured for insertion into an orifice of a patient;
the at least one flexible tube defining an inflow lumen and an outflow lumen;
the lumens configured to provide a fluid path for flow of a heat transfer medium;
a supply line connected to the input port; and
a return line connected to the output port.

2. The device of sentence 1, wherein the heat transfer medium is a cooling medium.

3. A method of using the device of sentence 2 to treat or prevent injury caused by an ischemic condition comprising:
inserting the distal end of the heat transfer device nasally or orally;
advancing the distal end into an esophagus;
initiating flow of a cooling medium along the fluid path; and
circulating the medium along the fluid path for a time sufficient to induce systemic hypothermia in the patient.

4. A method of using the device of sentence 2 to treat or prevent ischemia-reperfusion injury comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

5. A method of using the device of sentence 2 to treat or prevent neurological injury comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

6. A method of using the device of sentence 2 to treat or prevent cardiac injury comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

7. A method of using the device of sentence 2 to treat myocardial infarction comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

8. A method of using the device of sentence 2 to treat stroke comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

9. A method of using the device of sentence 2 to treat traumatic brain injury comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

10. A method of using the device of sentence 2 to treat Acute Respiratory Distress Syndrome comprising:
 inserting the distal end of the heat transfer device nasally or orally;
 advancing the distal end into an esophagus;
 initiating flow of a cooling medium along the fluid path; and
 circulating the medium along the fluid path for a time sufficient to induce systemic hypothermia in the patient.

11. The method of any one of sentences 3-10, further comprising cooling the medium to a temperature below normothermia.

12. The method of any one of sentences 3-10, further comprising maintaining the patient in a state of hypothermia for at least two hours.

13. The method of sentence 12, further comprising maintaining the patient in a state of hypothermia for at least twenty-four hours.

14. The method of sentence 13, further comprising maintaining the patient in a state of hypothermia for at least seventy-two hours.

15. The method of any one of sentences 3-10, further comprising monitoring at least one physiological parameter of the patient.

16. The method of sentence 15, wherein the at least one physiological parameter is body temperature.

17. The method of sentence 16, further comprising maintaining the body temperature below about 34° C.

18. The method of sentence 17, further comprising maintaining the body temperature between about 32° C. to about 34° C.

The methods described herein can be illustrated by the following embodiments enumerated in the numbered sentences that follow:

1. A method for controlling core body temperature in a patient comprising:
 inserting a heat transfer device into an esophagus of a patient, wherein the heat transfer device includes a fluid path defined by an inflow lumen and an outflow lumen;
 initiating flow of a heat transfer medium along the fluid path; and
 circulating the medium along the fluid path for a time sufficient to control core body temperature in the patient.

2. The method of sentence 1, wherein the heat transfer device includes a discrete heat transfer region and the heat transfer region is confined to the esophagus.

3. The method of sentence 1, further comprising cooling the medium to a temperature below normothermia.

4. The method of sentence 1, further comprising warming the medium to a temperature above normothermia.

5. The method of sentence 1, further comprising maintaining the patient in a state of hypothermia for at least two hours.

6. The method of sentence 1, further comprising maintaining the patient at normothermia for at least two hours.

7. The method of sentence 1, further comprising monitoring at least one physiological parameter of the patient.

8. The method of sentence 7, wherein the at least one physiological parameter is body temperature.

9. The method of sentence 1, further comprising maintaining the body temperature below about 34° C.

10. The method of sentence 1, further comprising maintaining the body temperature between about 32° C. to about 34° C.

11. The method of sentence 1, further comprising maintaining the body temperature at about 37° C.

The methods described herein can be illustrated by the following embodiments enumerated in the numbered sentences that follow:

1. A method for operative temperature management comprising:
 inserting a heat transfer device into an esophagus of a patient, wherein the heat transfer device includes a fluid path defined by an inflow lumen and an outflow lumen;
 initiating flow of a heat transfer medium along the fluid path; and
 circulating the medium along the fluid path for a time sufficient to manage core body temperature in the patient.

2. The method of sentence 1, further comprising maintaining the patient in a state of hypothermia for at least two hours.

3. The method of sentence 1, further comprising maintaining the body temperature below about 34° C.

4. The method of sentence 1, further comprising maintaining the body temperature between about 32° C. to about 34° C.

5. The method of sentence 1, further comprising maintaining the patient in a state of normothermia for at least two hours.

6. The method of sentence 1, further comprising maintaining the body temperature at about 37° C.

7. The method of sentence 1, further comprising monitoring at least one physiological parameter of the patient.

8. The method of sentence 7, wherein the at least one physiological parameter is body temperature.

The devices described herein can be illustrated by the following embodiments enumerated in the numbered sentences that follow:

1. An esophageal heat transfer device comprising:
(a) a plurality of lumens configured to provide a fluid path for flow of a heat transfer medium;
(b) a heat transfer region configured for contacting esophageal epithelium of a patient;
(c) a proximal end including an input port and an output port;
(d) a distal end configured for insertion into an esophagus of a patient.

2. The heat transfer device of sentence 1, further comprising a hollow tube having a distal end configured to extend into a stomach of the patient.

3. The heat transfer device of sentence 1, wherein the heat transfer region is capable of contacting substantially all of the esophageal epithelium.

4. The heat transfer device of sentence 1, wherein the heat transfer region comprises a semi-rigid material.

5. The heat transfer device of sentence 1, wherein the device is capable of cooling at a rate of about 1.2° C./hr to about 1.8° C./hr.

6. The heat transfer device of sentence 1, wherein the device is capable of cooling a mass at a rate of about 350 kJ/hr to about 530 kJ/hr.

7. The heat transfer device of sentence 6, wherein the device is capable of cooling a mass at a rate of about 430 kJ/hr.

8. The heat transfer device of sentence 1, wherein the device includes a heat transfer region with a surface area of at least about 100 $cm^2$.

9. The heat transfer device of sentence 8, wherein the heat transfer region has a surface area of about 140 $cm^2$.

The devices and systems described herein can be illustrated by the following embodiments enumerated in the numbered sentences that follow:

1. A system for cooling or warming at least one portion of a patient's body, comprising:
a heat transfer device including a proximal end, a distal end, and at least one semi-rigid tube extending therebetween;
the proximal end including a heat transfer medium input port and a heat transfer medium output port;
the distal end configured for insertion into an orifice of a patient;
the at least one semi-rigid tube defining an inflow lumen and an outflow lumen;
the lumens configured to provide a fluid path for flow of a heat transfer medium;
a supply line connected to the input port; and
a return line connected to the output port.

2. The system of sentence 1, wherein the orifice is an esophageal lumen.

3. The system of sentence 2, wherein the heat transfer device comprises a heat transfer region capable of contacting substantially all of the esophageal epithelium.

4. The system of sentence 1, further comprising a hollow tube having a distal end configured to extend into a stomach of the patient.

5. The heat transfer device of sentence 1, wherein the device is capable of cooling at a rate of about 1.2° C./hr to about 1.8° C./hr.

6. The system of sentence 1, wherein the device is capable of cooling a mass at a rate of about 350 kJ/hr to about 530 kJ/hr.

7. The system of sentence 6, wherein the device is capable of cooling a mass at a rate of about 430 kJ/hr.

8. The system of sentence 1, wherein the device includes a heat transfer region with a surface area of at least about 100 $cm^2$.

9. The system of sentence 8, wherein the heat transfer region has a surface area of about 140 $cm^2$.

The devices and systems described herein can be illustrated by the following embodiments enumerated in the numbered sentences that follow:

1. A system for controlling core body temperature of a subject, comprising:
a heat transfer tube insertable within the esophagus of the subject, wherein the tube is configured to contact the epithelial lining of the esophagus;
an external heat exchanger containing a heat transfer fluid;
a pump for flowing the heat transfer fluid through a circuit within the heat transfer tube;
a heat transfer element in contact with the external heat exchanger; and
a sensor for detecting a parameter and generating a signal representative of the parameter, wherein the signal is transmitted to a microprocessor to control (i) the flow heat transfer fluid within the circuit or (ii) the temperature of the heat transfer fluid.

2. The system of sentence 1, wherein the sensor is a temperature sensor positioned distal to the heat transfer tube and configured to generate a signal representing the core body temperature of the subject.

3. The system of sentence 2, wherein the microprocessor receives a target temperature input and responds to the signal from the temperature sensor with a proportional integrated differential response to control the rate at which the subject approaches the target temperature.

4. The system of sentence 1, wherein the sensor is a bubble detector and configured to generate a signal representing the presence of air in the circuit.

5. The system of sentence 1, wherein the heat transfer tube comprises a heat transfer region capable of contacting substantially all of the esophageal epithelium.

6. The system of sentence 1, further comprising a hollow tube having a distal end configured to extend into a stomach of the patient.

7. The system of sentence 1, wherein the device is capable of cooling at a rate of about 1.2° C./hr to about 1.8° C./hr.

8. The system of sentence 1, wherein the device is capable of cooling a mass at a rate of about 350 kJ/hr to about 530 kJ/hr.

9. The system of sentence 1, wherein the device is capable of cooling a mass at a rate of about 430 kJ/hr.

10. The system of sentence 1, wherein the device includes a heat transfer region with a surface area of at least about 100 cm².

11. The system of sentence 10, wherein the heat transfer region has a surface area of about 140 cm².

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended sentences.

The invention claimed is:

1. An esophageal heat transfer device comprising:
   a distal end configured for insertion into a nostril or mouth of a patient;
   a heat transfer medium supply tube that defines an inflow lumen and forms a heat transfer region, wherein the heat transfer region is configured to transfer heat to or extract heat from the esophagus when a heat transfer medium flows through the inflow lumen;
   a heat transfer medium return tube that defines an outflow lumen;
   an input port for receiving the heat transfer medium from a source, wherein said input port is connected to the heat transfer medium supply tube; and
   an output port for returning the heat transfer medium to the source, wherein said output port is connected to the heat transfer medium return tube;
   wherein the heat transfer region is not inflatable;
   wherein the heat transfer medium return tube is not positioned within the heat transfer medium supply tube; and
   wherein the heat transfer medium supply tube and the heat transfer medium return tube have substantially equal inside diameters.

2. The device of claim 1, wherein the heat transfer region has a surface area of at least about 100 cm².

3. The device of claim 1, further comprising a temperature sensor.

4. The device of claim 1, wherein the heat transfer medium return tube and the heat transfer medium supply tube are arranged in parallel.

5. The device of claim 4, wherein the heat transfer medium return tube and the heat transfer medium supply tube share a common inner wall.

6. The device of claim 1, further comprising a sensor for detecting a parameter and generating a signal representative of the parameter.

7. An esophageal heat transfer device comprising:
   a heat transfer medium supply tube that defines an inflow lumen;
   a heat transfer medium return tube that defines an outflow lumen;
   wherein the heat transfer medium supply tube and the heat transfer medium return tube are configured such that at least a portion of an exterior wall of the heat transfer medium supply tube is in contact with esophageal tissue upon placement of the device in a patient;
   wherein the portion of the exterior wall constitutes a heat transfer region configured to transfer heat to or extract heat from the esophageal tissue when a heat transfer medium flows through the inflow lumen;
   wherein the heat transfer region is not inflatable; and
   wherein the heat transfer medium return tube is not positioned within the heat transfer medium supply tube.

8. The device of claim 7, wherein the heat transfer medium supply tube and the heat transfer medium return tube have substantially equal diameters.

9. The device of claim 7, wherein the heat transfer medium return tube and the heat transfer medium supply tube are arranged in parallel.

10. The device of claim 9, wherein the heat transfer medium return tube and the heat transfer medium supply tube share a common inner wall.

11. The device of claim 7, further comprising an input port for receiving a heat transfer medium from a source, wherein said input port is connected to the heat transfer medium supply tube.

12. The device of claim 11, further comprising an output port for returning the heat transfer medium to the source, wherein said output port is connected to the heat transfer medium return tube.

13. The device of claim 7, further comprising a temperature sensor.

14. The device of claim 7, further comprising a sensor for detecting a parameter and generating a signal representative of the parameter.

15. An esophageal heat transfer device comprising:
   a distal end configured for insertion into a nostril or mouth of a patient;
   a proximal end comprising an input port for receiving a heat transfer medium from a source and an output port for returning the heat transfer medium to the source;
   a length of tubing that defines a multi-lumen cavity, the length of tubing comprising an inner divider wall disposed longitudinally therein, the inner divider wall dividing the cavity into at least a first lumen and a second lumen, wherein the first lumen and the second lumen are arranged in parallel to each other, and wherein the first lumen and the second lumen are in fluid communication with each other, thereby defining a fluid path for flow of the heat transfer medium;
   wherein the first lumen is defined by a first circumferential portion of an interior wall of the length of tubing and the inner divider wall and the second lumen is defined by a second circumferential portion of an interior wall of the length of tubing and the inner divider wall; and
   wherein at least a portion of an exterior wall of the length of tubing is in contact with esophageal tissue upon placement of the device in a patient and the portion of the exterior wall constitutes a non-inflatable heat transfer region configured to transfer heat to or extract heat from the esophageal tissue when the heat transfer medium flows through the first and/or second lumen.

16. The device of claim 15, further comprising a temperature sensor.

17. The device of claim 15, wherein the inner divider wall is connected to or coextensive with the interior wall of the length of tubing.

18. The device of claim 15, wherein a first end of the inner divider wall is connected to or coextensive with a first site on the interior wall of the length of tubing and a second end of the inner divider wall is connected to or coextensive with a second site on the interior wall of the length of tubing.

19. The device of claim 15, wherein the first site on the interior wall of the length of tubing and the second site on the interior wall of the length of tubing are about 180 degrees apart.

20. The device of claim 15, further comprising a sensor for detecting a parameter and generating a signal representative of the parameter.

* * * * *